US012601747B2

(12) United States Patent
Batxelli-Molina et al.

(10) Patent No.: US 12,601,747 B2
(45) Date of Patent: Apr. 14, 2026

(54) BIOMARKER COMBINATIONS TO SIMULTANEOUSLY EVALUATE NON-ALCOHOLIC STEATOHEPATITIS AND HEPATIC FIBROSIS STATUS

(71) Applicants: BIO-RAD EUROPE GMBH, Basel (CH); BIO-RAD LABORATORIES, INC., Hercules, CA (US)

(72) Inventors: Isabelle Batxelli-Molina, Basel (CH); Florian Salipante, Basel (CH); Roger P. Walker, Benicia, CA (US); John Flanagan, Walnut Creek, CA (US); Jeannette Fareh-Michiel, Basel (CH)

(73) Assignee: BIO-RAD LABORATORIES, INC., Hercules, CA (US)

( * ) Notice: Subject to any disclaimer, the term of this patent is extended or adjusted under 35 U.S.C. 154(b) by 86 days.

(21) Appl. No.: 18/502,243

(22) Filed: Nov. 6, 2023

(65) Prior Publication Data

US 2024/0094223 A1 Mar. 21, 2024

Related U.S. Application Data

(63) Continuation of application No. 16/632,404, filed as application No. PCT/US2018/042836 on Jul. 19, 2018, now Pat. No. 11,808,772.

(30) Foreign Application Priority Data

Jul. 19, 2017 (EP) ..................................... 17290092

(51) Int. Cl.
| | |
|---|---|
| *G01N 33/68* | (2006.01) |
| *G16B 25/10* | (2019.01) |

(52) U.S. Cl.
CPC ..... *G01N 33/6893* (2013.01); *G01N 33/6869* (2013.01); *G16B 25/10* (2019.02); *G01N 2333/521* (2013.01); *G01N 2333/5421* (2013.01); *G01N 2333/575* (2013.01); *G01N 2400/40* (2013.01); *G01N 2800/085* (2013.01)

(58) Field of Classification Search
CPC ................................................... C07K 16/24
See application file for complete search history.

(56) References Cited

U.S. PATENT DOCUMENTS

| | | | |
|---|---|---|---|
| 6,631,330 | B1 | 10/2003 | Poynard |
| 7,138,229 | B2 | 11/2006 | Hu et al. |
| 7,824,871 | B2 | 11/2010 | Younossi et al. |
| 7,860,656 | B2 | 12/2010 | Poynard |
| 8,489,335 | B2 | 7/2013 | Cales |
| 9,624,541 | B2 | 4/2017 | Watelet et al. |
| 10,435,744 | B2 | 10/2019 | Watelet et al. |
| 10,976,324 | B2 | 4/2021 | Lambert et al. |
| 11,808,772 | B2 | 11/2023 | Batxelli-Molina et al. |
| 2007/0172907 | A1 | 7/2007 | Volker et al. |
| 2008/0161203 | A1 | 7/2008 | Su et al. |
| 2010/0041069 | A1 | 2/2010 | Lederkremer |
| 2010/0136579 | A1 | 6/2010 | Tseng et al. |
| 2010/0203553 | A1 | 8/2010 | Abdeen et al. |
| 2011/0014126 | A1 | 1/2011 | Evans et al. |
| 2013/0316332 | A1 | 11/2013 | Bieche et al. |
| 2013/0323720 | A1 | 12/2013 | Watelet et al. |
| 2014/0127819 | A1 | 5/2014 | Takahashi et al. |
| 2017/0032099 | A1 | 2/2017 | Cales et al. |
| 2017/0160289 | A1 | 6/2017 | Lambert et al. |
| 2018/0100867 | A1 | 4/2018 | Okanoue et al. |
| 2019/0265241 | A1 | 8/2019 | Poynard |
| 2020/0056235 | A1 | 2/2020 | Watelet et al. |
| 2021/0239713 | A1 | 8/2021 | Lambert et al. |
| 2022/0205039 | A1 | 6/2022 | Watelet et al. |

FOREIGN PATENT DOCUMENTS

| | | |
|---|---|---|
| EP | 2 166 358 | 3/2010 |
| JP | 2013-40923 | 2/2013 |
| WO | WO 02/16949 | 2/2002 |
| WO | WO 2006/082522 | 8/2006 |
| WO | WO 2006/103570 | 10/2006 |
| WO | WO 2007/072290 | 6/2007 |
| WO | WO 2010/000835 | 1/2010 |
| WO | WO 2012/107528 | 8/2012 |
| WO | WO 2012/107530 | 8/2012 |
| WO | WO 2015/197934 | 12/2015 |

OTHER PUBLICATIONS

Stratagene Catalog, 1988, p. 39.*
Anonymous, "Elevated Inflammatory Biomarkers Are Associated With Progression to AIDS and Death despite Viral Suppression" Jan. 1, 2010, 17th Conference on Retroviruses and Opportunistic Infections (CROI 2010), Feb. 16-19, 2010, San Francisco, CA, XP055424021, pp. 1-5, Retrieved from the Internet on Nov. 13, 2017: URL:http://www.hivandhepatitis.com/2010_conference/croi/docs/0309_2010_e.html.
Barsic, N. et al. "Overview and developments in noninvasive diagnosis of nonalcoholic fatty liver disease" *World Journal of Gastroenterology*, Aug. 14, 2012, pp. 3945-3954, vol. 18, Issue 30.

(Continued)

*Primary Examiner* — Prema M Mertz

(74) *Attorney, Agent, or Firm* — SALIWANCHIK, LLOYD & EISENSCHENK

(57) ABSTRACT

The invention provides a method of diagnosing Non-Alcoholic Steatohepatitis (NASH) and/or the hepatic fibrosis status of a subject, especially a subject afflicted with Non-alcoholic fatty liver disease (NAFLD) or NASH, based on the level of only three or more particular biomarkers. The invention further provides a kit suitable for performing said method and the use of said method and methods of treating patients diagnosed in accordance with the disclosed methods.

5 Claims, 13 Drawing Sheets

Figure 1A:
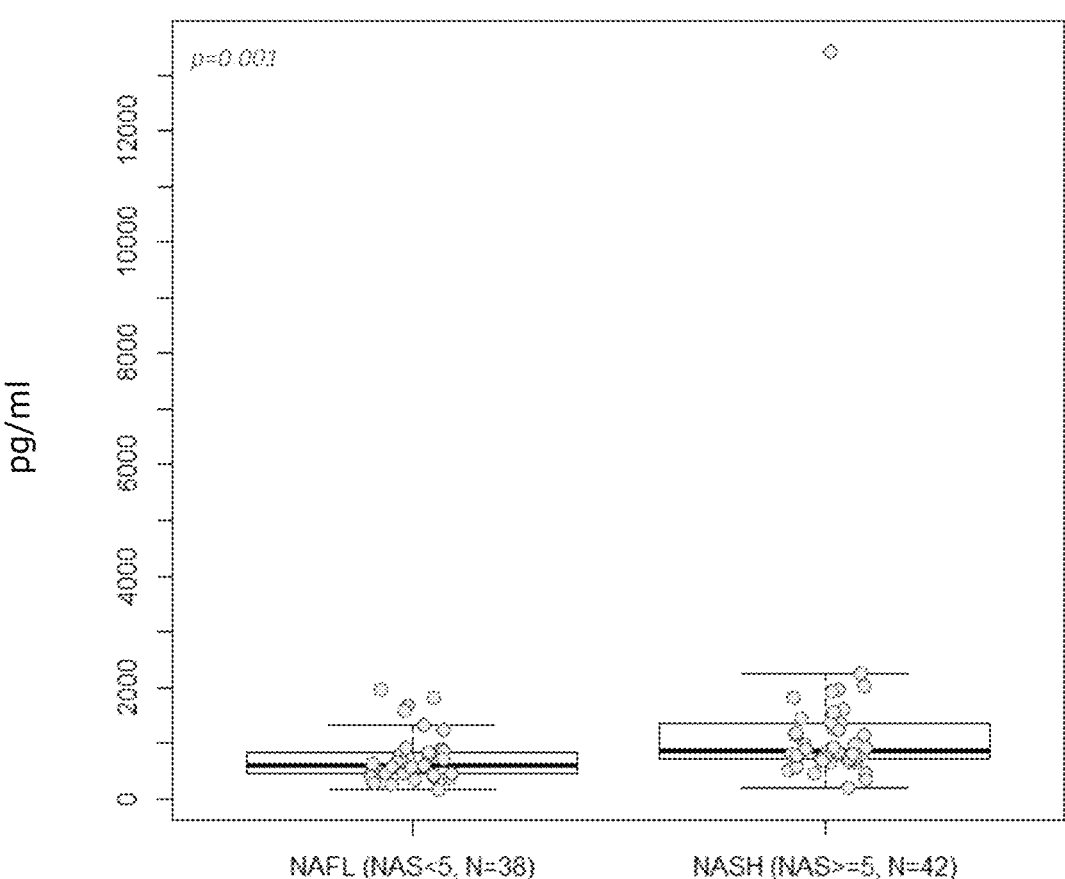

Specification includes a Sequence Listing.

(56)　　　　References Cited

OTHER PUBLICATIONS

Virakul, S. et al. "Histamine induces NF-κB controlled cytokine secretion by orbital fibroblasts via histamine receptor type-1" *Experimental Eye Research,* 2016, pp. 85-93, vol. 147.

Written Opinion in International Application No. PCT/US2018/042836, Sep. 19, 2018, pp. 1-10.

Shin, et al. "SPP1 polymorphisms associated with HBV clearance and HCC occurrence" International Journal of Epidemiology, Oct. 2007, pp. 1001-1008, vol. 36, No. 5.

Schmilovitz-Weiss, H. et al. "Serum globulin levels in predicting the extent of hepatic fibrosis in patients with recurrent post-transplant hepatitis C infection" Clinical Transplantation, May 2007, pp. 391-397, vol. 21, No. 3.

Castera, et al. "Prospective Comparison of Transient Elastography, Fibrotest, APRI, and Liver Biopsy for the Assessment of Fibrosis in Chronic Hepatitis C" *Gastroenterology,* 2005, pp. 343-350, vol. 128.

Shaheen, et al. "FibroTest and FibroScan for the Prediction of Hepatitis C-Related Fibrosis: A Systematic Review of Diagnostic Test Accuracy" *American Journal of Gastroenterology,* 2007, pp. 2589-2600, vol. 102.

Asselah, et al. "Liver gene expression signature to predict response to pegylated interferon plus ribavirin combination therapy in patients with chronic hepatitis C" *Gut,* 2008, pp. 516-524, vol. 57.

Asselah, et al. "Liver Gene Expression Signature of Mild Fibrosis in Patients With Chronic Hepatitis C" Gastroenterology, 2005, pp. 2064-2075, vol. 129.

Bieche, et al. "Molecular profiling of early stage liver fibrosis in patients with chronic hepatitis C virus infection" *Virology,* 2005, pp. 130-144, vol. 332.

Chen, et al. "Cell-Type Specific Gene Expression Signature in Liver Underlies Response to Interferon Therapy in Chronic Hepatitis C Infection" *Gastroenterology,* 2010, pp. 1123-1133, vol. 138.

Huang, et al. "Plasma osteopontin concentration correlates with the severity of hepatic fibrosis and inflammation in HCV-infected subjects" *Clinica Chimica Acta,* 2010, pp. 675-678, vol. 411.

Patouraux, et al. "The Osteopontin Level in Liver, Adipose Tissue and Serum Is Correlated with Fibrosis in Patients with Alcoholic Liver Disease" *PloS ONE,* Apr. 2012, pp. 1-10, vol. 7, No. 4, e35612.

International Search Report for PCT/EP2012/052234 mailed Jun. 25, 2012.

Written Opinion of the International Searching Authority for PCT/EP2012/052234 mailed Jun. 25, 2012.

Gene List, "Human Genome CGH Microarray 44B G4410B" *Agilent Technologies,* 2007.

Ducés, A. et al. "Liver Gene Expression Signature of Mild Fibrosis in Chronic Hepatitis C" *Gastroenterology,* May 2010, p. S-837, vol. 138, No. 5, Supplement 1, Abstract No. T1958.

Ducés, A. et al. "Liver Gene Expression Signature to Predict Response to Pegylated Interferon Plus Ribavirin in Chronic Hepatitis C" *Gastroenterology,* May 2010, p. S-846, vol. 138, No. 5, Supplement 1, Abstract No. T2000.

Ducés, A. et al. "Liver Gene Expression Signature to Predict Response to Pegylated Interferon Plus Ribavirin in Chronic Hepatitis C" *Journal of Hepatology,* Apr. 2010, pp. S266-S267, vol. 52, Supplement 1, Abstract No. 684.

Poster shown at the Meeting of the American of the American Association of the Study of Liver Diseases (AASLD) on Sep. 2, 2010.

French Search Report dated Jan. 31, 2012, issued in connection with FR 1151022.

Claims pending in U.S. Appl. No. 16/553,213, filed Nov. 11, 2019, pp. 1-2.

Seidler, S. et al. "Elevated circulating soluble interleukin-2 receptor in patients with chronic liver diseases is associated with non-classical monocytes" *BMC Gastroenterology,* 2012, pp. 1-8, vol. 12, No. 38.

Abe, T. et al. "CD44 Participates in IP-10 Induction in Cells in Which Hepatitis C Virus RNA Is Replicating, through an Interaction with Toll-Like Receptor 2 and Hyaluronan" *Journal of Virology,* Jun. 2012, pp. 6159-6170, vol. 86, No. 11.

Mak, T.-M. et al. "Liver Fibrosis Assessment Using Transient Elastography Guided With Real-Time B-Mode Ultrasound Imaging: A Feasibility Study" *Ultrasound in Med. & Biol.,* 2013, pp. 956-966, vol. 39, No. 6.

Micheloud, D. et al. "Serum Levels of Fibrosis Progression Biomarkers Measured Early After LT are Associated to Severe HCV Recurrence" *Hepatology,* Oct. 2007, p. 476A, Aasid Abstract #536, vol. 46, No. 4.

Patel, K. et al. "Multiplex Protein Analysis to Determine Fibrosis Stage and Progression in Patients With Chronic Hepatitis C" *Clinical Gastroenterology and Hepatology,* 2014, pp. 2113-2120 and 2120e1-e3, vol. 12, No. 12.

El Raziky, M. et al. "A Novel Prediction Model for Liver Fibrosis in Patients With Chronic Hepatitis C Virus Using Fibroscan and Routine Laboratory Data" *Journal of Hepatology,* 2013, Poster #450, p. S184, vol. 58.

Wu, Y.-M. et al. "A simple noninvasive index to predict significant liver fibrosis in patients with advanced schistosomiasis japonica" *Parasitology International,* 2013, pp. 283-288, vol. 62.

Written Opinion in International Application No. PCT/FR2015/051518, Aug. 14, 2015, pp. 1-8.

Abd El-Kader, S.M. et al. "Non-alcoholic fatty liver disease: The diagnosis and management" *World J Hepatol.,* Apr. 28, 2015, pp. 846-858, vol. 7, No. 6.

Vernon, G. et al. "Systematic review: the epidemiology and natural history of non-alcoholic fatty liver disease and non-alcoholic steatohepatitis in adults" *Aliment Pharmacol Ther,* 2011, pp. 274-285, vol. 34.

Hashimoto, E. et al. "Characteristics and diagnosis of NAFLD/NASH" *J Gastroenterol Hepatol,* 2013, pp. 64-70, vol. 28, Suppl 4.

Angulo, P. et al. "Non-alcoholic fatty liver disease" *J Gastroenterol Hepatol,* 2002, pp. S186-S190, vol. 17.

Beymer, C. et al. "Prevalence and Predictors of Asymptomatic Liver Disease in Patients Undergoing Gastric Bypass Surgery" *Arch Surg,* Nov. 2003, pp. 1240-1244, vol. 138.

Crespo, J. et al. "Are there Predictive Factors of Severe Liver Fibrosis in Morbidly Obese Patients with Non-alcoholic Steatohepatitis?" *Obesity Surgery,* 2001, pp. 254-257, vol. 11.

Dixon, J.B. et al. "Nonalcoholic Fatty Liver Disease: Predictors of Nonalcoholic Steatohepatitis and Liver Fibrosis in the Severely Obese" *Gastroenterology,* Jul. 2001, pp. 91-100, vol. 121, No. 1.

Gholam, P.M. et al. "Liver Pathology in Morbidly Obese Patients Undergoing Roux-en-Y Gastric Bypass Surgery" *Obesity Surgery,* 2002, pp. 49-51, vol. 12.

Moretto, M. et al. "Hepatic Steatosis In Patients Undergoing Bariatric Surgery and its Relationship to Body Mass Index and Co-Morbidities" *Obesity Surgery,* 2003, pp. 622-624, vol. 13.

Hsiao, P.-J. et al. "Significant correlations between severe fatty liver and risk factors for metabolic syndrome" *J Gastroenterol Hepatol,* 2007, pp. 2118-2123, vol. 22.

Fracanzani, A.L. et al. "Risk of Severe Liver Disease in Nonalcoholic Fatty Liver Disease with Normal Aminotransferase Levels: A Role for Insulin Resistance and Diabetes" *Hepatology,* Sep. 2008, pp. 792-798, vol. 48, No. 3.

Angulo, P. et al., "Independent Predictors of Liver Fibrosis in Patients With Nonalcoholic Steatohepatitis" *Hepatology,* Dec. 1999, pp. 1356-1362, vol. 30, No. 6.

Chalasani, N. et al. "The Diagnosis and Management of Non-alcoholic Fatty Liver Disease: Practice Guideline by the American Gastroenterological Association, American Association for the Study of Liver Diseases, and American College of Gastroenterology" *Gastroenterology,* Jun. 2012, pp. 1592-1609, vol. 142, No. 7.

European Association for the Study of the Liver, et al. "EASL-EASD-EASO Clinical Practice Guidelines for the Management of Non-Alcoholic Fatty Liver Disease" *Obes Facts,* 2016, pp. 65-90, vol. 9, No. 2.

Chalasani, N. et al. "The Diagnosis and Management of Non-alcoholic Fatty Liver Disease: Practice Guideline by the American Association for the Study of Liver Diseases, American College of

(56)            References Cited

OTHER PUBLICATIONS

Gastroenterology, and the American Gastroenterological Association" *Am J Gastroenterol,* Jun. 2012, pp. 811-826, vol. 107.

Farrell, G.C., et al. "Guidelines for the assessment and management of non-alcoholic fatty liver disease in the Asia-Pacific region: Executive summary" *J Gastroenterol Hepatol,* 2007, pp. 775-777, vol. 22.

Ratziu, V. et al. "A position statement on NAFLD/NASH based on the EASL 2009 special conference" *J Hepatol,* 2010, pp. 372-384, vol. 53.

Sanyal, A.J. et al. "AGA Technical Review on Nonalcoholic Fatty Liver Disease" *Gastroenterology,* Nov. 2002, pp. 1705-1725, vol. 123, No. 5.

Bedossa, P. et al. "Utility and Appropriateness of the Fatty Liver Inhibition of Progression (FLIP) Algorithm and Steatosis, Activity, and Fibrosis (SAF) Score in the Evaluation of Biopsies of Nonalcoholic Fatty Liver Disease" *Hepatology,* Aug. 2014, pp. 565-575, vol. 60, No. 2.

Kleiner, D.E. et al. "Nonalcoholic Fatty Liver Disease: Pathologic Patterns and Biopsy Evaluation in Clinical Research" *Semin Liver Dis,* 2012, pp. 3-13, vol. 32, No. 1.

Kleiner, D.E. et al. "Design and Validation of a Histological Scoring System for Nonalcoholic Fatty Liver Disease" *Hepatology,* Jun. 2005, pp. 1313-1321, vol. 41, No. 6.

Ratziu, V. et al. "Sampling Variability of Liver Biopsy in Nonalcoholic Fatty Liver Disease" *Gastroenterology,* Jun. 2005, pp. 1898-1906, vol. 128, No. 7.

Vuppalanchi, R. et al. "Nonalcoholic Fatty Liver Disease and Nonalcoholic Steatohepatitis: Selected Practical Issues in Their Evaluation and Management" *Hepatology,* Jan. 2009, pp. 306-317, vol. 49, No. 1.

Vuppalanchi, R. et al. "Non-alcoholic fatty liver disease and nonalcoholic steatohepatitis: Selected practical issues in their evaluation and management" *Hepatology,* Jan. 2009, pp. 1-23, author manuscript.

Musso, G. et al. "Meta-analysis: Natural history of non-alcoholic fatty liver disease (NAFLD) and diagnostic accuracy of non-invasive tests for liver disease severity" *Ann Med,* 2011, pp. 617-649, vol. 43, No. 8.

Ryan, M.C. et al. "Associations Between Liver Histology and Severity of the Metabolic Syndrome in Subjects With Nonalcoholic Fatty Liver Disease" *Diabetes Care,* May 2005, pp. 1222-1224, vol. 28, No. 5.

Marchesini, G. et al. "Nonalcoholic Fatty Liver, Steatohepatitis, and the Metabolic Syndrome" *Hepatology,* Apr. 2003, pp. 917-923, vol. 37, No. 4.

Bedogni, G. et al. "The Fatty Liver Index: a simple and accurate predictor of hepatic steatosis in the general population" *BMC Gastroenterol,* Nov. 2006, pp. 1-7, vol. 6, No. 33.

Lee, J.-H. et al. "Hepatic steatosis index: A simple screening tool reflecting nonalcoholic fatty liver disease" *Dig Liver Dis,* 2010, pp. 503-508, vol. 42.

Poynard, T. et al., "The diagnostic value of biomarkers (SteatoTest) for the prediction of liver steatosis" *Comp Hepatol,* 2005, pp. 1-14, vol. 4, No. 10.

Fedchuk, L. et al. "Performance and limitations of steatosis biomarkers in patients with nonalcoholic fatty liver disease" *Aliment Pharmacol Ther,* 2014, pp. 1209-1222, vol. 40.

Fishbein, M. et al. "Hepatic MRI for Fat Quantitation: Its Relationship to Fat Morphology, Diagnosis, and Ultrasound" *J Clin Gastroenterol,* Aug. 2005, pp. 619-625, vol. 39, No. 7.

Saadeh, S. et al. "The Utility of Radiological Imaging in Nonalcoholic Fatty Liver Disease" *Gastroenterology,* Sep. 2002, pp. 745-750, vol. 123, No. 3.

Angulo, P. et al. "The NAFLD Fibrosis Score: A Noninvasive System That Identifies Liver Fibrosis in Patients with NAFLD" *Hepatology,* Apr. 2007, pp. 846-854, vol. 45, No. 4.

Boursier, J. et al. "Diagnostic accuracy and prognostic significance of blood fibrosis tests and liver stiffness measurement by FibroScan in non-alcoholic fatty liver disease" *J Hepatol,* 2016, pp. 570-578, vol. 65.

Koplay, M. et al. "Importance of imaging and recent developments in diagnosis of nonalcoholic fatty liver disease" *World J Hepatol,* Apr. 18, 2015, pp. 769-776, vol. 7, No. 5.

Castera, L. et al. "Pitfalls of Liver Stiffness Measurement: A 5-Year Prospective Study of 13,369 Examinations" *Hepatology,* Mar. 2010, pp. 828-835, vol. 51, No., 3.

Wong, V. W-S. et al. "Diagnosis of Fibrosis and Cirrhosis Using Liver Stiffness Measurement in Nonalcoholic Fatty Liver Disease" *Hepatology,* Feb. 2010, pp. 454-462, vol. 51, No. 2.

Wong, V. W-S. et al. "Liver Stiffness Measurement Using XL Probe in Patients With Nonalcoholic Fatty Liver Disease" *Am J Gastroenterol,* Dec. 2012, pp. 1862-1871, vol. 107.

Tilg, H. "Adipocytokines in Nonalcoholic Fatty Liver Disease: Key Players Regulating Steatosis, Inflammation and Fibrosis" *Curr Pharm Des,* 2010, pp. 1893-1895, vol. 16, No. 17.

Jamali, R. et al. "Serum adipokines might predict liver histology findings in non-alcoholic fatty liver disease" *World J Gastroenterol,* Jun. 7, 2016, pp. 5096-5103, vol. 22, No. 21.

Cusi, K. et al. "Limited value of plasma cytokeratin-18 as a biomarker for NASH and fibrosis in patients with non-alcoholic fatty liver disease" *J Hepatol,* 2014, pp. 167-174, vol. 60.

Grigorescu, M. et al. "A novel pathophysiological-based panel of biomarkers for the diagnosis of nonalcoholic steatohepatitis" *J Physiol Pharmacol,* 2012, pp. 347-353, vol. 63, No. 4.

Pirvulescu, I. et al. "Noninvasive Clinical Model for the Diagnosis of Nonalcoholic Steatohepatitis in Overweight and Morbidly Obese Patients undergoing Bariatric Surgery" *Chirurgia,* 2012, pp. 772-779, vol. 107, No. 6.

Polyzos, S.A. et al. "Adipokines in nonalcoholic fatty liver disease" *Metabolism,* 2016, pp. 1062-1079, vol. 65.

Larter, C.Z. et al. "A fresh look at NASH pathogenesis. Part 1: The metabolic movers" *J Gastroenterol Hepatol,* 2010, pp. 672-690, vol. 25.

Park, S.H. et al. "Body Fat Distribution and Insulin Resistance: Beyond Obesity in Nonalcoholic Fatty Liver Disease among Overweight Men" *J Am Coll Nutr,* 2007, pp. 321-326, vol. 26, No. 4.

Park, B.J. et al. "Visceral adipose tissue area is an independent risk factor for hepatic steatosis" *J Gastroenterol Hepatol,* 2008, pp. 900-907, vol. 23.

Harris, R.B.S. et al., "Location, Location, Location . . ." *Cell Metab,* May 2008, pp. 359-361, vol. 7.

Zhang, X. et al., "CXCL10 plays a key role as an inflammatory mediator and a non-invasive biomarker of non-alcoholic steatohepatitis" *J Hepatol,* 2014, pp. 1365-1375, vol. 61.

Du Plessis, J. et al. "Association of Adipose Tissue Inflammation With Histologic Severity of Nonalcoholic Fatty Liver Disease" *Gastroenterology,* 2015, pp. 635-648, vol. 149, No. 3, Supplemental Materials pp. e1-e14.

Shah, A.G. et al. "Comparison of Noninvasive Markers of Fibrosis in Patients With Nonalcoholic Fatty Liver Disease" *Clin Gastroenterol Hepatol,* Oct. 2009, pp. 1104-1112, vol. 7, No. 10.

Angulo, P. et al. "Simple Noninvasive Systems Predict Long-term Outcomes of Patients With Nonalcoholic Fatty Liver Disease" *Gastroenterology,* Oct. 2013, pp. 1-17, vol. 145, No. 4.

Yoneda, M. et al. "Noninvasive scoring systems in patients with nonalcoholic fatty liver disease with normal alanine aminotransferase levels" *J Gastroenterol,* 2013, pp. 1051-1060, vol. 48.

Brunt, E.M. et al. "Nonalcoholic Steatohepatitis: A Proposal for Grading and Staging the Histological Lesions" *Am J Gastroenterol,* 1999, pp. 2467-2474, vol. 94, No. 9.

Castera, L. et al. "Non-invasive evaluation of liver fibrosis using transient elastography" *J Hepatol,* 2008, pp. 835-847, vol. 48.

Imbert-Bismut, F. et al. "Biochemical markers of liver fibrosis in patients with hepatitis C virus infection: a prospective study" *Lancet,* Apr. 7, 2001, pp. 1069-1075, vol. 357, No. 9262.

Adams, L.A. et al. "Hepascore: An Accurate Validated Predictor of Liver Fibrosis in Chronic Hepatitis C Infection" *Clin Chem,* 2005, pp. 1867-1873, vol. 51, No. 10.

(56) References Cited

OTHER PUBLICATIONS

Forns, X. et al. "Identification of Chronic Hepatitis C Patients Without Hepatic Fibrosis by a Simple Predictive Model" *Hepatology,* Oct. 2002, pp. 986-992, vol. 36, No. 4.

Wai, C-T. et al. "A Simple Noninvasive Index Can Predict Both Significant Fibrosis and Cirrhosis in Patients With Chronic Hepatitis C" *Hepatology,* Aug. 2003, pp. 518-526, vol. 38, No. 2.

Sterling, R.K. et al. "Development of a Simple Noninvasive Index to Predict Significant Fibrosis in Patients With HIV/HCV Coinfection" *Hepatology,* Jun. 2006, pp. 1317-1325, vol. 43, No. 6.

Flanagan, J.J. et al. "Development of monoclonal antibodies to pre-haptoglobin 2 and their use in an enzyme-linked immunosorbent assay (ELISA)" *J Immunol Methods,* 2014, pp. 34-42, vol. 406.

Team, R.C., *R: A language and environment for statistical computing. R Foundation for Statistical Computing,* Vienna, Austria, http://www.R-project.org/, 2015, pp. 1-16.

Benjamini, Y. et al. "Controlling the False Discovery Rate: a Practical and Powerful Approach to Multiple Testing" *J Roy Statist Soc Ser B,* 1995, pp. 289-300, vol. 57, No. 1.

Youden, W.J. "Index for Rating Diagnostic Tests" Cancer, Jan. 1950, pp. 32-35.

Hastie, T. et al. "The Elements of Statistical Learning: Data Mining, Inference, and Prediction" Springer Science & Business Media, 2001, pp. 1-764.

Irvine, K. M. et al. "Multiplex Serum Protein Analysis Identifies Novel Biomarkers of Advanced Fibrosis in Patients with Chronic Liver Disease with the Potential to Improve Diagnostic Accuracy of Established Biomarkers" *PLoS ONE,* Nov. 18, 2016, pp. 1-13, vol. 11, No. 11, e0167001.

Zhou, J-H. et al. "Autoantibodies against MMP-7 as a novel diagnostic biomarker in esophageal squamous cell carcinoma" *World Journal of Gastroenterology,* Mar. 14, 2011, pp. 1373-1378, vol. 17, No. 10.

Xie, W. et al. "Anti-POSTN and Anti-TIMP1 Autoantibodies as Diagnostic Markers in Esophageal Squamous Cell Carcinoma" *Frontiers in Genetics,* Apr. 2022, pp. 1-11, vol. 13, Article 860611.

Liao, C-C. et al. "Isotypes of autoantibodies against differentially expressed novel malondialdehyde-modified peptide adducts in serum of Taiwanese women with rheumatoid arthritis" *Journal of Proteomics,* 2018, pp. 1-12, vol. 170.

* cited by examiner

CXCL10

IL-8

SEQUENCE LISTING

```
Sequence total quantity: 1
SEQ ID NO: 1          moltype = AA  length = 16
FEATURE               Location/Qualifiers
REGION                1..16
                      note = synthetic
source                1..16
                      mol_type = protein
                      organism = synthetic construct
SEQUENCE: 1
MRDSSPLVHY GWGDPI                                                  16
```

BIOMARKER COMBINATIONS TO SIMULTANEOUSLY EVALUATE NON-ALCOHOLIC STEATOHEPATITIS AND HEPATIC FIBROSIS STATUS

CROSS-REFERENCE TO RELATED APPLICATIONS

This application is a continuation of U.S. application Ser. No. 16/632,404, filed Jan. 20, 2020, now U.S. Pat. No. 11,808,772, which is the U.S. national stage application of International Patent Application No. PCT/US2018/042836, filed Jul. 19, 2018.

The Sequence Listing for this application is labeled "Seq-List.xml" which was created on Nov. 6, 2023 and is 2,414 bytes. The entire content of the sequence listing is incorporated herein by reference in its entirety.

The invention provides a method of diagnosing Non-Alcoholic Steatohepatitis (NASH) and/or the hepatic fibrosis status of a subject, especially a subject afflicted with Non-alcoholic fatty liver disease (NAFLD) or NASH, based on the level of only 3 or more particular biomarkers and, optionally, treating a subject diagnosed with NASH. The invention further provides a kit suitable for performing said method and the use of said method.

BACKGROUND OF THE INVENTION

Non-alcoholic fatty liver disease (NAFLD) is considered to be the hepatic manifestation of metabolic syndrome. NAFLD has become an important public health issue because of its worldwide prevalence. According to data from annual health check-ups, NAFLD is now the most frequent chronic liver disease that occurs across all age groups and in 14-30% of the general population (Abd El-Kader, S. M. and E. M. El-Den Ashmawy, World J Hepatol, 2015. 7(6):846-58). NAFLD is the most common liver disorder in Western countries affecting 17-46% of adults, with differences according to the diagnostic method, age, sex and ethnicity (Vernon, G., A. Baranova, and Z. M. Younossi, Aliment Pharmacol Ther, 2011. 34(3):274-85). NAFLD includes two pathologically distinct conditions with different prognoses: non-alcoholic fatty liver (NAFL) and non-alcoholic steato-hepatitis (NASH). NASH is observed in 10-20% of cases of NAFLD, while the estimated prevalence of NASH is 1-8% (Hashimoto, E., M. Taniai, and K. Tokushige, J Gastroenterol Hepatol, 2013. 28 Suppl 4:64-70).

NAFL is defined as either excessive fat accumulation in the liver with more than 5% of hepatocytes containing visible intracellular triglycerides or steatosis affecting at least 5% of the liver volume or weight in patients consuming less than 30 g (three units) of alcohol per day for men and less than 20 g (two units) of alcohol per day for women (Abd El-Kader, S. M. and E. M. El-Den Ashmawy, World J Hepatol, 2015. 7(6):846-58). NASH is a form of metabolic liver disease in which fatty change (steatosis) is associated with lobular inflammation and hepatocyte injury with or without hepatic fibrosis. It is typically asymptomatic leading however to severe liver injuries such as cirrhosis and hepatocarcinoma.

Obesity is the most important risk factor for NAFL with a prevalence of NAFLD 4.6 times greater in the obese population, and up to 74% of obese individuals have fatty livers (Angulo, P. and K. D. Lindor, J Gastroenterol Hepatol, 2002. 17 Suppl:S186-90). Among morbidly obese patients undergoing bariatric surgery for weight loss, 84% to 96% have NAFL and 2% to 12% have severe fibrosis or cirrhosis (Angulo, P. and K. D. Lindor, J Gastroenterol Hepatol, 2002. 17 Suppl:S186-90; Beymer, C., et al., Arch Surg, 2003. 138(11):1240-4; Crespo, J., et al., Obes Surg, 2001. 11(3): 254-7; Dixon, J. B., P. S. Bhathal, and P. E. O'Brien, Gastroenterology, 2001. 121(1):91-100; Gholam, P. M., D. P. Kotler, and L. J. Flancbaum, Obes Surg, 2002. 12(1):49-51); the degree of steatosis was found to be correlated with body mass index (BMI) (Moretto, M., et al., Obes Surg, 2003. 13(4):622-4; Hsiao, P. J., et al., J Gastroenterol Hepatol, 2007. 22(12):2118-23). NAFL is also present in 5 to 29% of lean persons with or without associative risk factors, more frequently in females, at a younger age and with normal liver enzymes. Their liver disease may nonetheless be progressive (Fracanzani, A. L., et al., Hepatology, 2008. 48(3):792-8; Angulo, P., et al., Hepatology, 1999. 30(6):1356-62).

The need for NAFLD screening in the community has been questioned given the high direct and indirect costs of testing, the low predictive value of non-invasive existing tests, the risks associated with liver biopsy and the lack of effective treatments (Chalasani, N., et al., Gastroenterology, 2012. 142(7):1592-609). However, the progressive form of NAFLD (i.e. NASH), particularly when associated with advanced fibrosis, should be identified in patients at risk (age>50 years, type 2 diabetes mellitus or metabolic syndrome) to improve liver-related outcomes and to decrease the associated mortality rate (European Association for the Study of the Liver, Obes Facts, 2016. 9(2):65-90).

NAFL/NASH Diagnosis

The diagnosis of NAFL is based on the presence of the following three criteria: non-alcoholic status, detection of steatosis >5% either by imaging or by histology, and appropriate exclusion of other liver diseases such as alcoholic fatty liver disease (AFLD), drug-induced fatty liver disease, HCV-associated fatty liver disease (genotype 3), autoimmune hepatitis, coeliac disease and Wilson's disease (European Association for the Study of the Liver, Obes Facts, 2016. 9(2):65-90; Chalasani, N., et al., Am J Gastroenterol, 2012. 107(6):811-26; Farrell, G. C., et al., J Gastroenterol Hepatol, 2007. 22(6):775-7; Ludwig, J., et al., Mayo Clin Proc, 1980. 55(7):434-8; Ratziu, V., et al., J Hepatol, 2010. 53(2):372-84; Sanyal, A. J. and A. Gastroenterology, 2002. 123(5):1705-25). NASH, the progressive form of NAFLD is histologically diagnosed based on the joint presence of steatosis, ballooning and lobular inflammation with or without fibrosis. Other commonly observed features include Mallory's hyaline, vacuolated nuclei in periportal hepatocytes, lobular lipogranulomas, periodic acid-Schiff (PAS)-diastase-resistant Kupffer cells and pericellular fibrosis (in those with advanced stages of fibrosis or cirrhosis) (Bedossa, P. and F. P. Hepatology, 2014. 60(2):565-75; Kleiner, D. E. and E. M. Brunt, Semin Liver Dis, 2012. 32(1):3-13; Kleiner, D. E., et al., Hepatology, 2005. 41(6):1313-21). Liver biopsy is essential for the diagnosis of NASH and is the only procedure that reliably differentiates between NAFL and NASH. Biopsy evaluation is considered as "the gold standard" for a definitive diagnosis. However, liver biopsy has several drawbacks; it is an expensive and invasive procedure and is fraught with the possibility of sampling error with potential high variability in pathologist's interpretation (Ratziu, V., et al., Gastroenterology, 2005. 128(7):1898-906). Moreover, given the extremely high prevalence of NAFLD, a liver biopsy would be poorly suited as a screening test for NASH in the general population.

Serum aminotransferase levels and imaging tests such as ultrasounds, computed tomography, and magnetic resonance do not reliably assess specifically steatohepatitis and fibrosis in patients with NAFLD. Therefore, there has been significant interest in developing clinical prediction rules and non-invasive biomarkers for identifying steatohepatitis in patients with NAFLD. The presence of metabolic syndrome is a strong predictor for the presence of NASH and may be used to better identify patients with persistently abnormal liver biochemistries who would benefit from a liver biopsy (Vuppalanchi, R. and N. Chalasani, Hepatology, 2009. 49(1):306-17; Musso, G., et al., Ann Med, 2011. 43(8):617-49; Ryan, M. C., et al., Diabetes Care, 2005. 28(5):1222-4; Marchesini, G., et al., Hepatology, 2003. 37(4):917-23).

Various indices have been proposed for diagnosing fatty change of the liver including the fatty liver index (FLI) (Bedogni, G., et al., BMC Gastroenterol, 2006. 6:33), NAFLD liver fat score, hepatic steatosis index (HIS) (Lee, J. H., et al., Dig Liver Dis, 2010. 42(7):503-8), and SteatoTest (ST) (Poynard, T., et al., Comp Hepatol, 2005. 4:10). They have all been externally validated in the general population or in grade 3 obese persons and variably predict metabolic, hepatic and cardiovascular outcomes/mortality. These scores are associated with insulin-resistance (IR) and predict the presence, not the severity of steatosis (Fedchuk, L., et al., Aliment Pharmacol Ther, 2014. 40(10):1209-22). Several imaging techniques have also been proposed as non-invasive diagnostic tests for NAFLD (Koplay, M., et al., World J Hepatol, 2015. 7(5):769-76). Ultrasonography has limited sensitivity and does not reliably detect steatosis when <20% (Fishbein, M., et al., J Clin Gastroenterol, 2005. 39(7):619-25; Saadeh, S., et al., Gastroenterology, 2002. 123(3):745-50). Ultrasonography is the preferred first-line diagnostic procedure for imaging of NAFLD. Whenever imaging tools are not available or feasible, serum biomarkers and scores are an acceptable alternative for the diagnosis of steatosis (European Association for the Study of the Liver, Obes Facts, 2016. 9(2):65-90). To date, no non-invasive test has been validated for the diagnosis of NASH and the gold standard remains liver biopsy reporting steatosis, hepatocyte ballooning and lobular inflammation with or without fibrosis.

Non-invasive assessment of advanced fibrosis in NAFLD is possible by using several biomarkers and scoring systems. The NAFLD Fibrosis Score (NFS) is a widely validated scoring system for predicting the severity of fibrosis that is based on six readily assessable clinical variables (age, Body Mass Index (BMI), hyperglycemia, platelet count, albumin and Aspartate Aminotransferase (AST)/Alanine Aminotransferase (ALT) ratio (Angulo, P., et al., Hepatology, 2007. 45(4):846-54). As described in a recent study comparing nine non-invasive tests, many serum biomarkers have shown acceptable diagnostic accuracy as defined by their area under the receiver operating characteristic curve (AUROC) >0.8 (i.e., Hepascore®, FibroMeter-NAFLD®) (Boursier, J., et al., J Hepatol, 2016. 65(3):570-8). Liver stiffness measurement (LSM) by transient elastography (Fibro-Scan®) has shown promising results for assessment of liver fibrosis, with better performances for cirrhosis than advanced fibrosis. However, these modalities remain expensive, not widely available and yield unreliable results in the presence of high BMI and/or thoracic fold thickness. In a large, unselected, European series, up to 20% of examinations had unreliable results (Castera, L., et al., Hepatology, 2010. 51(3):828-35), mainly in obese patients with NAFLD (Wong, V. W., et al., Hepatology, 2010. 51(2):454-62). The XL probe of Fibroscan® (compatible with obese patients) should be used in these patients to reduce the failure rate, which remains high (35%) (Wong, V. W., et al., Am J Gastroenterol, 2012. 107(12):1862-71).

Biological Processes and Key Molecules Involved in NASH

The pathogenesis of NAFLD is thought to be related mainly with IR syndrome and oxidative stress; the latter resulting from mitochondrial fatty acid oxidation and nuclear factor-kappaB (NFkappaB) dependent inflammatory cytokine expression. Further, adipocytokines may promote hepatocellular damage, inflammation, fibrosis and progressive liver disease (Polyzos, S. A., J. Kountouras, and C. Zavos, Curr Mol Med, 2009. 9(3):299-314; Tilg, H., Curr Pharm Des, 2010. 16(17):1893-5). Adipocytokines and other recognized cytokines produced partially by inflammatory cells infiltrating adipose tissue, has been reported to play an important role in the pathogenesis of IR and NAFLD, through complex and interactive paracrine and endocrine mechanisms (Schaffler, A., J. Scholmerich, and C. Buchler, Nat Clin Pract Gastroenterol Hepatol, 2005. 2(6):273-80). The association between NAFLD, circulating leptin and adiponectin levels is generally well documented: leptin levels increase, whereas adiponectin levels decrease, by increasing the severity of NAFLD (Jamali, R., et al., World J Gastroenterol, 2016. 22(21):5096-103; Cusi, K., et al., J Hepatol, 2014. 60(1):167-74; Grigorescu, M., et al., J Physiol Pharmacol, 2012. 63(4):347-53; Pirvulescu, I., et al., Chirurgia (Bucur), 2012. 107(6):772-9). Data regarding other adipokines in histologically confirmed NAFLD populations are inconclusive (Polyzos, S. A., J. Kountouras, and C. S. Mantzoros, Metabolism, 2015). Inflammation is a critical response to tissue damage or infection in which secreted mediators such as cytokines and chemokines coordinate cellular defenses and tissue repair. Since this is generally a whole body response, it is possible that inflammation affecting or infiltrating the liver in NASH may originate outside the liver. One site of interest is the adipose tissue, particularly the visceral adipose tissue which is expanded in NAFLD (Larter, C. Z., et al., J Gastroenterol Hepatol, 2010. 25(4):672-90; Park, S. H., et al., J Am Coll Nutr, 2007. 26(4):321-6; Park, B. J., et al., J Gastroenterol Hepatol, 2008. 23(6):900-7). Visceral adipose tissue is inherently pro-inflammatory (Harris, R. B. and R. L. Leibel, Cell Metab, 2008. 7(5):359-61), but inflammation also occurs in stressed, de-differentiated subcutaneous adipose tissue in obesity. Important consequences include the release of macrophage chemokines, cytokines and interleukins notably C-X-C motif chemokine 10 (CXCL10 or IP10), Interleukin 8 (IL-8), macrophage chemotactic protein 1 (MCP-1), tumor necrosis factor-α (TNF-α) and interleukin-1β (IL-1β) (Zhang, X., et al., J Hepatol, 2014. 61(6):1365-75; du Plessis, J., et al., Gastroenterology, 2015. 149(3):635-48 e14). There is increasing evidence that visceral adipose tissue could be a causative risk factor for fatty liver and NASH. Markers of liver fibrosis may help predict the evolutionary course of NAFLD. Several non-invasive markers of fibrosis have been used in NAFLD scores, including NAFLD fibrosis score, APRI, FIB-4 score and BARD score. These markers can help to identify patients at highest risk of developing liver-related complications or death (Shah, A. G., et al., Clin Gastroenterol Hepatol, 2009. 7(10):1104-12; Angulo, P., et al., Gastroenterology, 2013. 145(4):782-9 e4; Yoneda, M., et al., J Gastroenterol, 2013. 48(9):1051-60).

Liver fibrosis results from chronic damage to the liver in conjunction with the accumulation of extracellular matrix (ECM) proteins or molecules such as glycosaminoglycans and particularly HA, which is characteristic for most types of chronic liver diseases. HA is a high-molecular-mass polysaccharide found in the ECM, especially of soft connective tissues. It is synthesized in the plasma membrane of fibroblasts and other cells by addition of sugars to the reducing end of the polymer, whereas the nonreducing end protrudes into the pericellular space. HA production increases in proliferating cells and the polymer may play a role in mitosis (Laurent, T. C. et al., FASEB J, 1992. 6(7):2397-404). Haptoglobin is an immunoglobulin-like plasma protein produced by the liver that binds hemoglobin. The haptoglobin-hemoglobin complex is removed from plasma by macrophages and the hemoglobin is catabolized. Haptoglobin is known to scavenge free hemoglobin to inhibit its oxidative activity and increase in serum or plasma haptoglobin concentration occurs as an acute-phase reaction in chronic diseases. HA and haptoglobin are well-known fibrosis and oxidative markers.

The pathogenesis of NASH includes insulin resistance and increased inflammation with deregulated circulating concentrations observed for pro-inflammatory cytokines as for example TNF-α, MCP-1/CCL2, IL-6, IL-10, IL-17 and particularly IL-8. Interleukin-8 (IL-8, CXCL8) is a potent chemoattractant for neutrophils and contributes to acute liver inflammation. Circulating concentrations of chemokines such as CXCL2, CXCL16, CCL5 and particularly CXCL10 are also deregulated (Musso, G. et al., Nature Reviews Drug Discovery, 2016. 15, 249-274). CXCL10 also known as IP-10 or small-inducible cytokine B10 is a cytokine belonging to the CXC chemokine family. CXCL10 binds CXCR3 receptor to induce chemotaxis, apoptosis, cell growth and angiostasis. Alterations in CXCL10 expression levels have been associated with inflammatory diseases including infectious diseases, immune dysfunction and tumor development (Liu, M. et al., Cytokine Growth Factor Rev, 2011. 22(3): 121-130).

The occurrence of NAFLD is strongly linked to obesity, IR and other aspects of the metabolic syndrome and deregulation of adipokines. Deregulated circulating concentrations of hormones implicated in IR, diabetes and obesity have been reported in NASH patients, namely adipokines, leptin and adiponectin and particularly ghrelin. Ghrelin is a small peptide and hormone comprised of 28 amino acids that is mainly produced by the stomach and the pancreas but also the adipose tissue, which stimulates appetite and is a potent stimulator of growth hormone through the action of its receptor, the growth hormone secretagogue receptor. Ghrelin has a unique acylation on the serine in position 3 catalyzed by the ghrelin-ghrelin O-acyltransferase (GOAT) system (Zang, S. R. et al., WJG, 2015. 21(11): 3214-222).

Increased intestinal permeability has been identified as a common underlying mechanism in the pathogenesis of allergic, inflammatory, and autoimmune diseases and is implicated in NAFLD. New research indicates that an early phase of liver injury and inflammation contributes to this breach in the intestinal barrier (Ray, K., Nat. Rev. Gastroenterol. Hepat., 2015. 12(3): 123). A biochemical role for nascent haptoglobin 2 (pre-haptoglobin 2 or pre-HP2) as the only known modulator of intestinal permeability has been established. In addition, elevated levels of serum pre-HP2 have been detected in multiple conditions including coeliac disease and type I diabetes, which are believed to result in part through dysregulation of the intestinal barrier. Pre-HP2 is a biomarker of microbial translocation.

In view of new treatments, expected to be on the market in a few years and which will dramatically change the management of NALFD patients, an accurate diagnosis of NASH and liver fibrosis becomes crucial as liver disease severity determines the patient management: i) NAFL does not need a specialized management because liver lesions are mild with excellent prognosis; ii) early NASH requires a close follow-up because NASH represents the aggressive form of the disease with increased risk of liver fibrosis progression and higher occurrence of diabetes and cardiovascular events; iii) fibrotic NASH requires pharmacological treatment to avoid progression to cirrhosis; iv) cirrhosis highly requires pharmacological treatment to avoid cirrhosis complications and, at this stage, the screening of hepatocellular carcinoma and large oesophageal varices is mandatory.

A model combining non-invasive biomarkers that accurately, rapidly diagnoses NASH patients among patients with NAFLD, metabolic disorders inducing liver lesions such as cardiovascular diseases or diabetes, and which model further predicts the severity of liver fibrosis remains an unmet clinical need.

SHORT DESCRIPTION OF THE INVENTION

It has now been found that a simple non-invasive scoring system (relying on only 3 to 11 or 3 to 12 biomarkers) can be used to diagnose NASH in patients with NAFLD, metabolic disorders inducing liver lesions such as cardiovascular diseases and diabetes and furthermore to discriminate between NASH patients with and without advanced liver fibrosis, i.e. NASH patients with a fibrosis score of F≥3 or F<3, respectively. Subjects diagnosed with NASH can be treated for NASH and/or liver fibrosis, as set forth below.

The invention thus provides two methods for diagnosing Non-Alcoholic Steatohepatitis (NASH). These methods are referred to as "the mathematical model" and "the threshold method". Subjects diagnosed with NASH using either of the two disclosed methods may also be treated as disclosed herein.

The Mathematical Model

The invention thus provides the following method of diagnosing NASH (referred to as "the mathematical model"):

(1) a method of diagnosing Non-Alcoholic Steatohepatitis (NASH), wherein the method comprises:

(I) measuring, in a sample obtained from a subject, levels of at least three biomarkers being a pro-inflammatory cytokine, a chemokine and a glycosaminoglycan contributing to cell-adhesion and tissue modeling;

(II) combining the levels of said at least three biomarkers measured in step (I) in a mathematical model; and (III) determining whether the subject is afflicted with NASH;

(2) a method comprising steps (I) and (II) as described in (1) above, wherein alternatively or additionally the hepatic fibrosis status of the subject is determined in an alternative or additional step (III)'. The method described in (1) and (2), above, may be referred to as "the mathematical model";

(3) a kit for diagnosing NASH and/or the hepatic fibrosis status of a subject, the kit comprising reagents for measuring the levels of the at least three biomarkers as defined in (1) above, and instructions for combining the levels measured in step (I) in a mathematical model and making a decision based on a score obtained from the mathematical model;

(4) the use of the kit as defined in (3) above in a method as defined in (1) and/or (2) above; and (5) the treatment of subjects diagnosed with NASH as described in (1) or (2), above.

In a particular embodiment of the method described in (1) or (2), the kit described in (3) or the use described in (4) hereinbefore, NASH diagnosis and/or determination of the hepatic fibrosis status is made in a subject suspected to be afflicted with a liver disease, in particular a NAFLD or NASH or in a subject afflicted with (i.e. who has previously been diagnosed as having) a liver disease, in particular a NAFLD Alternatively, in a particular embodiment, NASH diagnosis and/or determination of the hepatic fibrosis status is made in an obese subject or in a subject afflicted with or suspected to be afflicted with metabolic disorders inducing liver lesions such as cardiovascular diseases or diabetes. In a particular embodiment of the method described in (2), the kit described in (3) or the use described in (4) hereinbefore, the hepatic fibrosis status is determined in a subject afflicted with NASH.

In an additional or alternative embodiment, the pro-inflammatory cytokine is selected from the group consisting of TNF-α, TGF-β1, IL-1, IL-1β, IL-6, IL-8, IL-10, IL-12 and IL-18, preferably IL-8.

In a further additional or alternative embodiment, the chemokine is selected from the group consisting of CXCL8, CXCL9, CXCL10, CCL2, CCL3, CCL4, CCL5, CCL11, preferably CXCL10.

In yet another additional or alternative embodiment, the glycosaminoglycan contributing to cell-adhesion and tissue modeling is selected from the group consisting of hyaluronan or hyaluronic acid or hyaluronate (HA), heparan sulfate, dermatan sulfate, chondroitin sulfate, heparin and keratan sulfate, preferably HA.

In a preferred embodiment, at least the levels of the biomarkers IL-8, CXCL10 and HA are measured.

In a particular embodiment of any of the methods, kit and use described hereinbefore, the level (or value) of one to nine additional biomarkers selected from the group consisting of ghrelin, pre-haptoglobin 2 (pre-HP2), haptoglobin, liver stiffness, age, sex, BMI, hypertension and blood pressure), is measured (or determined).

Hence, in a particular embodiment, at least the levels of four biomarkers are measured in step (I), preferably IL-8, HA, CXCL10 and ghrelin, or
IL-8, HA, CXCL10 and pre-HP2, or
IL-8, HA, CXCL10 and liver stiffness.

In another particular embodiment, at least the levels of five biomarkers are measured in step (I), preferably IL-8, HA, CXCL10, ghrelin and pre-HP2, or
IL-8, HA, CXCL10, ghrelin and liver stiffness or
IL-8, HA, CXCL10, pre-HP2 and liver stiffness.

In another particular embodiment, at least the levels of the biomarkers IL-8, HA, CXCL10, ghrelin, pre-HP2 and liver stiffness are measured in step (I).

In another particular embodiment, at least the levels of the biomarkers IL-8, HA, CXCL10, ghrelin, pre-HP2, hapto-globin, liver stiffness, age, sex, BMI and hypertension (and/or blood pressure) are measured in step (I). In a particular embodiment, the mathematical model used is a mathematical model appropriate for supervised classification for example a mathematical model selected from a Support Vector Machine (SVM), a Random Forest, a decision tree, a mROC, a gradient boosting and a logistic regression, preferably a logistic regression.

In a particularly preferred embodiment of the method described in (1) above, the method comprises:

(I) measuring, in a sample obtained from a subject, levels of at least the biomarkers IL-8, CXCL10 and HA;
(II) combining at least the levels of IL-8, CXCL10 and HA measured in step (I) in a logistic regression formula; and
(III) determining whether the subject is afflicted with NASH. In a particularly preferred embodiment of the method described in (2) above, the method comprises:

(I) measuring, in a sample obtained from a subject, wherein the subject is afflicted with NASH, levels of at least the biomarkers IL-8, CXCL10 and HA;
(II) combining at least the levels of IL-8, CXCL10 and HA measured in step (I) in a logistic regression formula; and
(III)' determining the hepatic fibrosis status of the subject as being either F<3 or F≥3.

The Threshold Method

In an additional embodiment, the invention provides the following method of diagnosing NASH (referred to as "the threshold model"):

(1) a method of diagnosing Non-Alcoholic Steatohepatitis (NASH), wherein the method comprises:
(I) measuring, in a sample obtained from a subject, levels of at least three biomarkers, said biomarkers being a pro-inflammatory cytokine, a chemokine and a gly-cosaminoglycan contributing to cell-adhesion and tissue modeling;
(II) comparing the measured levels of each one of the at least three biomarkers to a particular threshold for each of said at least three biomarkers;
(III) determining whether the subject is afflicted with NASH on the basis of the levels of each one of the at least three biomarkers in comparison to the particular threshold for each of said at least three biomarkers (i.e., the measured level of a particular biomarker is above or below a particular threshold for that biomarker);
(2) a method comprising steps (I), (II) and (III) as described in (1) above, wherein alternatively or additionally the hepatic fibrosis status of the subject is determined in an alternative or additional step (III)'. The method described in (1) and (2), above, may be referred to as "the threshold method";
(3) a kit for diagnosing NASH and/or the hepatic fibrosis status of a subject, the kit comprising reagents for measuring the levels of the at least three biomarkers as defined in (1) above, and instructions for determining and comparing the levels measured in step (I) to threshold levels of the at least three biomarkers and diagnosing the presence of NASH in a subject on the basis of the amounts of biomarkers present is the sample from the subject;
(4) the use of the kit as defined in (3) above in a method as defined in (1) and/or (2) above; and
(5) the treatment of subjects diagnosed with NASH as described in (1) or (2), above.

The pro-inflammatory cytokine measured in the threshold method is selected from the group consisting of TNF-α, TGF-β1, IL-1, IL-1β, IL-6, IL-8, IL-10, IL-12 and IL-18, preferably IL-8. The chemokine measured in the threshold method is selected from the group consisting of CXCL8, CXCL9, CXCL10, CCL2, CCL3, CCL4, CCL5, CCL11, preferably CXCL10. The glycosaminoglycan contributing to cell-adhesion and tissue modeling measured in the threshold method is selected from the group consisting of hyaluronan or hyaluronic acid or hyaluronate (HA), heparan sulfate, dermatan sulfate, chondroitin sulfate, heparin and keratan sulfate, preferably HA. In a preferred embodiment, at least the levels of the biomarkers IL-8, CXCL10 and HA are measured in the threshold method.

In another embodiment as set forth herein, the threshold method measures the level (or value) of one to nine additional biomarkers selected from the group consisting of ghrelin, pre-haptoglobin 2 (pre-HP2), haptoglobin, liver stiffness, age, sex, BMI, hypertension and blood pressure), is measured (or determined) and compared to threshold levels of said one to nine additional biomarkers.

Hence, in a particular embodiment, at least the levels of four biomarkers are measured in step (I) of the threshold method, preferably IL-8, HA, CXCL10 and ghrelin, or IL-8, HA, CXCL10 and pre-HP2, or IL-8, HA, CXCL10 and liver stiffness.

In another particular embodiment, at least the levels of five biomarkers are measured in step (I) of the threshold method, preferably IL-8, HA, CXCL10, ghrelin and pre-HP2, or IL-8, HA, CXCL10, ghrelin and liver stiffness, or IL-8, HA, CXCL10, pre-HP2 and liver stiffness.

In another particular embodiment, at least the levels of the biomarkers IL-8, HA, CXCL10, ghrelin, pre-HP2 and liver stiffness are measured in step (I) of the threshold method.

In another particular embodiment, at least the levels of the biomarkers IL-8, HA, CXCL10, ghrelin, pre-HP2, haptoglobin, liver stiffness, age, sex, BMI and hypertension (and/or blood pressure) are measured in step (I) of the threshold method.

In either of the diagnostic methods described above ("the mathematical model" or "the threshold method"), subjects diagnosed with NASH can be treated for NASH and/or liver fibrosis. In this aspect of the invention, the disclosed diagnostic methods further comprise the treatment of individuals diagnosed with NASH. In certain embodiments, patients diagnosed with NASH by either the mathematical model or the threshold method can be treated by administration of glitazones, such as rosiglitazone or pioglitazone, alone or in combination with Vitamin E; FXR agonists, such as GS-9674, LJN-452, EDP-305, and obeticholic acid; PPAR α and PPAR β (also known as PPARδ) and/or PPAR γ agonists, such as elafibranor, saroglitazar, IVA-337; FGF-19 analogues, such as NGM-282; FGF21 analogues, such as PF-05231023 ((CVX-343), a long-acting FGF21 analog, composed of two molecules of [des-His1, Ala129Cys] FGF21 covalently linked to a humanized IgG$_{1K}$ mAb backbone via a maleimide-azetidinone linker, Giragossian et al., 2015, Drug Metabolism and Disposition, 43(6):803-811, which is hereby incorporated by reference in its entirety); SDD1 inhibitors, such as aramchol, GLP-1 analogues, such as liraglutide, Nor-ursodeoxycholic acid (UDCA); antioxidants, such as Vitamin E; ASK1 inhibitors, such as GS-4997; VAP-1 inhibitors, such as PXS-4728A; CCR2/CCR5 antagonists, such as cenicriviroc; pentamidines, such as VLX-103; caspase inhibitors, such as emricasan; LOXL2 inhibitors, such as simtuzumab; and/or falectin-3 protein inhibitors, such as galactoarabino rhamnogalacturonate (GR-MD-02) or any other treatment disclosed in Friedman et al., 2018, Mechanisms of NAFLD development and therapeutic strategies, Nature Medicine, 24:908-922, which is hereby incorporated by reference in its entirety. Other treatments for individuals diagnosed with NASH using the mathematical model or the threshold method are described in Tables 10 and 11.

SHORT DESCRIPTION OF THE FIGURES

Figure 1B:
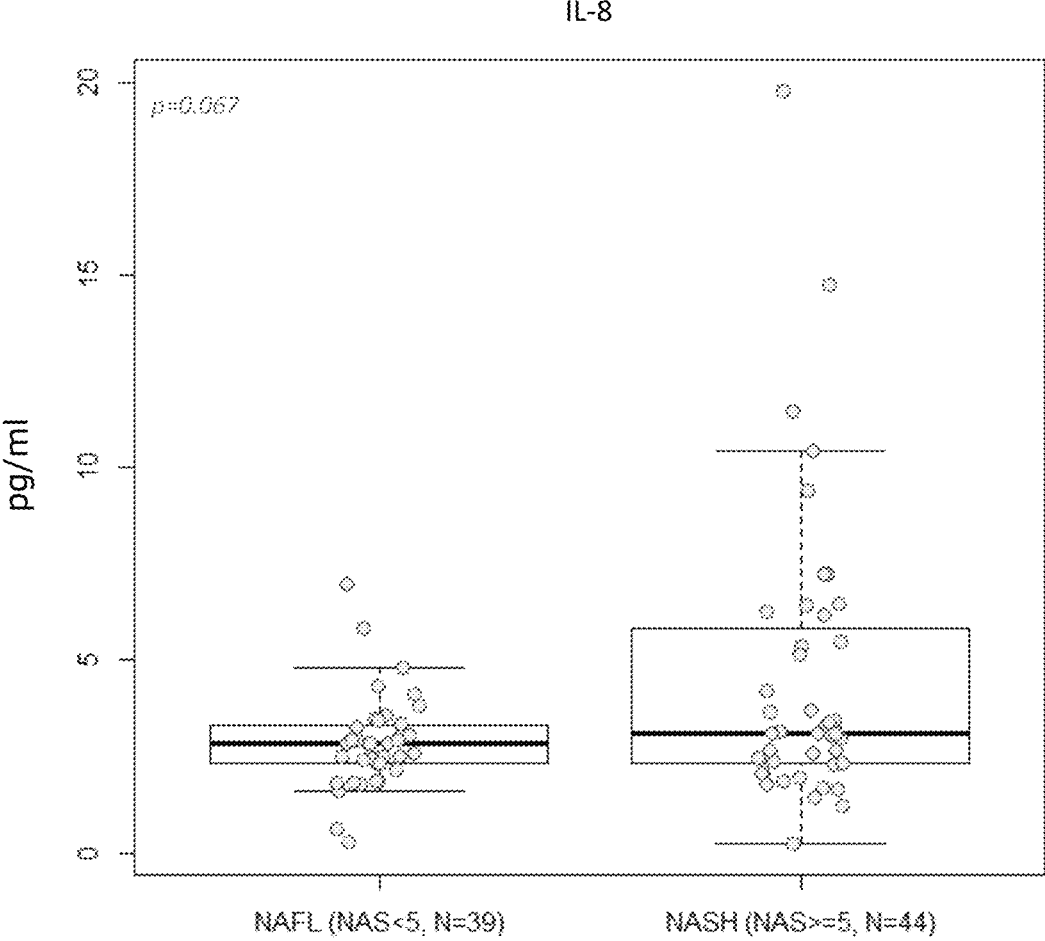
Figure 1C:
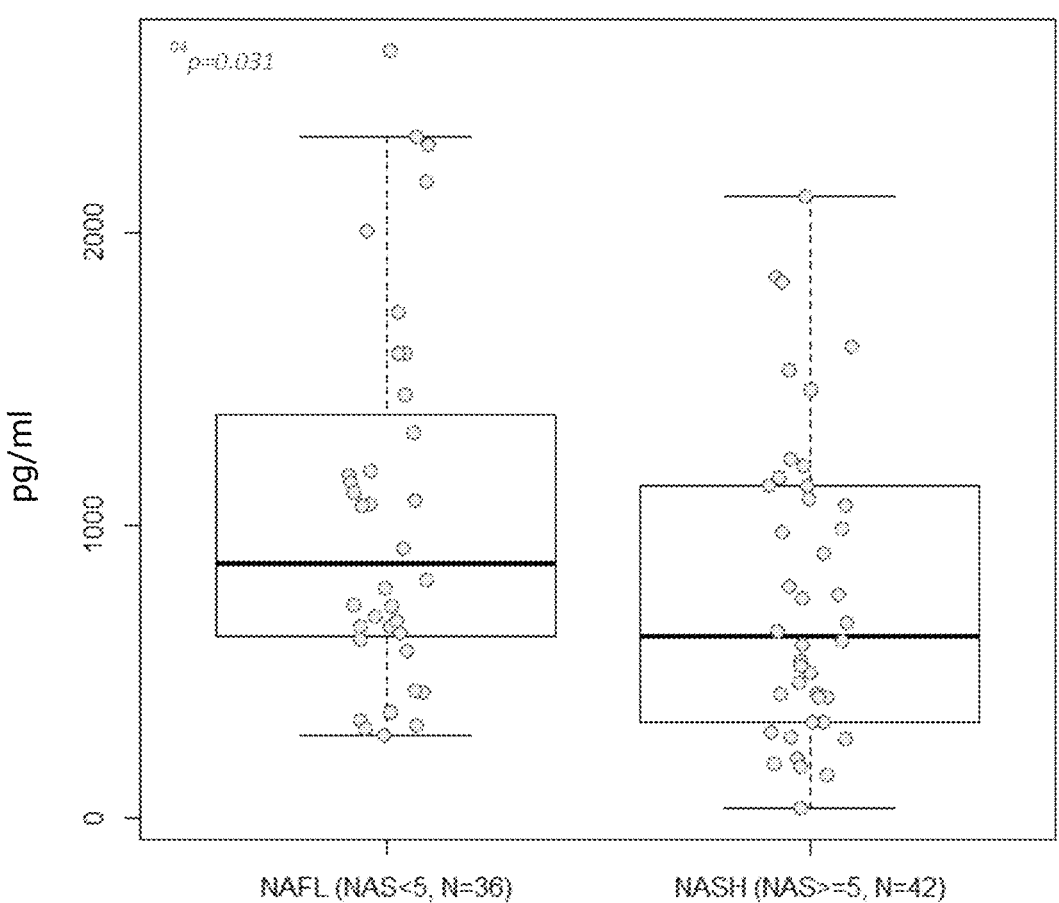

FIGS. 1A-1C: Boxplots—Univariate analysis of biomarkers allowing to distinguish between NASH and NAFL. A: CXCL10, B: IL-8, C: ghrelin.

Figure 2A:
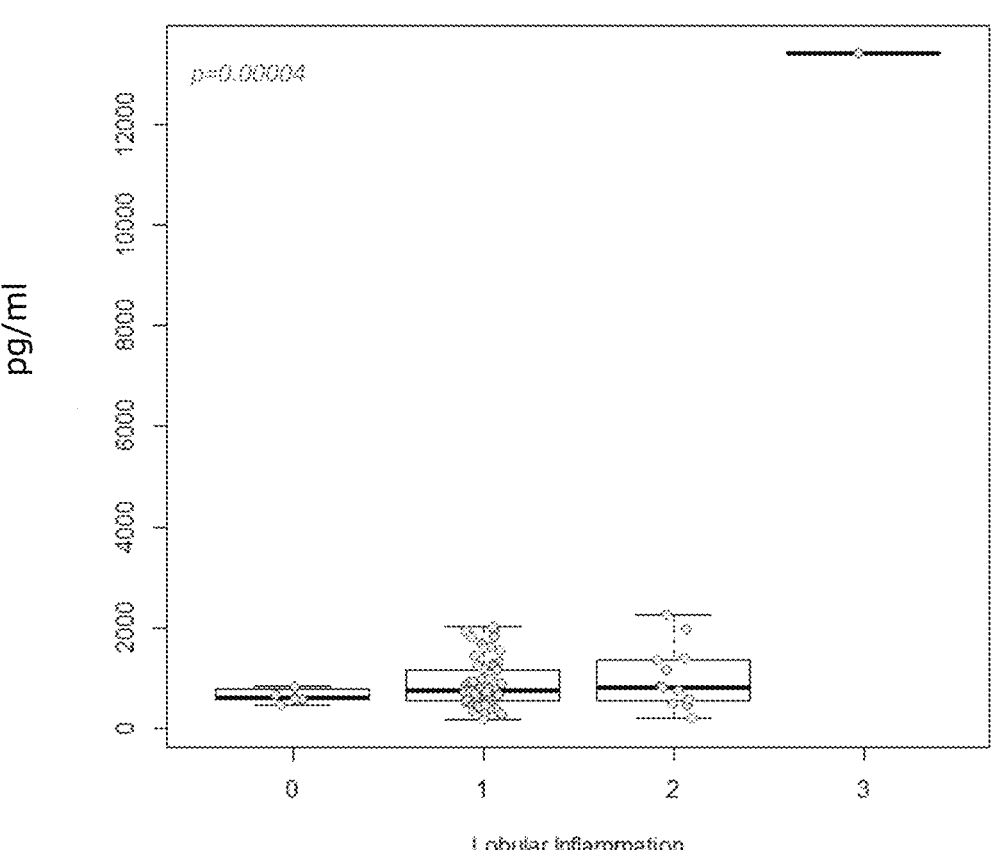
Figure 2B:
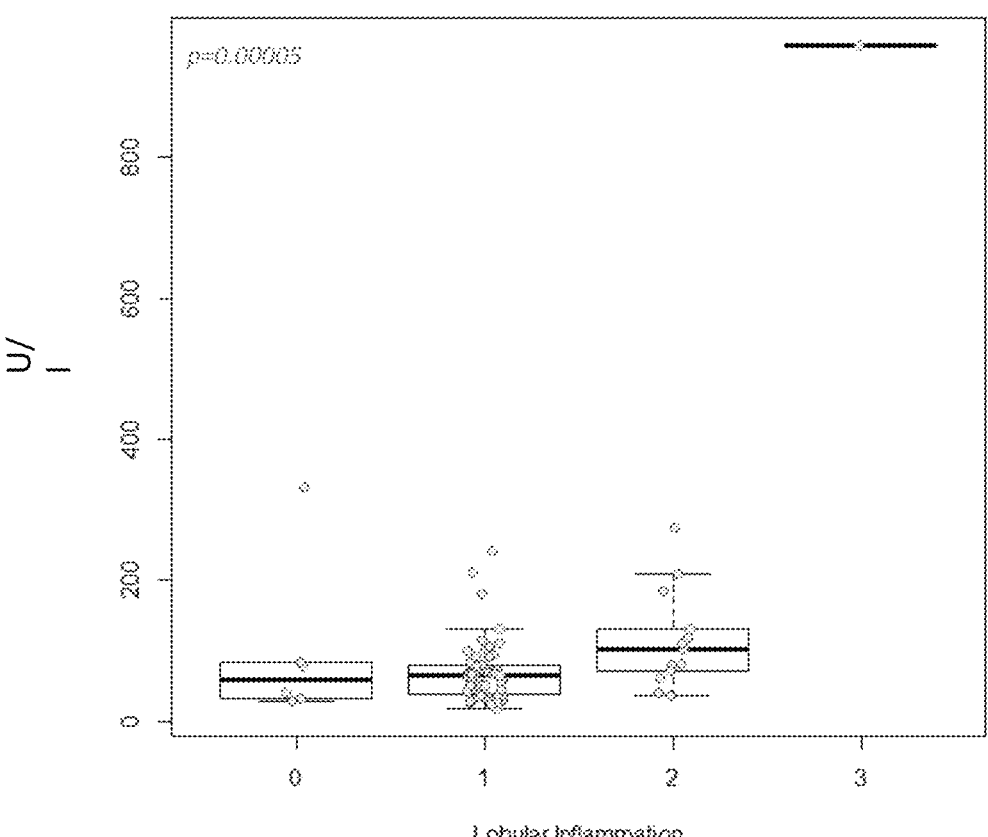
Figure 2C:
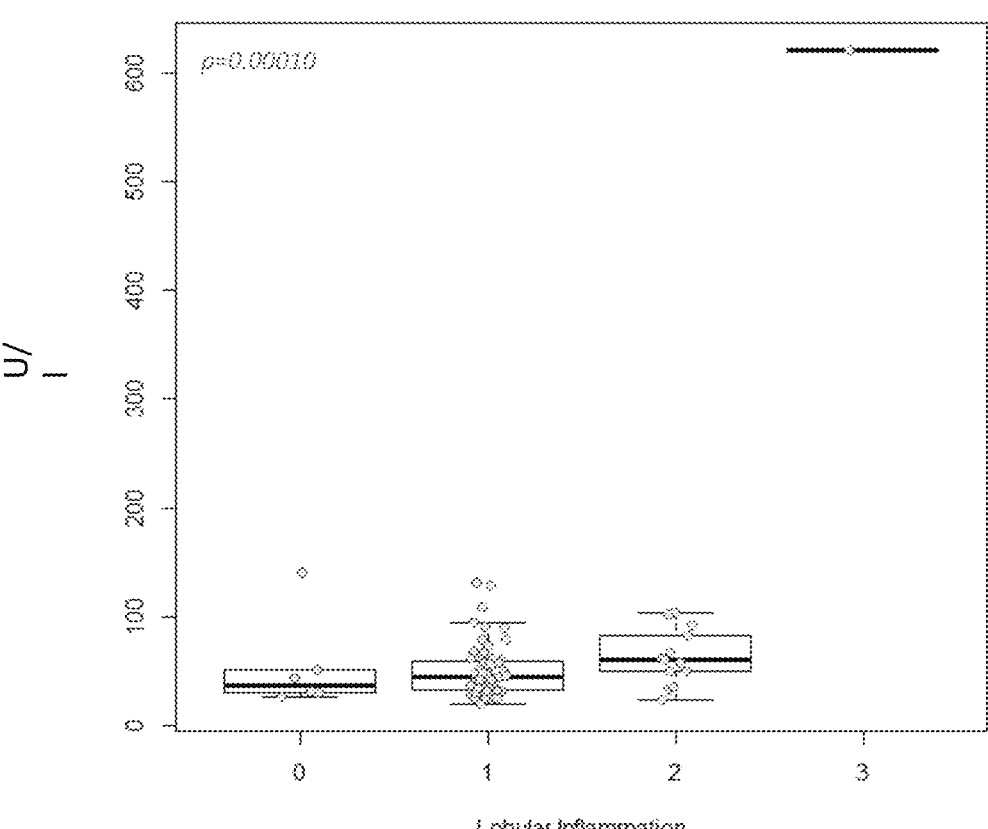

FIGS. 2A-2C: Boxplots—Univariate analysis of biomarkers allowing to distinguish between histologic grades of lobular inflammation (NAS score). A: CXCL10, B: ALAT, C: ASAT.

Figure 3A:
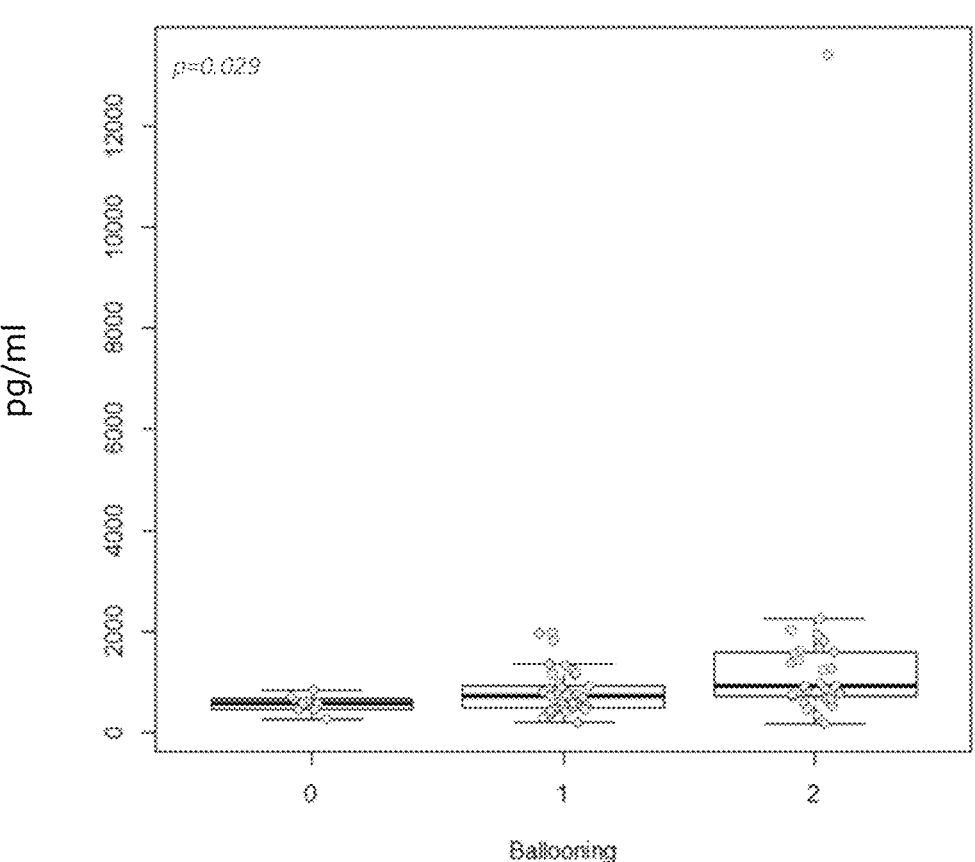
Figure 3B:
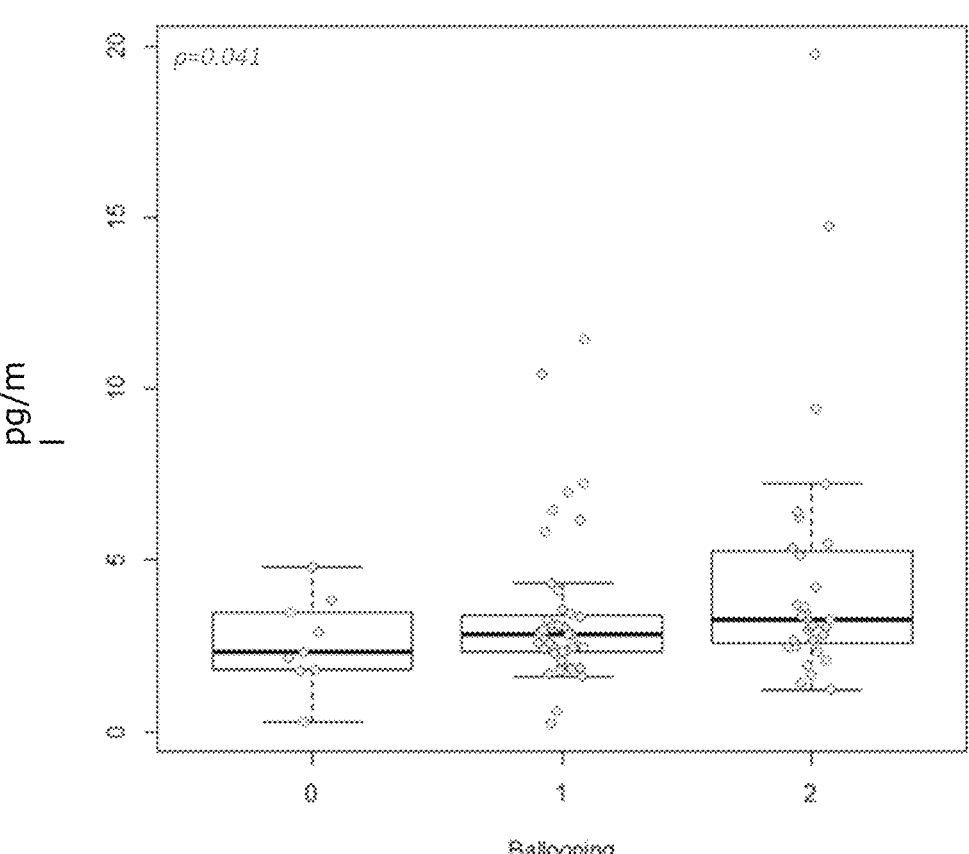

FIGS. 3A-3B: Boxplots—Univariate analysis of biomarkers allowing to distinguish between histologic grades of hepatocyte ballooning (NAS score). A: CXCL10, B: IL-8.

Figure 4A:
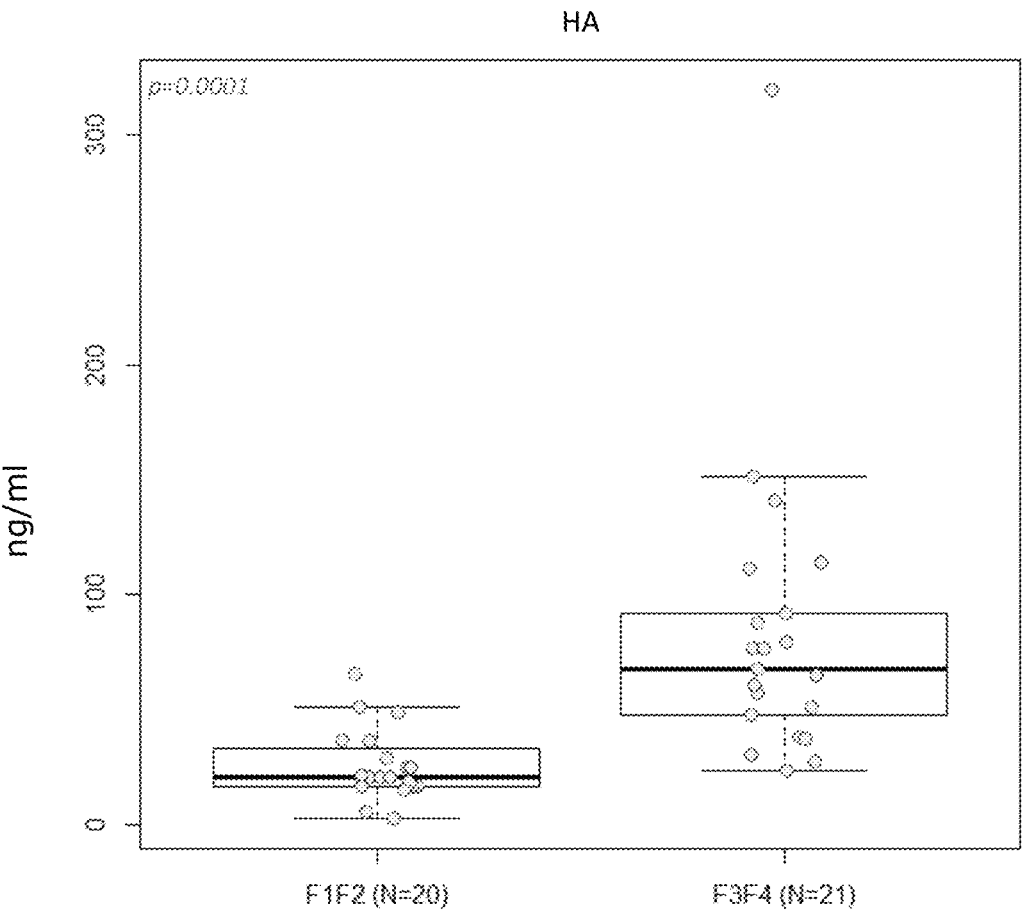
Figure 4B:
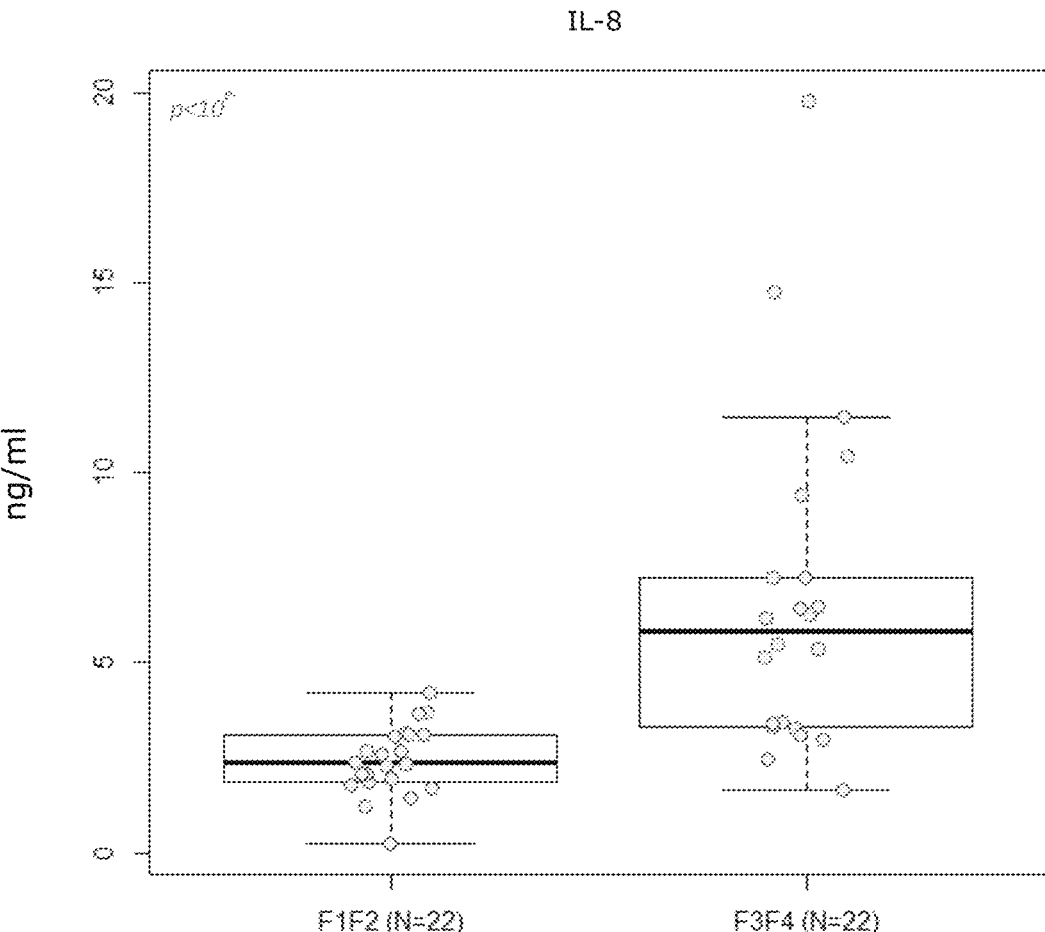
Figure 4C:
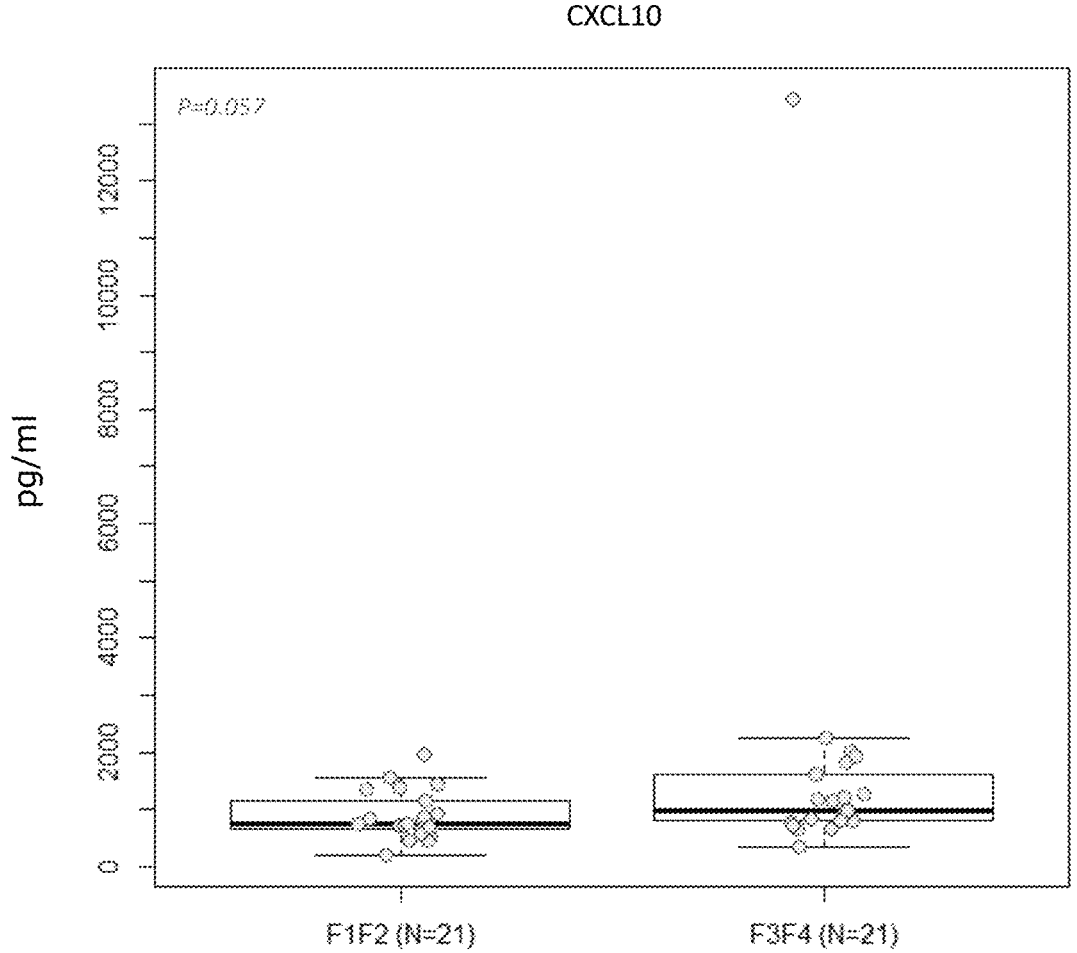

FIGS. 4A-4C: Boxplots—Univariate analysis of biomarkers allowing to distinguish between a fibrosis stage of F<3 and F≥3 in NASH patients. A: HA, B: IL-8, C: CXCL10.

Figure 5:
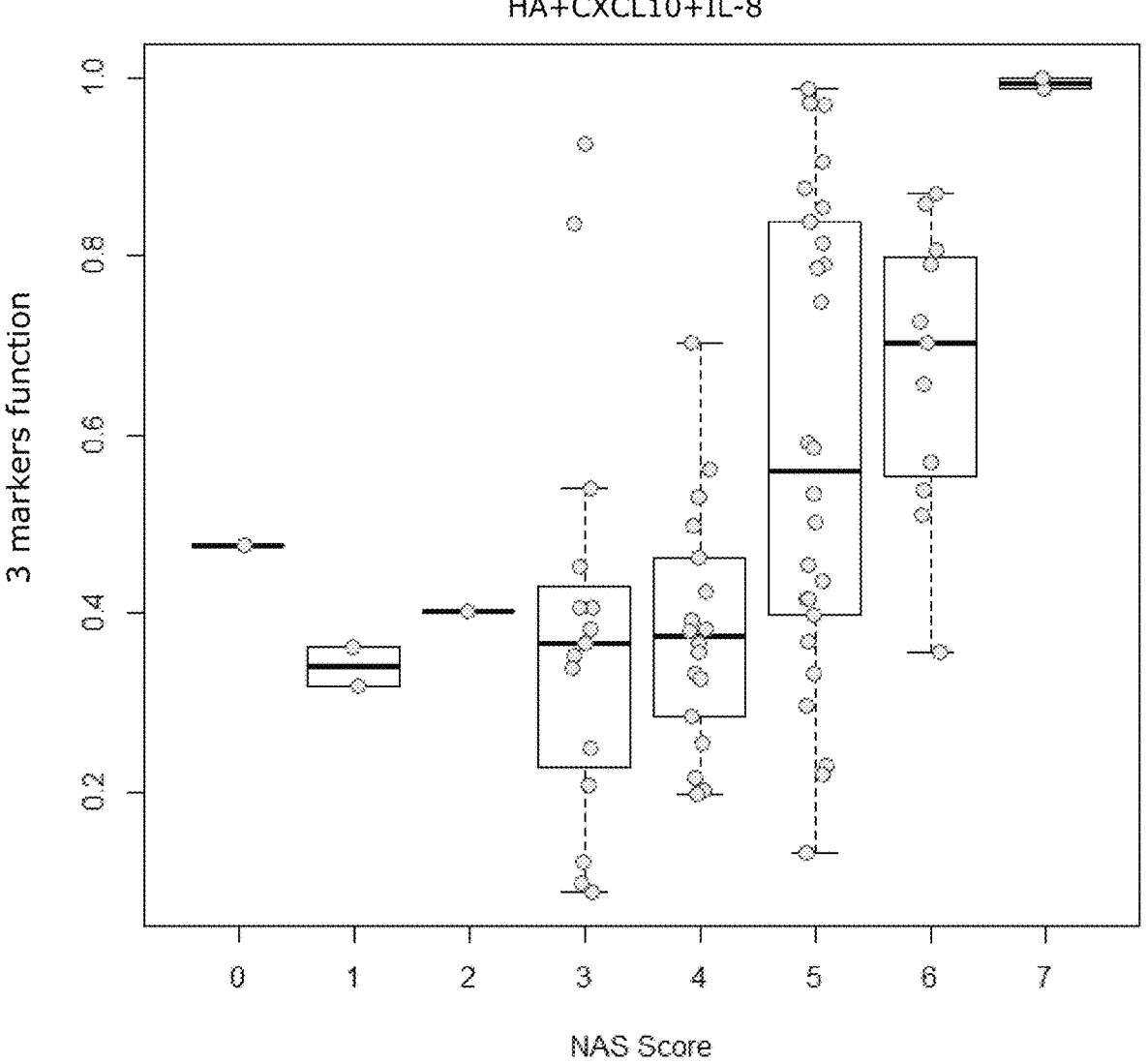

FIG. 5: Boxplots—3 markers function for NASH diagnostic.

Figure 6:
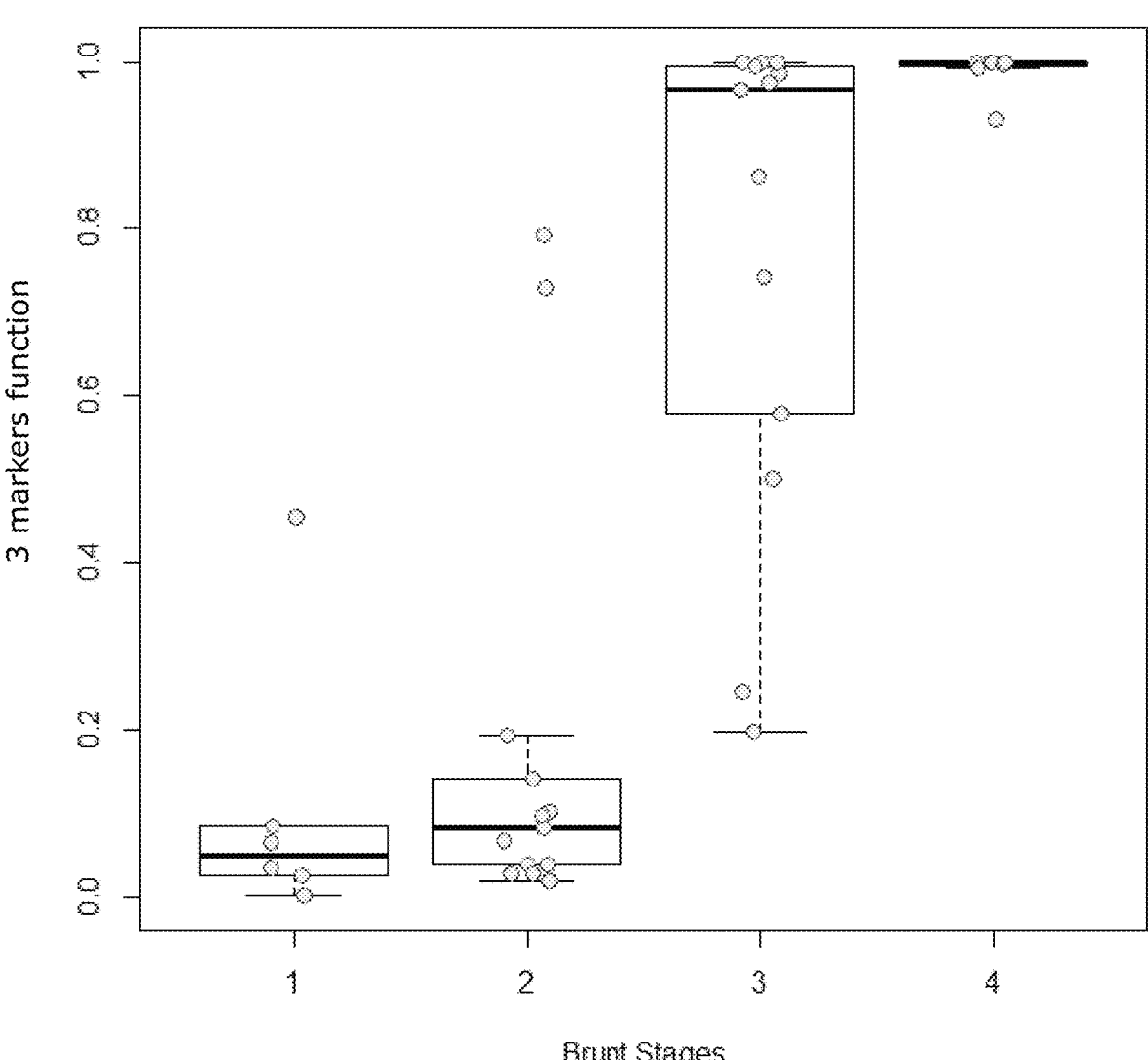

FIG. 6: Boxplots—3 markers function for fibrosis staging.

DETAILED DESCRIPTION OF THE INVENTION

The invention provides, as described above, methods of diagnosing Non-Alcoholic Steatohepatitis (NASH) based on the levels of particular biomarkers and the mathematical model or the threshold method described herein and, optionally, treating subjects diagnosed as having NASH.

"Biomarkers" as used herein first of all refers to circulating molecules which are found in bodily fluids. Preferred biomarkers are interleukins, cytokines, especially pro-inflammatory cytokines, chemokines, hormones and carbohydrates, especially glycosaminoglycans. Biomarkers of particular interest in the context of this invention are IL-8, HA, CXCL10, ghrelin, pre-HP2 and haptoglobin. Additionally, the term biomarker is also used herein to refer to patient characteristics (e.g., liver stiffness) obtained by non-invasive techniques to stage fibrosis such as Fibroscan®, and further to refer to clinical variables such as age, sex, BMI, hypertension and blood pressure.

In a particular embodiment, "pre-HP2" is equivalent to zonulin. "NASH" as used herein refers to the progressive form of Non-alcoholic fatty liver disease (NAFLD) which is the hepatic manifestation of metabolic syndrome. More generally, characteristic for NASH is that the fatty change (steatosis) is associated with lobular inflammation and hepatocyte injury with or without hepatic fibrosis. NASH is a very common disorder that is linked to obesity, type 2 diabetes, insulin resistance, and metabolic syndrome. It is present in more than 50% of overweight patients with type 2 diabetes. Its presence is associated not only with increased liver morbidity and mortality but also cardiovascular diseases.

The "measuring" of levels in step (I) of the methods described above may refer to any kind of detection and quantification of the biomarkers. In preferred embodiments ligands such as antibodies or naturally or recombinant proteins or peptides, which specifically bind to the biomarkers, may be used for the detection, and the quantification may be based on a signal obtained from a label conjugated to the ligand. Examples for such labels are fluorescent labels, biotin or peroxidase. The signal intensity can be amplified. The technologies that can be used for quantification of the biomarkers can be for example a multiplexing technology (for example the luminex multiplex technology), a microarray, an Enzyme-Linked Immunosorbent Assay (ELISA) or a Point of Care testing. Levels of additional biomarkers such as liver stiffness, age, sex, BMI, hypertension and blood pressure are measured by means known to the person skilled in the art. In a particular embodiment, liver stiffness is measured using Fibroscan®. Measuring the level of hypertension generally requires measuring both the systolic blood pressure and the diastolic blood pressure of a subject. In a particular embodiment, hypertension is deemed to be positive when the systolic blood pressure of the subject is greater than or equal to 140 millimeters of mercury (mm Hg) or when her/his diastolic blood pressure is greater than or equal to 90 mm Hg, and deemed to be negative when the systolic blood pressure of said subject is lower than 140 mm Hg and her/his diastolic blood pressure is lower than 90 mm Hg.

In a particular embodiment, the biomarker blood pressure is combined instead of or in addition to the biomarker hypertension in a mathematical model as disclosed herein. The level of systolic blood pressure and/or the level diastolic blood pressure is then measured, for example in mm Hg. When both the level of systolic blood pressure and the level of diastolic blood pressure are measured, either one or both levels can be combined in a mathematical model as disclosed herein.

The measuring of the levels of those biomarkers which are circulating molecules, is effected in a sample obtained from a "subject", which can be any human subject, and can be in particular a patient suspected to be afflicted with a liver disease, especially NAFLD or NASH. Alternatively, in a particular embodiment, where the method aims at determining the hepatic fibrosis status as described in (2) above, the subject may be known to be afflicted with NASH. Alternatively, in a particular embodiment, the subject may be an obese patient, a patient afflicted with or suspected to be afflicted with metabolic disorders inducing liver lesions such as cardiovascular diseases or diabetes or a subject afflicted with or suspected to be afflicted with a blood virus such as a human immunodeficiency virus (HIV; for example a HIV-1 or HIV-2) or a hepatitis virus (for example a hepatitis C virus; HCV).

"Samples" from which the levels of the circulating molecules can be measured include all kinds of bodily fluids such as blood, cerebrospinal fluid (CSF) or urine. In a preferred embodiment the sample is a blood sample, more preferably a serum or plasma sample, most preferably a serum sample.

The "combining" of the levels of the biomarkers is achieved with a mathematical model. A "mathematical model" which can be used for this purpose is e.g. a regression formula, preferably a logistic regression, but it can also be a SVM, a Random Forest, a decision tree, a mROC, a gradient boosting or any other method used in supervised classification.

As used herein, the singular forms "a", "an" and "the" are intended to include the plural forms as well, unless the context clearly indicates otherwise. Further, to the extent that the terms "including", "includes", "having", "has", "with", or variants thereof are used in either the detailed description and/or the claims, such terms are intended to be inclusive in a manner similar to the term "comprising". The transitional terms/phrases (and any grammatical variations thereof) "comprising", "comprises", "comprise", include the phrases "consisting essentially of", "consists essentially of", "consisting", and "consists" and can be interchanged throughout the application. The phrases "consisting essentially of" or "consists essentially of" indicate that the claim encompasses embodiments containing the specified materials or steps and those that do not materially affect the basic and novel characteristic(s) of the claim.

In the context of compositions administered to a subject for the treatment of NASH, the terms "about" or "approximately" are intended to permit for a variation of 0-10% around the stated value (X±10%). It should also be noted that ranges are stated in shorthand, so as to avoid having to set out at length and describe each and every value within the range. Any appropriate value within the range can be selected, where appropriate, as the upper value, lower value, or the terminus of the range. For example, a range of 0.1-1.0 represents the terminal values of 0.1 and 1.0, as well as the intermediate values of 0.2, 0.3, 0.4, 0.5, 0.6, 0,7, 0.8, 0.9, and all intermediate ranges encompassed within 0.1-1.0, such as 0.2-0.5, 0.2-0.8, 0.7-1.0, etc.

The terms "treatment", "treating", "palliating" and "ameliorating" (and grammatical variants of these terms), as used herein, can be used interchangeably and refer to an approach for obtaining beneficial or desired results including but not limited to therapeutic benefit. A therapeutic benefit is achieved with the eradication or amelioration of one or more of the physiological symptoms associated with NASH such that an improvement is observed in the patient, notwithstanding that the patient may still be afflicted with NASH or NAFLD.

The term "effective amount" or "therapeutically effective amount" refers to that amount of a therapeutic agent sufficient to treat a subject.

"Subject" refers to an animal, such as a mammal, for example a human. The methods described herein can be useful in both humans and non-human animals. In some embodiments, the subject is a mammal (such as an animal model of disease), and in some preferred embodiments, the subject is human.

The terms "administer" or "administration" (and any grammatical variants thereof) refer to the oral, subcutaneous, intraperitoneal, intravenous, or intramuscular administration of a treatment or therapeutic agent to a subject.

A logistic regression model of interest in the context of the present invention can be written as Formulae (1) and (2) below:

$$f = \frac{\exp(y)}{1 + \exp(y)}, \qquad \text{[Formula (1)]}$$

where y in formula (1) is defined as:

$$y = a_1 + \sum_{k=2}^{n} a_k BMK_{k-1}. \qquad \text{[Formula (2)]}$$

The diagnostic score is the value comprised in the interval [0,1] and is obtained with Formula (1), i.e. the decision function f.

In a particular embodiment, the clinical decision thresholds (for example, as defined in Tables 4a, 4b, 5a and 5b) are set to classify patients as NASH or NAFL or as NASH patients with or without advanced fibrosis stage ($F{\geq}3$ or $F{<}3$, respectively). Values of clinical decision thresholds are comprised in the interval [0,1].

By "comprised in the interval" or "comprised in the range", it is meant herein that the indicated bounds are included in said interval/range.

Suitable regression formulae that can be used for the implementation of the method of the invention are given in the first row of Tables 4a and 4b (NASH diagnosis) and Tables 5a and 5b (fibrosis stage), respectively. These regression formulae correspond to Formula (2) above, with the specific coefficients $a_k$ for each particular formula corresponding to $a_k$ in Formula (2) above. The specific coefficients depend on the number of markers used for the diagnosis as given in the respective Table. In these tables, the ranges of coefficients observed and threshold set during the 10-fold cross validation process disclosed in the examples are displayed as "Range_$a_k$" and "Range Threshold", respectively. Furthermore, these ranges are displayed "rounded" (as "Range_$a_k$ rounded" and "Range_Threshold_rounded", respectively) with the floor (the greatest preceding integer) and ceiling (the least succeeding integer) functions, respectively for the lower and upper bounds. Moreover, for each one of the biomarkers described and each diagnosis (NASH or Fibrosis), global ranges of coefficients and global ranges of thresholds were defined for the associated coefficients and thresholds according to the rounded ranges. Theses ranges, given as "Range_$a_k$_rounded_global" and "range_Threshold_rounded_global", respectively, in the respective Table, are made up of the minimum and the maximum values of all the rounded ranges observed for the coefficient of a particular biomarker or for the threshold. As an example, the biomarker pre-HP2 is member of 5 upon the 9 signatures selected on NASH diagnosis disclosed in these tables (signatures $y_1$ to $y_9$). Among the 5 rounded ranges concerning pre-HP2 on NASH diagnosis, the minimal value is −1 and the maximal value is 1 so the allowed values for the coefficients linked to pre-HP2 have to be in the range [−1, 1]. These rounded ranges can be used to define more broadly which value each coefficient can assume and the threshold in a given signature. Alternatively, Formula (3) below, corresponding to the last column ($y_9$) in Tables 4b and 5b, can be used with a variable number of measured biomarkers, i.e. with 3 to 11 biomarkers.

$$y_{10}=a_1+a_2\times[IL8(pg/ml)]+a_3\times[HA(ng/ml)]+a_4\times[CXCL10(pg/ml)]+i_5\times a_5\times[ghrelin(pg/ml)]+i_6\times a_6\times[pre-HP2(ng/ml)]+i_7\times a_7\times[haptoglobin(mg/ml)]+i_8\times a_8\times[Liver\ stiffness(kPa)]+i_9\times a_9\times[age(year)]+i_{10}\times a_{10}\times[sex(m=1;\ f=0)]+i_{11}\times a_{11}\times[BMI(kg/m^2)]+i_{12}\times a_{12}\times[hypertension(yes=1;\ no=0)]$$ [Formula (3)]

For each biomarker used in Formula (3) the indicator function $i_k$ (k=5, . . . , 12) equals 1 and for those biomarkers not used the indicator function $i_k$ equals 0.

Hence, in a particular embodiment, Formula (3) is used with the 11 biomarkers recited in said formula (i5 to i12=1), i.e. $y_{10}$ is $y_9$:

$$y_9=a_1+a_2\times[IL8(pg/ml)]+a_3\times[HA(ng/ml)]+a_4\times[CXCL10(pg/ml)]+a_5\times[ghrelin(pg/ml)]+a_6\times[pre-HP2(ng/ml)]+a_7\times[haptoglobin(mg/ml)]+a_8\times[Liver\ stiffness(kPa)]+a_9\times[age(year)]+a_{10}\times[sex(m=1;\ f=0)]+a_{11}\times[BMI(kg/m^2)]+a_{12}\times[hypertension(yes=1;\ no=0)]$$ [Formula (4)]

Other examples of variations of Formula (3), in which a combination of 3 to 6 biomarkers are used, are disclosed in Tables 4 and 5 as $y_1$ to $y_8$ ([Formula (5)] to [Formula (12)], respectively).

In a particular embodiment, the coefficients $a_k$ of $y_1$ to $y_9$ have the value given as "$a_k$" in Tables 4a and 4b (NASH diagnosis) and Tables 5a and 5b (Fibrosis stage), respectively.

More generally, in a particular embodiment, the coefficients $a_k$ of $y_1$ to $y_9$ have a value comprised in the range given as "Range_$a_k$" or "Range_$a_k$_rounded" in Tables 4a and 4b (NASH diagnosis) and Tables 5a and 5b (Fibrosis stage), respectively.

Still more generally, in a particular embodiment, the coefficients $a_k$ have a value comprised in the range given as "Range_$a_k$_rounded_global" in Tables 4a and 4b (NASH diagnosis) and Tables 5a and 5b (Fibrosis stage), respectively.

In a particular embodiment, the coefficients $a_k$ of Formula (3) have the value given as "$a_k$" for $y_9$ in Tables 4a and 4b (NASH diagnosis) and Tables 5a and 5b (Fibrosis stage), respectively.

In a particular embodiment, the coefficients $a_k$ of Formula (3) have a value comprised in the range given for $y_9$ as "Range_$a_k$", "Range_$a_k$_rounded" or "Threshold_rounded_global" in Tables 4a and 4b (NASH diagnosis) and Tables 5a and 5b (Fibrosis stage), respectively.

Hence, in a particular embodiment for the diagnosis of NASH, Formula (3) is used with the following coefficients $a_k$:

| Coefficient | Comprised in the range | |
| --- | --- | --- |
| | From | To |
| $a_1$ | −9 | 12 |
| $a_2$ | 0 | 2 |
| $a_3$ | −1 | 2 |
| $a_4$ | −1 | 1 |
| $a_5$ | −1 | 1 |
| $a_6$ | −1 | 1 |
| $a_7$ | −1 | 1 |
| $a_8$ | −1 | 1 |
| $a_9$ | −1 | 1 |
| $a_{10}$ | −3 | 2 |
| $a_{11}$ | −1 | 1 |
| $a_{12}$ | −1 | 1 |

In a particular embodiment for the staging of fibrosis, Formula (3) is used with the following coefficients $a_k$:

| Coefficient | Comprised in the range | |
| --- | --- | --- |
| | From | To |
| $a_1$ | −20127 | −2 |
| $a_2$ | 0 | 1459 |
| $a_3$ | −1 | 129 |
| $a_4$ | −24 | 1 |
| $a_5$ | −1 | 11 |
| $a_6$ | −4 | 4 |
| $a_7$ | −29 | 5 |
| $a_8$ | −1 | 462 |
| $a_9$ | −1 | 1 |
| $a_{10}$ | −1 | 0 |
| $a_{11}$ | −1 | 1 |
| $a_{12}$ | −32 | 11 |

In a particular embodiment for the diagnosis of NASH, the subject is determined as being afflicted with NASH when the score f obtained with the coefficients $a_k$ is greater than the threshold $t_{\_NASH}$, wherein $t_{\_NASH}$ has a value comprised in the range [0,1]. Otherwise, if f is less than or equal to $t_{\_NASH}$, the subject is determined as not being afflicted with NASH. In a particular embodiment, $t_{\_NASH}$ has a value comprised in the range given as "Range_Threshold_rounded_global" in Tables 4a and 4b. In a more particular embodiment, $t_{\_NASH}$ has a value comprised in the range given as "Range_Threshold" or "Range_Threshold_rounded in Tables 4a and 4b. In a still more particular embodiment, $t_{\_NASH}$ has the value given as "Threshold" in Tables 4a and 4b, i.e. the value 0.4997 (or 0.50) when y is $y_1$;
0.4805 (or 0.48) when y is $y_2$;
0.5825 (or 0.58) when y is $y_3$;
0.5045 (or 0.50) when y is $y_4$;
0.5076 (or 0.51) when y is $y_5$;
0.3715 (or 0.37) when y is $y_6$;
0.5045 (or 0.50) when y is $y_7$;
0.5219 (or 0.52) when y is $y_8$; and
0.6459 (or 0.65) when y is $y_9$ or $y_{10}$.

In a particular embodiment for the staging of fibrosis, the hepatic fibrosis status of the subject is determined as being advanced fibrosis (which corresponds to a fibrosis Score of $F \geq 3$) when the score f obtained with the coefficients $a_k$ is greater than the threshold $t_{\_fibrosis}$, wherein $t_{\_fibrosis}$ has a value comprised in the range [0,1]. Otherwise, if f is less than or equal to $t_{\_fibrosis}$, the hepatic fibrosis status of the subject is determined as corresponding to a fibrosis Score of $F<3$. In a particular embodiment, $t_{\_fibrosis}$ has a value comprised in the range given as "Range_Threshold_rounded_global" in Tables 5a and 5b. In a more particular embodiment, $t_{\_fibrosis}$ has a value comprised in the range given as "Range_Threshold" or "Range_Threshold_rounded" in Tables 5a and 5b. In a still more particular embodiment, $t_{\_fibrosis}$ has the value given as "Threshold" in Tables 5a and 5b, i.e., the value 0.1953 (or 0.20) when y is $y_1$;

0.1253 (or 0.13) when y is $y_2$;

0.6804 (or 0.68) when y is $y_3$;

0.5739 (or 0.57) when y is $y_4$;

0.6569 (or 0.66) when y is $y_5$;

0.4918 (or 0.49) when y is $y_6$; and 0.5 when y is $y_7$, $y_8$, $y_9$ or $y_{10}$.

In a particular embodiment, Formula (3) is used and $t_{\_NASH}$ and $t_{\_fibrosis}$ have a value comprised in the range given for $y_9$ as "Range_Threshold", "Range_Threshold_rounded" or "Range_Threshold_rounded_global" in Tables 4a and 4b (NASH diagnosis) and Tables 5a and 5b (Fibrosis stage), respectively.

The method of the invention as defined in (2) above is suitable to determine the hepatic fibrosis status of a subject, especially a subject afflicted with NAFLD or NASH. The hepatic fibrosis status refers to the stage and severity of hepatic fibrosis and is of great importance to a physician's decision what treatment to administer. In a particular embodiment, the hepatic fibrosis status referred to herein corresponds to any one of the Brunt Score (Brunt, E. M., et al., Am J Gastroenterol, 1999. 94(9): p. 2467-74), the Metavir score (Hepatology. 1996 August; 24(2):289-93.), the Kleiner score (Kleiner, D. E., et al., Hepatology, 2005. 41(6): p. 1313-21.) or the SAF score (Bedossa, P. and F. P. Consortium, Hepatology, 2014. 60(2): p. 565-75). While the method of the invention is particularly suited to diagnose NASH and/or the severity of NASH in patients known to be afflicted with NAFLD, the method is likewise suited to be used in the diagnosis of NASH and/or the severity of NASH in patients with other comorbidities such as e.g. cardiovascular diseases, diabetes, obesity or infections with blood viruses such as a HIV (for example, a HIV-1 or HIV-2) or a hepatitis virus (for example, a HCV).

As discussed above, the disclosed methods may further comprise the treatment of a subject diagnosed with NASH in accordance with the disclosed diagnostic methods (i.e., "the mathematical model" or "the threshold method"). In certain embodiments, patients diagnosed with NASH can be treated by administration of glitazones, such as rosiglitazone or pioglitazone, alone or in combination with Vitamin E; FXR agonists, such as GS-9674, LJN-452, EDP-305, and obeticholic acid; PPAR α and PPAR β (also known as PPARδ) and/or PPAR γ agonists, such as elafibranor, saroglitazar, IVA-337; FGF-19 analogues, such as NGM-282; FGF21 analogues, such as PF-05231023 ((CVX-343), a long-acting FGF21 analog, composed of two molecules of [des-His1, Ala129Cys]FGF21 covalently linked to a humanized IgG$_{1\kappa}$ mAb backbone via a maleimide-azetidinone linker, Giragossian et al., 2015, Drug Metabolism and Disposition, 43(6):803-811, which is hereby incorporated by reference in its entirety); SDD1 inhibitors, such as aramchol, GLP-1 analogues, such as liraglutide, Nor-ursodeoxycholic acid (UDCA); antioxidants, such as Vitamin E; ASK1 inhibitors, such as GS-4997; VAP-1 inhibitors, such as PXS-4728A; CCR2/CCR5 antagonists, such as cenicriviroc; pentamidines, such as VLX-103; caspase inhibitors, such as emricasan; LOXL2 inhibitors, such as simtuzumab; and/or falectin-3 protein inhibitors, such as galactoarabino rhamnogalacturonate (GR-MD-02) or any other treatment disclosed in Friedman et al., 2018, Mechanisms of NAFLD development and therapeutic strategies, Nature Medicine, 24:908-922, which is hereby incorporated by reference in its entirety. Other treatments for individuals diagnosed with NASH using either diagnostic method are described in Tables 10 and 11.

The invention will be further described in the following Examples which are not to be construed as limiting the invention.

EXAMPLES

Material and Methods

1. Patient Population: A total of 84 NAFLD patients with well-characterized and biopsy-confirmed NAFL or NASH with matched serum samples were included in this study. Consecutively biopsied patients were followed at Pessac Hospital (Bordeaux, France) between 2011 and 2014. The study was approved by the local ethics committee and conformed to the 1975 Declaration of Helsinki. All patients gave their written informed consent. For each patient, 5 ml of venous blood was collected in standard dry tubes. The tubes were labelled with a code identifying the patient, date and time of sampling. Serum samples (1 ml) from all groups were centrifuged and stored at −80° C. for biomarker assessment. All biomarker analyses on human samples were performed by blinded operators.

The clinical diagnosis of NAFLD was based on the following criteria: elevated aminotransferases (AST and or/ALT); liver biopsy showing steatosis in at least 5% of hepatocytes; and appropriate exclusion of liver disease of other etiology including alcohol-induced or drug-induced liver disease, autoimmune or viral hepatitis. All patients had a negative history of ethanol abuse as indicated by a weekly ethanol consumption of <140 g in women and <210 g in men.

Clinical and laboratory data were collected the same day as the diagnostic of the liver biopsy. Clinical characteristics of the included patients are listed in Table 1. BMI was calculated using the formula: weight (in kilograms)/(height (in meters)$^2$). Hypertension is defined by blood pressure measurement and a reading given in mm Hg. Hypertension was deemed to be positive when systolic blood pressure was ≥140 mm Hg or diastolic pressure was ≥90 mm Hg. Laboratory evaluation included routine liver biochemistry (ALT and AST levels, gamma glutamyl transpeptidase (GGT), platelets, HDL cholesterol, total triglycerides and fasting glucose). The diagnosis of NAFL/NASH was based on liver biopsy and the NAS scoring system according to Kleiner, D. E., et al., Hepatology, 2005. 41(6):1313-21. This exploratory cohort included 84 NAFLD patients of which 44 were diagnosed as NASH patients.

2. Liver histology (NASH, Fibrosis): The severity of NASH was evaluated according to the NAS scoring system (Kleiner, D. E., et al., Hepatology, 2005. 41(6):1313-21) and the score for each component of NAS was calculated as follows: steatosis (0-3), lobular inflammation (0-3) and ballooning (0-2). The final score was calculated as the sum of the scores of the three components: ≤2 (No NASH), 3-4

(borderline) and ≥5 (NASH). In the studied population and according to the NAS scoring system, 44 patients were diagnosed NASH and 40 patients NAFL (No NASH+borderline patients).

Liver biopsy for fibrosis was evaluated according to the Brunt score (Brunt, E. M., et al., Am J Gastroenterol, 1999. 94(9):2467-74): F0=no fibrosis; F1=centrilobular perisinusoidal fibrosis; F2=centrilobular perisinusoidal fibrosis and/or portal periportal fibrosis; F3=bridging fibrosis; F4=cirrhosis. Significant fibrosis was defined as F≥2, advanced fibrosis as F≥3, and cirrhosis as F4. As recommended by the latest EASL guidelines (European Association for the Study of the Liver, Obes Facts, 2016. 9(2):65-90), we chose NASH patients with advanced fibrosis (F≥3) as our primary diagnostic target. In the studied population and according to the Brunt score, 4 patients were evaluated at F0 stage, 20 patients at F1, 25 patients at F2, 24 patients at F3 and 11 patients at F4.

3. Liver stiffness measurement: Liver stiffness measurement (LSM) with Fibroscan® was performed using the standard M or XL probes by a specialized nurse experienced with the procedure and who was blinded for patient data. LSM was performed in fasting condition on the day of liver biopsy or no more than three months before or after. Examination conditions were those recommended by the manufacturer (Castera, L., X. Forns, and A. Alberti, J Hepatol, 2008. 48(5):835-47). LSM was stopped when 10 valid measurements were recorded and the result was expressed as the median of these valid measurements. LSM failure was defined as LSM with no valid measurement (0% success rate) or LSM with only one valid measurement with thus no interquartile range (IQR) calculated by the device.

4. Biological scores of fibrosis: Fasting blood samples were taken the day of or within the week preceding liver biopsy. Six blood fibrosis tests were calculated according to the most recent formulae, instructions and cut-off values: Fibrotest® (sex, age, α2-macroglobulin, haptoglobin, GGT, apolipoprotein A1 and bilirubin) (Imbert-Bismut, F., et al., Lancet, 2001. 357(9262):1069-75), Hepascore® (age, sex, α2-macroglobulin, hyaluronic acid, gamma glutamyltransferase and bilirubin) (Adams, L. A., et al., Clin Chem, 2005. 51(10):1867-73), Forn's score (age, platelet count, GGT and cholesterol) (Forns, X., et al., Hepatology, 2002. 36:986-92), APRI (AST to platelet ratio index) (Wai, C. T., et al., Hepatology, 2003. 38(2):518-26), FIB-4 (age, AST and ALT levels and platelet counts) (Sterling, R. K., et al., Hepatology, 2006. 43(6):1317-25), NAFLD fibrosis score (age, BMI, impaired fasting glucose (IFG), AST/ALT ratio, platelet, albumin) (Angulo, P., et al., Hepatology, 2007. 45(4):846-54). NAFLD fibrosis score was specifically developed for liver fibrosis assessment in NAFLD whereas the five other tests were developed in patients with chronic viral hepatitis.

5. Measurement of serum levels of biomarkers (ELISA and Bioplex/Luminex): A total of 6 biomarkers were quantified in the serum of all patients: Hyaluronan (HA), C-X-C motif chemokine 10 (CXCL10 or IP10), Interleukin 8 (IL-8), ghrelin, pre-HP2 and haptoglobin. Serum concentrations of 4 biomarkers were measured by commercial or home-made ELISA and 2 by commercial Bio-Rad Bioplex panels (27-plex Cytokines and 10-plex Diabetes panels; Bio-Rad, Hercules, USA) according to manufacturer's instructions. Each experiment was performed in duplicate.

ELISA assays: Serum levels of CXCL10 were measured using DIP100 Quantikine Immunoassay for Human CXCL10/IP10 (coefficients of variation inter- and intra-plates are respectively: 3.4±1.9% and 4.4±2.1%; R&D Systems, Minneapolis, USA). Serum levels of HA were measured using DHYAL0 Quantikine Immunoassay (3.9±1.9% and 4.8±3.2%; R&D Systems, Minneapolis, USA). Serum Interleukin 8 (IL-8) concentrations were measured using Human IL-8 ELISA Kit, KHC0081, 4.1±3.8% and 3.4±2.8% ThermoFischer Scientific, Waltham, USA). Serum pre-HP2 concentrations were measured using Bio-Rad home-made ELISA (7.0±5.1% and 9.0±8.7%; Bio-Rad Hercules, USA) (Flanagan, J. J., et al., J Immunol Methods, 2014. 406: p. 34-42). Serum haptoglobin concentrations were measured using Human Haptoglobin Quantikine ELISA Kit, (DHAPG0; R&D Systems).

Bioplex/Luminex assays: A multiplex biometric ELISA-based immunoassay, containing dyed microspheres conjugated with a monoclonal antibody specific for a target protein was used according to the manufacturer's instructions (Bioplex, Bio-Rad, Hercules, USA). Soluble molecules were measured using two commercially available kits: i) CXCL10 within a 27-Plex panel and ii) ghrelin within a 10-Plex panel.

Briefly, 30 μl serum samples were diluted 1:4 with suitable buffer and incubated with antibody-coupled beads. Complexes were first washed, then incubated both with biotinylated detection antibody, and, finally, with streptavidin-phycoerythrin prior to assessing cytokine concentration titers. Concentrated human recombinant cytokine was provided by the vendor (Bio-Rad, Hercules, USA). A broad range, 1.951-32,000 pg/ml of standards, was used to establish standard curves to maximize the sensitivity and dynamic range of the assay. Serum levels of all proteins were determined using a Bio-Plex array reader (Luminex, Austin, USA) that quantifies multiplex immunoassays in a 96-well plate with very small fluid volumes. Concentrations of the analytes were calculated using the standard curves, with software provided by the manufacturer (Bio-Plex Manager Software).

6. Statistical analysis: For all the statistical analyses and figures used in this study the 'R v3.2.1' statistical open source software (see Worldwide Website: R-project.org/) was used. All data (biomarker concentrations and clinical variables) were evaluated with univariate differential analysis. We applied the Wilcoxon test to determine significant differences between groups of patients. For each biomarker we provide the following statistical information: the mean±standard deviation (SD); the p-value of the applied test; the q-value (p-values corrected for multiple testing with the Benjamini and Hochberg approach (Benjamini, D. a. H., Y., J Roy Statist Soc Ser B 1995. 57:289-300) implemented in the 'multtest' R package); the n-fold median (NASH/NAFL median ratio) and the AUC (Area Under the ROC Curve).

In addition to univariate analysis, all combinations of biomarkers were tested in order to evaluate the potential improvement using the logistic regression method (Hosmer, D. W. and Lemeshow, S., Applied logistic regression. Wiley Series in Probability and Mathematical Statistics, 2000). The logistic regression model can be written as given in Formulae (1) and (2) above.

The diagnostic performance of each combination of biomarkers is evaluated with the following criteria: the accuracy or good classification rate, which is the sum of true positives (TP) and true negatives (TN) divided by the total number of patients; the sensitivity (Se), which represents the capacity to detect the population termed "pathologic" (in the present case, "NASH" or "F≥3"), Se=TP/(TP+FN); the specificity (Sp), which represents the capacity to detect the population termed "controls" (in the present case, NAFL or "F<3"), Sp=TN/(TN+FP); the Positive Predictive Value (PPV) PPV=TP/(TP+FP); the Negative Predictive Value (NPV) NPV=TN/(TN+FN); the AUC, where ROC curves are the graphical visualization of the reciprocal relation between Se and Sp of a test for various thresholds. The closer the AUC is to one, the more the biomarker or combination of biomarkers is able to distinguish the two populations, i.e. either NASH/no NASH or fibrosis score of F≥3/F<3. For each selected signature, in addition to the performances described above, the parameters of the logistic regression model and the selected threshold are shown. The threshold is selected according to the Youden criteria (Youden, W. J., Cancer, 1950. 3(1):32-5), that is to say the one that maximizes Se+Sp-1.

In order to avoid over-fitting, the combinations of biomarkers were evaluated with the 10-fold cross validation method (Hastie, T. T., R. and Friedman, J. H., The Elements of Statistical Learning: Data Mining, Inference, and Prediction. Springer Science & Business Media, 2001) wherein the modeling is realized on 90% of the population and the prediction on the remaining 10%. This procedure is realized 10 times in such a way that each sample is alternately in the "Training set" and in the "Test set" (more precisely each sample is 9 times in the training set and once in the test set). The performances obtained on both training and test sets are shown. For each signature, 10 models have been built on the 10 training sets, the mean, minimum and maximum of the AUC, Se and Sp obtained on these training sets are presented (these are called AUC Training, Se training and Sp Training). When a sample is in the test set, the result is estimated from the model built with the remaining samples (training set) and is collected in such a manner that at the end all the estimations for all the samples are acquired (each sample being excluded from the model from which its estimation results have been made). The AUC, Se and Sp of the test set are also presented (these are called AUC Test, Se Test and Sp Test).

By definition the best indices ('NASH score' and 'fibrosis score') in terms of discrimination were the logistic regression functions combining independent factors. The logistic function is obtained by combining the relative weight of each parameter.

The regression formulae thus obtained are given in the first row of Tables 4a and 4b (NASH diagnosis) and Tables 5a and 5b (fibrosis stage), respectively, with the specific coefficients $a_k$, depending on the number of markers used for the diagnosis, given in the respective Tables, as disclosed herein.

Results

1. Characteristics of the patient population: Eighty-four biopsy proven NAFLD patients from the Pessac Bordeaux hospital were included in the study. The comparisons of clinico-demographic and laboratory data between NASH and NAFL patients are demonstrated in Table 1. The median (±SD) NAS score was 3.5 (±0.9) in the NAFL group and 5.0 (±0.6) for the NASH group. Increased serum ALT, AST and elevated liver steatosis were independently associated with an increased likelihood of NASH presence (Table 1). As expected, the prevalence of histological severe fibrosis stages (F3, F4) was predominant in the NASH versus the NAFL group with 50% and 32.5% respectively.
2. Univariate Analysis:
NASH biomarkers: Among the 6 studied circulating biomarkers, CXCL10 is the best biomarker allowing to distinguish the NASH and NAFL groups with p=0.001 and AUC=0.721(FIG. 1A and Table 2a). Decreased serum ghrelin was also associated with an increased likelihood of NASH presence with an average of 1051 (±634) pg/ml and 768 (±521) pg/ml in the NAFL and in the NASH groups, respectively (FIG. 1C and Table 2a).

Biomarkers of steatosis, lobular inflammation and hepatocyte ballooning according to the NAS scoring system: Among the 6 studied circulating biomarkers, three biomarkers were significantly deregulated according to lobular inflammation (NAS scoring system): CXCL10, IL-8 and pre-HP2 had significant p-values <0.05 (Table 3). The best biomarker was CXCL10 with a p-value=0.00004 (FIG. 2A and Table 3).

CXCL10 and IL-8 were significant to measure hepatocyte ballooning (NAS scoring system) with p-values <0.05 (FIG. 3 and Table 3).

None of the 6 biomarkers were significant to measure steatosis (Table 3).

Fibrosis biomarkers: HA, IL-8 and CXCL10 were found to be deregulated in advanced fibrosis (F≥3) during NASH with significant p-values ≤0.05. Particularly, HA, allowed the best discrimination between a Brunt Score of F≥3 and a Brunt Score of F<3 with p=0.0001 and AUC=0.924 (FIG. 4A and Table 2b).
2. Model-Building—2 in 1 Diagnostics of NASH and Advanced Fibrosis Assessment:
On basis of the results obtained for NASH diagnostic and fibrosis assessment in NASH patients, we designed a global scoring system with eighteen mathematical algorithms to simultaneously distinguish patients with and without NASH and NASH patients with and without advanced fibrosis.

According to the best univariate results, we identified a core of biomarkers composed of HA, CXCL10 and IL-8 allowing significant discrimination between NASH and NAFL, as well as a hepatic fibrosis status corresponding to a Brunt Score of F≥3 and a Brunt Score of F<3 ("NASH" and "fibrosis"). All the combinations of biomarkers presenting this core have been evaluated. We selected eighteen signatures presented in Tables 4a, 4b, 5a and 5b allowing significant diagnostic of NASH and fibrosis staging of NASH patients.

The diagnostic performances obtained with the "NASH" algorithms are as follow: AUCs=[0.794-0.881], accuracy= [0.75-0.82], Se=[0.58-0.97], Sp=[0.64-0.92], PPV=[0.77-0.88], NPV=[0.68-0.94]. These diagnostic performances are better than the ones obtained with commercially or free available non-invasive fibrosis tests (the best one is APRI with AUC=0.653, accuracy=0.68, Se=0.76, Sp=0.59, PPV=0.67 and NPV=0.7) (Table 6).

The diagnostic performances obtained with "fibrosis" algorithms reached values between: AUCs=[0.971-1], accuracy=[0.89-1], Se=[0.95-1], Sp=[0.79-1], PPV=[0.83-1], NPV=[0.93-1]. These diagnostic performances are better than the ones obtained with commercially or free available non-invasive fibrosis tests (the best one is Fibroscan® with AUC=0.903, accuracy=0.87, Se=0.95, Sp=0.76, PPV=0.83 and NPV=0.93) (Table 7).

These performances have been obtained from the whole data. To evaluate the risk of over-fitting we performed cross-validation analysis. Results are presented in Tables 4a, 4b, 5a and 5b. The 10 fold-cross validation approach was used for the evaluation of performances in "NASH" and "fibrosis". The performances (AUC, Se, Sp) from the test (whole data) and train (cross-validation) sets are presented in Tables 4a, 4b, 5a and 5b. The performances obtained on train sets are summarized as averages and intervals [min-max]. Overall, diagnostic performances obtained on the cross-validation data sets confirmed the robustness of those obtained on the whole data, whereas, as expected, a minor decrease is observed on the test set performances. In Tables 4a and 4b, coefficient ranges of all the logistic regression models corresponding to the signatures of Tables 4a and 4b are described.

As an example, among the 18 algorithms proposed for NASH diagnostic and fibrosis assessment (Tables 4 and 5), the regression formula for the diagnostic of NASH based on 3 common biomarkers levels including IL-8, HA and CXCL10 can be as follows:

$$f_{1(NASH)} = \frac{\exp(y_{1(NASH)})}{1 + \exp(y_{1(NASH)})} \text{ wherein } f_{1(NASH)}:$$ [Formula (13)]

$$(y_{1(NASH)}) = (-2.3083 +$$ [Formula (14)]

$$0.4079 \times IL8 - 0.0129 \times HA + 0.0019 \times CXCL10) \text{ and}$$

$$f_{1(fibrosis)} = \frac{\exp(y_{1(fibrosis)})}{1 + \exp(y_{1(fibrosis)})} \text{ where}$$ [Formula (15)]

-continued $$(y_{1(fibrosis)}) =$$ [Formula (16)]

$$(-7.0457 + 1.0511 \times IL8 + 0.067 \times HA + 0.0004 \times CXCL10),$$

respectively.

According to the threshold defined as the cut-off of the Youden method (0.4997 for "NASH" and 0.1953 for "fibrosis"), the diagnostic accuracy of the test for NASH was 76%, Se 69%, Sp 84%, PPV 82% and NPV 72% (Table 4). For advanced fibrosis assessment in NASH patients, the best diagnostic accuracy of the test was 92%, Se 100%, Sp 84%, PPV 87%, NPV 100% (Table 5).

In the example, when $f_{1(NASH)} > 0.4997$, the patient will be diagnosed NASH and when $f_{1(NASH)} \leq 0.4997$, the patient will be diagnosed NAFL (Table 4).

Similarly, when $f_{1(fibrosis)} > 0.1953$, the stage of liver fibrosis of the patient is advanced (F≥3) and if $f_{1(fibrosis)} \leq 0.1953$, the stage of liver fibrosis for the patient is determined to be early-moderate (F<3) (Table 5).

In Tables 8 and 9 (for NASH diagnosis and fibrosis staging, respectively), the same performances (Accuracy, Se, Sp, PPV and NPV) are listed for several thresholds (0.1, 0.2, 0.3, 0.4, 0.5, 0.6, 0.7, 0.8 and 0.9). The AUC is independent from the threshold selected.

TABLE 1

Patients characteristics. Comparison of clinico-demographic characteristics in study groups.

| Parameters | Groups NAFLD (n = 84) | NAFL (n = 40) | NASH (n = 44) | p-value |
|---|---|---|---|---|
| Age (year) | 56.7 ± 12.0 (18-74) | 58.1 ± 9.6 (27-71) | 55.3 ± 13.7 (18-74) | 0.4563 |
| Male sex | 46 (55%) | 23 (52%) | 23 (57%) | 0.7900 |
| Body Mass Index (kg/m$^2$) | 33.3 ± 5.7 (20.3-49.0) | 33.2 ± 5.0 (23.0-45.4) | 33.4 ± 6.4 (20.3-49.0) | 0.9126 |
| Waist circumference (cm) | 109 ± 13 (85-154) | 111 ± 12 (85-140) | 108 ± 14 (85-154) | 0.4070 |
| Diabetes (%)$^a$ | 60.7 | 60 | 61.4 | 0.8983 |
| Hypertension (%) | 66.6 | 70.0 | 63.0 | 0.7000 |
| Biopsy length (mm) | 21 ± 10 | 21 ± 11 | 21 ± 9 | NA |
| Steatosis (%) | 51 ± 20 (2-90) | 38 ± 17 (2-70) | 63 ± 14 (35-90) | <0.0001 |
| Fibrosis stages (%): | | | | |
| 0 | 4.8 | 10.0 | 0.0 | 0.1206 |
| 1 | 23.8 | 30.0 | 18.2 | 0.1206 |
| 2 | 29.8 | 27.5 | 31.8 | 0.1206 |
| 3 | 28.5 | 22.5 | 34.1 | 0.1206 |
| 4 | 13.1 | 10.0 | 15.9 | 0.1206 |
| NAS score (%) | | | | |
| 0 | 1.2 | 2.5 | 0.0 | <10e−14 |
| 1 | 2.4 | 5.0 | 0.0 | <10e−14 |
| 2 | 1.2 | 2.5 | 0.0 | <10e−14 |
| 3 | 19.0 | 40.0 | 0.0 | <10e−14 |
| 4 | 23.8 | 50.0 | 0.0 | <10e−14 |
| 5 | 33.3 | 0.00 | 63.6 | <10e−14 |
| 6 | 14.3 | 0.00 | 27.3 | <10e−14 |
| 7 | 4.8 | 0.00 | 9.1 | <10e−14 |
| Steatosis (%) | | | | |
| 0 | 1.2 | 2.5 | 0.0 | <10e−7 |
| 1 | 20.2 | 42.5 | 0.0 | <10e−7 |
| 2 | 50 | 52.5 | 47.7 | <10e−7 |
| 3 | 28.6 | 2.5 | 52.3 | <10e−7 |
| Hepatocyte ballooning (%) | | | | |
| 0 | 10.7 | 22.5 | 0.0 | <10e−06 |
| 1 | 52.4 | 67.5 | 38.6 | <10e−06 |
| 2 | 36.9 | 10.0 | 61.4 | <10e−06 |
| Lobular inflammation (%) | | | | |
| 0 | 7.1 | 15.0 | 0.0 | 0.0045 |
| 1 | 76.2 | 80.0 | 72.7 | 0.0045 |
| 2 | 15.5 | 5.0 | 25.0 | 0.0045 |

TABLE 1-continued

Patients characteristics. Comparison of clinico-demographic characteristics in study groups.

| | Groups NAFLD (n = 84) | NAFL (n = 40) | NASH (n = 44) | p-value |
|---|---|---|---|---|
| 3 | 1.2 | 0.0 | 2.3 | 0.0045 |
| ALT (IU/L) | 87 ± 111 (17-960) | 70 ± 64 (17-332) | 104 ± 140 (24-960) | 0.0024 |
| AST (IU/L) | 59 ± 68 (19-622) | 47 ± 28 (24-140) | 70 ± 90 (19-622) | 0.0038 |
| Platelets (g/L) | 205 ± 54 (81-347) | 206 ± 49 (140-344) | 204 ± 59 (81-347) | 0.8794 |
| Triglycerides (mmol/L) | 1.84 ± 1.10 (0.58-5.75) | 1.68 ± 0.93 (0.65-5.75) | 1.99 ± 1.22 (0.58-5.69) | 0.3095 |
| HDL cholesterol (mmol/L) | 1.12 ± 0.25 (0.54-2.01) | 1.17 ± 0.26 (0.55-1.72) | 1.08 ± 0.24 (0.54-2.01) | 0.0966 |
| GammaGT (IU/L) | 135 ± 178 (20-970) | 101 ± 107 (22-581) | 165 ± 220 (20-970) | 0.0789 |
| Glycemia (mol/L) | 6.9 ± 2.4 (2.6-14.4) | 6.7 ± 2.1 (4.0-12.0) | 7.0 ± 2.6 (2.6-14.4) | 0.7782 |
| LSM median (kPa)[b] | 11.8 ± 6.3 (4.3-38.6) | 10.7 ± 5.5 (4.3-30.6) | 12.8 ± 6.8 (5.3-38.6) | 0.1299 |

ALT: alanine aminotransferase;
AST: aspartate aminotransferase
LSM: Liver stiffness measurement by Fibroscan ®
[a] either diabetes treatment or fasting glycemia ≥ 126 mg/dl
[b] in the 84 patients with available results for liver stiffness

TABLE 2a

Biomarkers evaluated for the presence of NASH in study groups.

| Biomarkers | concentrations (serum) | Groups NAFLD (n = 84) | NAFL (n = 40) | NASH (n = 44) | p-value | q-value | n-fold | AUC | n patients |
|---|---|---|---|---|---|---|---|---|---|
| CXCL10 | pg/ml | 1032.68 ± 1484.47 | 724.63 ± 432.03 | 1311.39 ± 1977.39 * | 0.001 | 0.053 | 1.41 | 0.721 | n = 80 [38 (0); 42(1)] |
| ghrelin | pg/ml | 899.1 ± 589.61 | 1051.14 ± 634.44 | 768.79 ± 521.14 * | 0.031 | 0.249 | 0.72 | 0.642 | n = 78 [36 (0); 42 (1)] |
| IL-8 | pg/ml | 3.74 ± 2.97 | 2.87 ± 1.22 | 4.51 ± 3.77 | 0.067 | 0.3321 | 1.10 | 0.618 | n = 83 [39 (0); 44(1)] |
| HA | ng/ml | 52.89 ± 57.34 | 50.57 ± 59.8 | 55.16 ± 55.48 | 0.276 | 0.579 | 1.32 | 0.571 | n = 81 [40 (0); 41 (1)] |
| haptoglobin | mg/ml | 1.18 ± 0.57 | 1.23 ± 0.61 | 1.13 ± 0.53 | 0.485 | 0.736 | 0.87 | 0.544 | n = 84 [40 (0); 44 (1)] |
| pre-HP2 | ng/ml | 33.04 ± 88.34 | 39.08 ± 101.10 | 27.29 ± 75.01 | 0.732 | 0.895 | 0.95 | 0.522 | n = 82 [40 (0); 42 (1)] |

* Significant difference between study groups

TABLE 2b

Biomarkers evaluated for advanced fibrosis assessment in NASH population (F1-2 versus F3-4).

| Biomarkers | concentrations (serum) | Groups F1-2-3-4 (n = 44) | F1-2 (n = 22) | F3-F4 (n = 22) | p-value | q-value | n-fold | AUC | n patients |
|---|---|---|---|---|---|---|---|---|---|
| HA | ng/mL | 55.16 ± 55.48 | 25.33 ± 15.59 | 83.57 ± 64.72 * | 0.0001 | 0.004 | 3.32 | 0.924 | n = 41 [20 (0); 21 (1)] |
| IL-8 | pg/mL | 4.51 ± 3.77 | 2.41 ± 09 | 6.6 ± 4.37 * | <10e−04 | <10e−04 | 2.48 | 0.893 | n = 44 [22 (0); 22(1)] |
| CXCL10 | pg/mL | 1311.39 ± 1977.39 | 891.85 ± 432.20 | 1731.19 ± 2731.08 * | 0.057 | 0.193 | 1.32 | 0.673 | n = 42 [21 (0); 21 (1)] |
| pre-HP2 | ng/mL | 27.29 ± 75.01 | 8.70 ± 10.59 | 47.73 ± 105.73 | 0.128 | 0.333 | 2.08 | 0.640 | n = 42 [22 (0); 20(1)] |
| haptoglobin | mg/mL | 1.13 ± 0.53 | 1.21 ± 0.46 | 1.04 ± 0.59 | 0.283 | 0.578 | 0.89 | 0.616 | n = 44 [22 (0); 22 (1)] |
| ghrelin | pg/mL | 768.79 ± 521.14 | 774.49 ± 421.86 | 762.52 ± 623.91 | 0.585 | 0.762 | 0.65 | 0.552 | n = 42 [22 (0); 20(1)] |

* Significant difference between study groups

TABLE 3

Steatosis. Inflammation and Ballooning biomarkers - NAS scoring system.

| Inflammation (Kleiner) Biomarker | p-value | Ballooning (Kleiner) Biomarker | p-value | Steatosis (Kleiner) Biomarker | p-value |
|---|---|---|---|---|---|
| CXCL10 | 0.00004* | CXCL10 | 0.029* | haptoglobin | 0.060 |
| ALAT | 0.00005* | IL-8 | 0.041* | ghrelin | 0.127 |
| ASAT | 0.00010* | ghrelin | 0.093 | HA | 0.344 |
| IL-8 | 0.006* | HA | 0.272 | pre-HP2 | 0.373 |
| pre-HP2 | 0.009* | pre-HP2 | 0.972 | IL-8 | 0.521 |
| HA | 0.072 | haptoglobin | 0.911 | CXCL10 | 0.881 |
| ghrelin | 0.880 | | | | |
| haptoglobin | 0.672 | | | | |

TABLE 4a

NASH diagnostic performances of y1 to y5 signatures.

| | NASH Diagnostic | y1 = a1 + a2 × [IL8 (pg/ml)] + a3 × [HA (ng/ml) + a4 × [CXCL10 (pg/ml)] | y2 = a1 + a2 × [IL8 (pg/ml)] + a3 × [HA (ng/ml)] + a4 × [CXCL10 (pg/ml)] + a5 × [ghrelin (pg/ml)] | y3 = a1 + a2 × [IL8 (pg/ml)] + a3 × [HA (ng/ml) + a4 × [CXCL10 (pg/ml)] + a5 × pre-HP2 (ng/ml)] | y4 = a1 + a2 × [IL8 (pg/ml) + a3 × [HA (ng/ml) + a4 × [CXCL10 (pg/ml)] + a5 × [liver stiffness(kPa)] | y5 = a1 + a2 × [IL8 (pg/ml)] + a3 × [HA(ng/ml)] + a4 × [CXCL10 (pg/ml)] + a5 × [ghrelin (pg/ml)] + a6 × [pre-HP2 (ng/ml)] |
|---|---|---|---|---|---|---|
| Whole data | AUC | 0.795 | 0.817 | 0.794 | 0.828 | 0.826 |
| | Accuracy | 0.76 | 0.81 | 0.75 | 0.79 | 0.81 |
| | Sensitivity | 0.69 | 0.89 | 0.58 | 0.73 | 0.82 |
| | Specificity | 0.84 | 0.71 | 0.92 | 0.86 | 0.79 |
| | PPV | 0.82 | 0.77 | 0.88 | 0.86 | 0.82 |
| | NPV | 0.72 | 0.86 | 0.68 | 0.73 | 0.79 |
| | Threshold | 0.4997 | 0.4805 | 0.5825 | 0.5045 | 0.5076 |
| | a1 | −2.3083 | −1.5071 | −2.2705 | −2.8912 | −1.5043 |
| | a2 | 0.4079 | 0.4588 | 0.3919 | 0.5165 | 0.4412 |
| | a3 | −0.0129 | −0.0134 | −0.0126 | −0.0153 | −0.0133 |
| | a4 | 0.0019 | 0.0021 | 0.002 | 0.0019 | 0.0022 |
| | a5 | NA | −0.0011 | −0.0021 | 0.0257 | −0.0011 |
| | a6 | NA | NA | NA | NA | −0.002 |
| | Nb. of patients | 76 | 72 | 75 | 61 | 72 |
| Cross validation | AUC_Test | 0.75 | 0.735 | 0.713 | 0.753 | 0.707 |
| | AUC_Train_mean | 0.794 | 0.818 | 0.796 | 0.833 | 0.83 |
| | ([min; max]) | ([0.758; 0.827]) | ([0.778; 0.866]) | ([0.763; 0.832]) | ([0.808; 0.864]) | ([0.786; 0.883]) |
| | Se_Test | 0.641 | 0.816 | 0.605 | 0.727 | 0.421 |
| | Se_Train_mean | 0.685 | 0.874 | 0.683 | 0.728 | 0.841 |
| | ([min; max]) | ([0.576; 0.8381]) | ([0.818; 0.914]) | ([0.562; 0.8611]) | ([0.633; 0.9]) | ([0.758; 0.943]) |
| | Sp_Test | 0.811 | 0.588 | 0.811 | 0.821 | 0.941 |
| | Sp_Train_mean | 0.858 | 0.709 | 0.846 | 0.858 | 0.767 |
| | ([min; max]) | ([0.719; 0.938]) | ([0.645; 0.781]) | ([0.719; 0.938]) | ([0.68; 0.96]) | ([0.7; 0.844]) |
| | Range_a1 | [−3.1745; −2.0093] | [−2.4468; −1.0735] | [−7.6186; −2.677] | [−3.6496; −2.6069] | [−2.5024; −0.7343] |
| | Range_a2 | [ 0.349; 0.5662] | [0.3854; 0.6238] | [0.3312; 0.5497] | [0.4069; 0.6739] | [0.37; 0.6096] |
| | Range_a3 | [−0.0193; −0.0099] | [−0.0231; −0.0102] | [−0.0186; −0.0099] | [−0.0235; −0.0096] | [−0.0227; −0.0098] |
| | Range_a4 | [0.0015; 0.003] | [0.0017; 0.003] | [0.0016; 0.0032] | [0.0016; 0.0026] | [0.0018; 0.0033] |
| | Range_a5 | NA | [−0.0014; −9e−04] | [−0.0058; −9e−04] | [−0.0186; 0.1113] | [−0.0017; −9e−04] |
| | Range_a6 | NA | NA | NA | NA | [−0.0212; 5e−04] |
| | Range_Threshold | [0.41; 0.60] | [0.45; 0.51] | [0.41; 0.61] | [0.35; 0.74] | [0.45; 0.53] |
| | Range_a1_rounded | [−4; −2] | [−3; −1] | [−8; −2] | [−4; −2] | [−3; 0] |
| | Range_a2_rounded | [0; 1] | [0; 1] | [0; 1] | [0; 1] | [0; 1] |
| | Range_a3_rounded | [−1; 0] | [−1; 0] | [−1; 0] | [−1; 0] | [−1; 0] |
| | Range_a4_rounded | [0; 1] | [0; 1] | [0; 1] | [0; 1] | [0; 1] |
| | Range_a5_rounded | NA | [−1; 0] | [−1; 0] | [−1; 1] | [−1; 0] |
| | Range_a6_rounded | NA | NA | NA | NA | [−1; 1] |
| | Range_Threshold_rounded | [0.4; 0.6] | [0.4; 0.6] | [0.4; 0.7] | [0.3; 0.8] | [0.4; 0.6] |
| | Range_a1_rounded_global | [−9; 12] | [−9; 12] | [−9; 12] | [−9; 12] | [−9; 12] |
| | Range_a2_rounded_global | [0; 2] | [0; 2] | [0; 2] | [0; 2] | [0; 2] |
| | Range_a3_rounded_global | [−1; 2] | [−1; 2] | [−1; 2] | [−1; 2] | [−1; 2] |
| | Range_a4_rounded_global | [−1; 1] | [ −1; 1 ] | [−1; 1] | [−1; 1] | [−1; 1] |
| | Range_a5_rounded_global | NA | [−1; 1] | [−1; 1] | [−1; 1] | [−1; 1] |
| | Range_a6_rounded_global | NA | NA | NA | NA | [−1; 1] |
| | Range_Threshold_rounded_global | [0.2; 0.8] | [0.2; 0.8] | [0.2; 0.8] | [0.2; 0.8] | [0.2; 0.8] |
| | Nb. of patients | 76 | 72 | 75 | 61 | 72 |

TABLE 4b

| | NASH diagnostic Performances of y6 to y9 signatures. | |
|---|---|---|
| NASH Diagnostic | y6 = a1 + a2 × [IL8(pg/ml)] + a3 × [HA(ng/ml)] + a4 × [CXCL10(pg/ml)] + a5 × [ghrelin (pg/ml)] + a6 × [liver stiffness(kPa)] | y7 = a1 + a2 × [IL8(pg/ml)] + a3 × [HA(ng/ml) + a4 × [CXCL10(pg/ml)] + a5 × [pre-HP2 (ng/ml)] + a6 × [liver stiffness(kPa)] |

| | NASH Diagnostic | | |
|---|---|---|---|
| Whole data | AUC | 0.876 | 0.823 |
| | Accuracy | 0.82 | 0.78 |
| | Sensitivity | 0.97 | 0.72 |
| | Specificity | 0.64 | 0.86 |
| | PPV | 0.78 | 0.85 |
| | NPV | 0.94 | 0.73 |
| | Threshold | 0.3715 | 0.5045 |
| | a1 | −3.4372 | −2.8898 |
| | a2 | 0.6117 | 0.5162 |
| | a3 | −0.0226 | −0.0153 |
| | a4 | 0.0026 | 0.0019 |
| | a5 | −0.0016 | −0.0001 |
| | a6 | 0.1754 | 0.0256 |
| | a7 | NA | NA |
| | a8 | NA | NA |
| | a9 | NA | NA |
| | a10 | NA | NA |
| | a11 | NA | NA |
| | a12 | NA | NA |
| | Nb. of patients | 57 | 60 |
| Cross validation | AUC_Test | 0.731 | 0.703 |
| | AUC_Train_mean ([min; max]) | 0.883 ([0.859; 0.956]) | 0.83 ([0.806; 0.86]) |
| | Se_Test | 0.875 | 0.656 |
| | Se_Train_mean ([min; max]) | 0.897 ([0.759; 1]) | 0.74 ([0.655; 0.897]) |
| | Sp_Test | 0.48 | 0.821 |
| | Sp_Train_mean ([min; max]) | 0.748 ([0.591; 0.909]) | 0.834 ([0.68; 0.92]) |
| | Range_a1 | [−3.1549; −1.9706] | [−3.6324; −2.5267] |
| | Range_a2 | [0.4606; 1.3785] | [0.4132; 0.6902] |
| | Range_a3 | [−0.0552; −0.0141] | [−0.0248; −0.0094] |
| | Range_a4 | [0.0019; 0.0073] | [0.0016; 0.0027] |
| | Range_a5 | [−0.003; −8e−04] | [−0.0054; 0.0019] |
| | Range_a6 | [0.1219; 0.2986] | [−0.0281; 0.1092] |
| | Range_a7 | NA | NA |
| | Range_a8 | NA | NA |
| | Range_a9 | NA | NA |
| | Range_a10 | NA | NA |
| | Range_a11 | NA | NA |
| | Range_a12 | NA | NA |
| | Range_Threshold | [0.35; 0.55] | [0.35; 0.64] |
| Cross validation | Range_a1_rounded | [−4; −1] | [−4; −2] |
| | Range_a2_rounded | [0; 2] | [0; 1] |
| | Range_a3_rounded | [−1; 0] | [−1; 0] |
| | Range_a4_rounded | [0; 1] | [0; 1] |
| | Range_a5_rounded | [−1; 0] | [−1; 1] |
| | Range_a6_rounded | [0; 1] | [−1; 1] |
| | Range_a7_rounded | NA | NA |
| | Range_a8_rounded | NA | NA |
| | Range_a9_rounded | NA | NA |
| | Range_a10_rounded | NA | NA |
| | Range_a11_rounded | NA | NA |
| | Range_a12_rounded | NA | NA |
| | Range_Threshold_rounded | [0.3; 0.6] | [0.3; 0.7] |
| Cross validation | Range_a1_rounded_global | [−9; 12] | [−9; 12] |
| | Range_a2_rounded_global | [0; 2] | [0; 2] |
| | Range_a3_rounded_global | [−1; 2] | [−1; 2] |
| | Range_a4_rounded_global | [−1; 1] | [−1; 1] |
| | Range_a5_rounded_global | [−1; 1] | [−1; 1] |
| | Range_a6_rounded_global | [−1; 1] | [−1; 1] |
| | Range_a7_rounded_global | NA | NA |
| Cross validation | Range_a8_rounded_global | NA | NA |
| | Range_a9_rounded_global | NA | NA |

TABLE 4b-continued

NASH diagnostic Performances of y6 to y9 signatures.

| | | | |
|---|---|---|---|
| Range_a10_rounded_global | | NA | NA |
| Range_a11_rounded_global | | NA | NA |
| Range_a12_rounded_global | | NA | NA |
| Range Threshold_rounded_global | | [0.2; 0.8] | [0.2; 0.8] |
| Number of patients | | 57 | 60 |

| NASH Diagnostic | | y8 = a1 + a2 × [IL8(pg/ml)] + a3 × [HA(ng/ml) + a4 × [CXCL10(pg/ml)] + a5 × [ghrelin](pg/ml)] + a6 × [pre-HP2 (ng/ml)] + a7 × [liver stiffness(kPa)] | y9 = a1 + a2 × [IL8(pg/ml)] + a3 × [HA(ng/ml)] + a4 × [CXCL10(pg/ml)] + a5 × [ghrelin (pg/ml)] + a6 × [pre-HP2(ng/ml)] + a7 × [Haptoglobin(mg/ml)] + a8 × [liver stiffness (kPa)] + a9 × [age(year)] + a10 × [sex(m/f)] + a11 × [BMI(kg/m2)] + a12 × [hypertension (yes = 1; no = 0)] |
|---|---|---|---|
| Whole data | AUC | 0.871 | 0.881 |
| | Accuracy | 0.79 | 0.8 |
| | Sensitivity | 0.78 | 0.74 |
| | Specificity | 0.8 | 0.88 |
| | PPV | 0.83 | 0.88 |
| | NPV | 0.74 | 0.73 |
| | Threshold | 0.5219 | 0.6459 |
| | a1 | −3.4336 | 1.923 |
| | a2 | 0.6348 | 0.6463 |
| | a3 | −0.0236 | −0.0184 |
| | a4 | 0.0025 | 0.0022 |
| | a5 | −0.0017 | −0.0016 |
| | a6 | 0.0024 | 0.0022 |
| | a7 | 0.185 | 0.4652 |
| | a8 | NA | 0.1706 |
| | a9 | NA | −0.059 |
| | a10 | NA | −0.6246 |
| | a11 | NA | −0.0745 |
| | a12 | NA | 0.2851 |
| | Nb. of patients | 57 | 56 |
| Cross validation | AUC_Test | 0.715 | 0.644 |
| | AUC_Train_mean ([min; max]) | 0.879 ([0.847; 0.958]) | 0.897 ([0.869; 0.959]) |
| | Se_Test | 0.938 | 0.903 |
| | Se_Train_mean ([min; max]) | 0.874 ([0.759; 1]) | 0.856 ([0.759; 1]) |
| | Sp_Test | 0.44 | 0.4 |
| | Sp_Train_mean ([min; max]) | 0.762 ([0.591; 0.913]) | 0.801 ([0.583; 0.955]) |
| | Range_a1 | [−8.0532; −2.5597] | [−7.6074; 11.4188] |
| | Range_a2 | [0.1138; 0.2938] | [0.5081; 1.6283] |
| | Range_a3 | [0.5195; 1.4246] | [−0.0523; −0.0032] |
| | Range_a4 | [−0.0029; −0.001] | [0.0016; 0.0086] |
| | Range_a5 | [−0.0061; 0.0072] | [−0.0032; −0.001] |
| | Range_a6 | [−0.0563; −0.0149] | [−0.0138; 0.0075] |
| | Range_a7 | [0.0017; 0.0079] | [−0.2328; 0.8342] |
| | Range_a8 | NA | [−0.1062; 0.3262] |
| | Range_a9 | NA | [−0.1246; 0.0268] |
| | Range_a10 | NA | [−2.1462; 1.1405] |
| | Range_a11 | NA | [−0.1945; 0.0205] |
| | Range_a12 | NA | [−0.1716; 0.4732] |
| | Range_Threshold | [0.33; 0.57] | [0.27; 0.68] |
| Cross validation | Range_a1_rounded | [−9; −2] | [−8; 12] |
| | Range_a2_rounded | [0; 1] | [0; 2] |
| | Range_a3_rounded | [0; 2] | [−1; 0] |
| | Range_a4_rounded | [−1; 0] | [0; 1] |
| | Range_a5_rounded | [−1; 1] | [−1; 0] |
| | Range_a6_rounded | [−1; 0] | [−1; 1] |
| | Range_a7_rounded | [0; 1] | [−1; 1] |
| | Range_a8_rounded | NA | [−1; 1] |
| | Range_a9_rounded | NA | [−1; 1] |
| | Range_a10_rounded | NA | [−3; 2] |
| | Range_a11_rounded | NA | [−1; 1] |
| | Range_a12_rounded | NA | [−1; 1] |
| | Range_Threshold_rounded | [0.3; 0.6] | [0.2; 0.7] |
| Cross validation | Range_a1_rounded_global | [−9; 12] | [−9; 12] |
| | Range_a2_rounded_global | [0; 2] | [0; 2] |

TABLE 4b-continued

| NASH diagnostic Performances of y6 to y9 signatures. | | | |
|---|---|---|---|
| | Range_a3_rounded_global | [−1; 2] | [−1; 2] |
| | Range_a4 _rounded_global | [−1; 1] | [−1; 1] |
| | Range_a5_rounded_global | [−1; 1] | [−1; 1] |
| | Range_a6_rounded_global | [−1; 1] | [−1; 1] |
| | Range_a7_rounded_global | [−1; 1] | [−1; 1] |
| Cross validation | Range_a8_rounded_global | NA | [−1; 1] |
| | Range_a9_rounded_global | NA | [−1; 1] |
| | Range_a10_rounded_global | NA | [−3; 2] |
| | Range_a11_rounded_global | NA | [−1; 1] |
| | Range_a12_rounded_global | NA | [−1; 1] |
| | Range Threshold_rounded_global | [0.2; 0.8] | [0.2; 0.8] |
| | Number of patients | 57 | 56 |

TABLE 5a

| Fibrosis diagnostic performances of y1 to y5 signatures. | | | | | | |
|---|---|---|---|---|---|---|
| | Advanced fibrosis (F ≥ 3) staging in NASH patients | $y1 = a2 + a2 \times [IL8 (pg/ml)] + a3 \times [HA (ng/ml) + a4 \times [CXCL10 (pg/ml)]$ | $y2 = a1 + a2 \times [IL8 (pg/ml)] + a3 \times [HA (ng/ml)] + a4 \times [CXCL10 (pg/ml)] + a5 \times [ghrelin (pg/ml)]$ | $y3 = a1 + a2 \times [IL8 (pg/ml)] + a3 \times [HA (ng/ml) + a4 \times [CXCL10 (pg/ml)] + a5 \times [pre-HP2(ng/ml)]$ | $y4 = a1 + a2 \times [IL8 (pg/ml)] + a3 \times [HA (ng/ml) + a4 \times [CXCL10 (pg/ml)] + a5 \times [liver stiffness(kPa)]$ | $y5 = a1 + a2 \times [IL8 (pg/ml) + a3 \times [HA(ng/ml)] + a4 \times [CXCL10 (pg/ml) + a5 \times [ghrelin (pg/ml) + a6 \times [pre-HP2 (ng/ml)]$ |
| Whole data | AUC | 0.971 | 0.972 | 0.989 | 0.977 | 0.986 |
| | Accuracy | 0.92 | 0.89 | 0.97 | 0.94 | 0.97 |
| | Sensitivity | 1 | 1 | 0.95 | 0.95 | 0.95 |
| | Specificity | 0.84 | 0.79 | 1 | 0.93 | 1 |
| | PPV | 0.87 | 0.83 | 1 | 0.95 | 1 |
| | NPV | 1 | 1 | 0.95 | 0.93 | 0.95 |
| | Threshold | 0.1953 | 0.1253 | 0.6804 | 0.5739 | 0.6569 |
| | a1 | −7.0457 | −8.0563 | −15.0639 | −12.4379 | −15.1894 |
| | a2 | 1.0511 | 1.1882 | 1.939 | 1.0006 | 1.9014 |
| | a3 | 0.067 | 0.0632 | 0.1244 | 0.0506 | 0.1216 |
| | a4 | 0.0004 | −0.0002 | −0.0001 | 0.0014 | −0.0003 |
| | a5 | NA | 0.0013 | 0.2064 | 0.4287 | 0.0008 |
| | a6 | NA | NA | NA | NA | 0.2056 |
| | Nb. of patients | 39 | 38 | 32 | 33 | 38 |
| Cross validation | AUC_Test | 0.837 | 0.812 | 0.917 | 0.821 | 0.801 |
| | AUC_Train_mean ([min; max]) | 0.971 ([0.962; 0.983]) | 0.971 ([0.961; 1]) | 1 ([1; 1]) | 0.978 ([0.966; 1]) | 0.988 ([0.984; 1]) |
| | Se_Test | 0.85 | 0.947 | 0.944 | 0.947 | 0.895 |
| | Se_Train_mean ([min; max]) | 0.958 ([0.833; 1]) | 0.905 ([0.789; 1]) | 1 ([1; 1]) | 0.958 ([0.938; 1]) | 0.953 ([0.938; 1]) |
| | Sp_Test | 0.789 | 0.684 | 0.857 | 0.857 | 0.789 |
| | Sp_Train_mean ([min; max]) | 0.874 ([0.778; 1]) | 0.924 ([0.789; 1]) | 1 ([1; 1]) | 0.929 ([0.833; 1]) | 1 ([1; 1]) |
| | Range_a1 | [−73.4992; −6.4293] | [−3006.4383; −7.3732] | [−412.5449; −124.0861] | [−468.1446; −11.0431] | [−305.2863; −9.7599] |
| | Range_a2 | [0.8913; 18.7878] | [0.9785; 766.7965] | [1.4646; 87.3698] | [0.8588; 46.1798] | [1.4743; 90.0898] |
| | Range_a3 | [0.0457; 0.0966] | [0.0483; 2.3918] | [0.0984; 1.6025] | [0.0424; 1.0993] | [0.0695; 1.0314] |
| | Range_a4 | [−0.0012; 0.0136] | [−0.0029; 0.2815] | [−0.0769; 0.001] | [−0.1296; 0.0381] | [−0.1144; 7e−04] |
| | Range_a5 | NA | [8e−04; 0.268] | [0.1459; 3.3263] | [0.3089; 27.2016] | [−0.0057; 0.0238] |
| | Range_a6 | NA | NA | NA | NA | [0.0668; 2.112] |

TABLE 5a-continued

Fibrosis diagnostic performances of y1 to y5 signatures.

| Advanced fibrosis (F ≥ 3) staging in NASH patients | y1 = a2 + a2 × [IL8 (pg/ml)] + a3 × [HA (ng/ml) + a4 × [CXCL10 (pg/ml)] | y2 = a1 + a2 × [IL8 (pg/ml)] + a3 × [HA (ng/ml) + a4 × [CXCL10 (pg/ml)] + a5 [ghrelin (pg/ml)] | y3 = a1 + a2 × [IL8 (pg/ml) + a3 × [HA (ng/ml) + a4 × [CXCL10 (pg/ml)] + a5 × [pre-HP2(ng/ml)] | y4 = a1 + a2 × [IL8 (pg/ml) + a3 × [HA (ng/ml) + a4 × [CXCL10 (pg/ml)] + a5 × [liver stiffness(kPa)] | y5 = a1 + a2 × [IL8 (pg/ml) + a3 × [HA(ng/ml)] + a4 × [CXCL10 (pg/ml) + a5 [ghrelin (pg/ml)] + a6 [pre-HP2 (ng/ml)] |
|---|---|---|---|---|---|
| Range_Threshold | [0.153; 0.8063] | [0.1312; 0.7744] | [0.5; 0.5] | [0.234; 0.5805] | [0.5; 0.76] |
| Range_a1_rounded | [−74; −6] | [−3007; −7] | [−413; −124] | [−469; −11] | [−306; −9] |
| Range_a2_rounded | [0; 19] | [0; 767] | [1; 88] | [0; 47] | [1; 91] |
| Range_a3_rounded | [0; 1] | [0; 3] | [0; 2] | [0; 2] | [0; 2] |
| Range_a4_rounded | [−1; 1] | [−1; 1] | [−1; 1] | [−1; 1] | [−1; 0] |
| Range_a5_rounded | NA | [0; 1] | [0; 4] | [0; 28] | [−1; 1] |
| Range_a6_rounded | NA | NA | NA | NA | [0; 3] |
| Range_Threshold_rounded | [0.1; 0.9] | [0.1; 0.8] | [0.5; 0.5] | [0.2; 0.6] | [0.5; 0.8] |
| Range_a1_rounded_global | [−20127; −2] | [−20127; −2] | [−20127; −2] | [−20127; −2] | [−20127; −2] |
| Range_a2_rounded_global | [0; 1459] | [0; 1459] | [0; 1459] | [0; 1459] | [0; 1459] |
| Range_a3_rounded_global | [−1; 129] | [−1; 129] | [−1; 129] | [−1; 129] | [−1; 129] |
| Range_a4_rounded_global | [−24; 1] | [−24; 1] | [−24; 1] | [−24; 1] | [−24; 1] |
| Range_a5_rounded_global | NA | [1; 11] | [−4; 4] | [−1; 462] | [−1; 11] |
| Range_a6_rounded_global | NA | NA | NA | NA | [−4; 4] |
| Range_Threshold_rounded_global | [0.1; 0.9] | [0.1; 0.9] | [0.1; 0.9] | [0.1; 0.9] | [0.1; 0.9] |
| Nb. of patients | 39 | 38 | 32 | 33 | 38 |

TABLE 5b

Fibrosis diagnostic performances of y6 to y9 signatures.

| | Advanced fibrosis (F ≥ 3) staging in NASH patients | y6 = a1 + a2 × [IL8(pg/ml)] + a3 × [HA(ng/ml)] + a4 × [CXCL10(pg/ml)] + a5 × [ghrelin (pg/ml)] + a6 × [liver stiffness(kPa)] | y7 = a1 + a2 × [IL8(pg/ml)] + a3 × [HA(ng/ml)] + a4 × [CXCL10(pg/ml)] + a5 × [pre-HP2 (ng/ml)] + a6 × [liver stiffness(kPa)] |
|---|---|---|---|
| Whole data | AUC | 0.98 | 1 |
| | Accuracy | 0.97 | 1 |
| | Sensitivity | 1 | 1 |
| | Specificity | 0.93 | 1 |
| | PPV | 0.95 | 1 |
| | NPV | 1 | 1 |
| | Threshold | 0.4918 | 0.5 |
| | a1 | −21.6802 | −406.8355 |
| | a2 | 1.6422 | 50.1074 |
| | a3 | 0.0809 | 0.374 |
| | a4 | −0.0015 | −0.1373 |
| | a5 | 0.0053 | 0.7089 |
| | a6 | 0.7117 | 23.9575 |
| | a7 | NA | NA |
| | a8 | NA | NA |
| | a9 | NA | NA |
| | a10 | NA | NA |
| | a11 | NA | NA |
| | a12 | NA | NA |
| | Nb. of patients | 38 | 32 |
| Cross validation | AUC_Test | 0.795 | 0.782 |
| | AUC_Train_mean ([min; max]) | 0.99 ([0.984; 1]) | 0.984 ([0.975; 1]) |
| | Se_Test | 0.947 | 0.833 |
| | Se_Train_mean ([min; max]) | 0.953 ([0.938; 1]) | 1 ([1; 1]) |
| | Sp_Test | 0.737 | 0.857 |
| | Sp_Train_mean ([min; max]) | 1 ([1; 1]) | 0.945 ([0.909; 1]) |
| | Range_a1 | [−314.0971; −11.7767] | [−20126.2324; −18.5857] |
| | Range_a2 | [1.4062; 1458.4597] | [11.6623; 50.9885] |
| | Range_a3 | [0.0634; 128.6227] | [−0.0717; 1.0477] |
| | Range_a4 | [−3.0809; 0.0128] | [−0.1398; 0.0137] |
| | Range_a5 | [−0.0262; 5.6201] | [0.1395; 3.2482] |
| | Range_a6 | [0.5584; 461.8513] | [4.4102; 24.3227] |
| | Range_a7 | NA | NA |
| | Range_a8 | NA | NA |
| | Range_a9 | NA | NA |
| | Range_a10 | NA | NA |

TABLE 5b-continued

Fibrosis diagnostic performances of y6 to y9 signatures.

| | | |
|---|---|---|
| Range_a11 | NA | NA |
| Range_a12 | NA | NA |
| Range_Threshold | [0.5; 0.7482] | [0.4044; 0.5] |
| Range_a1_rounded | [−315; −11] | [−20127; −18] |
| Range_a2_rounded | [1; 1459] | [11; 51] |
| Range_a3_rounded | [0; 129] | [−1; 2] |
| Range_a4_rounded | [−4; 1] | [−1; 1] |
| Range_a5_rounded | [−1; 6] | [0; 4] |
| Range_a6_rounded | [0; 462] | [4; 25] |
| Range_a7_rounded | NA | NA |
| Range_a8_rounded | NA | NA |
| Range_a9_rounded | NA | NA |
| Range_a10_rounded | NA | NA |
| Range_a11_rounded | NA | NA |
| Range_a12_rounded | NA | NA |
| Range_Threshold_rounded | [0.5; 0.8] | [0.4; 0.5] |
| Range_a1_rounded_global | [−20127; −2] | [−20127; −2] |
| Range_a2_rounded_global | [0; 1459] | [0; 1459] |
| Range_a3_rounded_global | [−1; 129] | [−1; 129] |
| Range_a4_rounded_global | [−24; 1] | [−24; 1] |
| Range_a5_rounded_global | [−1; 11] | [−4; 4] |
| Range_a6_rounded_global | [−1; 462] | [−1; 462] |
| Range_a7_rounded_global | NA | NA |
| Range_a8_rounded_global | NA | NA |
| Range_a9_rounded_global | NA | NA |
| Range_a10_rounded_global | NA | NA |
| Range_a11_rounded_global | NA | NA |
| Range_a12_rounded_global | NA | NA |
| Range Threshold_rounded_global | [0.1; 0.9] | [0.1; 0.9] |
| Number of patients | 38 | 32 |

| | | Advanced fibrosis (F ≥ 3) staging in NASH patients | $y8 = a1 + a2 \times [\text{IL8(pg/ml)}] + a3 \times [\text{HA(ng/ml)}] + a4 \times [\text{CXCL10(pg/ml)}] + a5 \times [\text{ghrelin}](\text{pg/ml})] + a6 \times [\text{pre-HP2(ng/ml)}] + a7 \times [\text{liver stiffness(kPa)}]$ | $y9 = a1 + a2 \times [\text{IL8(pg/ml)}] + a3 \times [\text{HA(ng/ml)}] + a4 \times [\text{CXCL10(pg/ml)}] + a5 \times [\text{ghrelin (pg/ml)}] + a6 \times [\text{pre-HP2(ng/ml)}] + a7 \times [\text{Haptoglobin(mg/ml)}] + a8 \times [\text{liver stiffness (kPa)}] + a9 \times [\text{age(year)}] + a10 \times [\text{sex(m/f)}] + a11 \times [\text{BMI(kg/m2)}] + a12 \times [\text{hypertension (yes = 1; no = 0)}]$ |
|---|---|---|---|---|
| Whole data | AUC | | 1 | 1 |
| | Accuracy | | 1 | 1 |
| | Sensitivity | | 1 | 1 |
| | Specificity | | 1 | 1 |
| | PPV | | 1 | 1 |
| | NPV | | 1 | 1 |
| | Threshold | | 0.5 | 0.5 |
| | a1 | | −224.2621 | −18.9141 |
| | a2 | | 34.2028 | 7.1292 |
| | a3 | | 0.1586 | 0.0633 |
| | a4 | | −0.087 | −0.0017 |
| | a5 | | −0.0283 | −0.0212 |
| | a6 | | 2.3234 | 0.1977 |
| | a7 | | 12.962 | −9.1189 |
| | a8 | | NA | 5.6931 |
| | a9 | | NA | 0.5173 |
| | a10 | | NA | −27.9013 |
| | a11 | | NA | −1.6962 |
| | a12 | | NA | −8.8386 |
| | Nb. of patients | | 32 | 31 |
| Cross validation | AUC_Test | | 0.853 | 0.915 |
| | AUC_Train_mean ([min; max]) | | 0.977 ([0.769; 1]) | 1 ([1; 1]) |

TABLE 5b-continued

| Fibrosis diagnostic performances of y6 to y9 signatures. | | |
|---|---|---|
| Se_Test | 0.889 | 0.889 |
| Se_Train_mean ([min; max]) | 1 ([1; 1]) | 1 ([1; 1]) |
| Sp_Test | 0.786 | 0.846 |
| Sp_Train_mean ([min; max]) | 0.954 ([0.538; 1]) | 1 ([1; 1]) |
| Range_a1 | [−357.6721; −142.5827] | [−86.779; −2.858] |
| Range_a2 | [11.7816; 44.6622] | [3.0506; 5.8002] |
| Range_a3 | [−0.0553; 0.9136] | [0.0298; 1.261] |
| Range_a4 | [−0.1131; 0.0144] | [−23.5113; 0.4583] |
| Range_a5 | [−0.0965; 0.0132] | [6.3854; 10.7571] |
| Range_a6 | [0.146; 3.1594] | [−3.1258; 0.5999] |
| Range_a7 | [4.2797; 21.4363] | [−28.5676; 4.089] |
| Range_a8 | NA | [−0.5118; 0.1986] |
| Range_a9 | NA | [−0.0386; 0.2124] |
| Range_a10 | NA | [−0.0334; 0] |
| Range_a11 | NA | [−0.0252; 0.0137] |
| Range_a12 | NA | [−31.6495; 10.4982] |
| Range_Threshold | [0.5; 0.5] | [0.5; 0.5] |
| Range_a1_rounded | [−358; −142] | [−87; 2] |
| Range_a2_rounded | [11; 45] | [3; 6] |
| Range_a3_rounded | [−1; 1] | [0; 2] |
| Range_a4_rounded | [−1; 1] | [−24; 1] |
| Range_a5_rounded | [−1; 1] | [6; 11] |
| Range_a6_rounded | [0; 4] | [−4; 1] |
| Range_a7_rounded | [4; 22] | [−29; 5] |
| Range_a8_rounded | NA | [−1; 1] |
| Range_a9_rounded | NA | [−1; 1] |
| Range_a10_rounded | NA | [−1; 0] |
| Range_a11_rounded | NA | [−1; 1] |
| Range_a12_rounded | NA | [−32; 11] |
| Range_Threshold_ rounded | [0.5; 0.5] | [0.5; 0.5] |
| Range_a1_rounded_ global | [−20127; −2] | [−20127; −2] |
| Range_a2_rounded_ global | [0; 1459] | [0; 1459] |
| Range_a3_rounded_ global | [−1; 129] | [−1; 129] |
| Range_a4 _rounded_ global | [−24; 1] | [−24; 1] |
| Range_a5_rounded_ global | [−1; 11] | [−1; 11] |
| Range_a6_rounded_ global | [−4; 4] | [−4; 4] |
| Range_a7_rounded_ global | [−1; 462] | [−29; 5] |
| Range_a8_rounded_ global | NA | [−1; 462] |
| Range_a9_rounded_ global | NA | [−1; 1] |
| Range_a10_rounded_ global | NA | [−1; 0] |
| Range_a11_rounded_ global | NA | [−1; 1] |
| Range_a12_rounded_ global | NA | [−32; 11] |
| Range Threshold_ rounded_global | [0.1; 0.9] | [0.1; 0.9] |
| Number of patients | 32 | 31 |

TABLE 6

| NASH diagnostic performances of commercial and free available fibrosis tests. | | | | | | | | |
|---|---|---|---|---|---|---|---|---|
| NASH | Diagnostic | Liver stiffness | Fibro-test ® | Hepa-Score ® | APRI | Forns | FIB4 | NAFLD Fibrosis Score |
| Whole data | AUC | 0.607 | 0.517 | 0.501 | 0.653 | 0.568 | 0.550 | 0.523 |
| | Accuracy | 0.58 | 0.6 | 0.58 | 0.68 | 0.60 | 0.59 | 0.58 |
| | Sensitivity | 0.42 | 0.48 | 0.78 | 0.76 | 0.73 | 0.43 | 0.54 |
| | Specificity | 0.77 | 0.74 | 0.36 | 0.59 | 0.46 | 0.77 | 0.62 |

TABLE 6-continued

NASH diagnostic performances of commercial and free available fibrosis tests.

| NASH Diagnostic | Liver stiffness | Fibro-test ® | Hepa-Score ® | APRI | Forns | FIB4 | NAFLD Fibrosis Score |
|---|---|---|---|---|---|---|---|
| PPV | 0.7 | 0.67 | 0.56 | 0.67 | 0.6 | 0.67 | 0.59 |
| NPV | 0.52 | 0.57 | 0.61 | 0.7 | 0.6 | 0.56 | 0.56 |
| Threshold | 11.95 | 0.3824 | 0.5784 | 0.5013 | 5.6272 | 2.1776 | −0.0127 |

TABLE 7

Fibrosis diagnostic performances of commercial and free available fibrosis tests.

| Advanced fibrosis (F ≥ 3) staging in NASH patients | | Liver stiffness | Hepa-Score ® | Fibro-test ® | FIB4 | NAFLD Fibrosis Score | Forns | APRI |
|---|---|---|---|---|---|---|---|---|
| Whole data | AUC | 0.903 | 0.852 | 0.846 | 0.807 | 0.631 | NA | NA |
| | Accuracy | 0.87 | 0.78 | 0.75 | 0.43 | 0.29 | NA | NA |
| | Sensitivity | 0.95 | 0.57 | 0.59 | 0.29 | 0.24 | NA | NA |
| | Specificity | 0.76 | 1 | 0.91 | 0.57 | 0.35 | NA | NA |
| | PPV | 0.83 | 1 | 0.87 | 1 | 0.56 | NA | NA |
| | NPV | 0.93 | 0.69 | 0.69 | 0.8 | 0.7 | NA | NA |
| | Threshold | 8.95 | 0.5 | 0.59 | 1.45; 3.25 | −1.455; 0.676 | NA | NA |

TABLE 8a

Accuracy, Sensitivity, Specificity, PPV and NPV of the three markers function y1 (NASH) according to threshold.

| Threshold | Accuracy | Sensitivity | Specificity | PPV | NPV |
|---|---|---|---|---|---|
| 0.1 | 0.54 | 1.00 | 0.05 | 0.53 | 1.00 |
| 0.2 | 0.55 | 0.97 | 0.11 | 0.54 | 0.80 |
| 0.3 | 0.59 | 0.90 | 0.27 | 0.56 | 0.71 |
| 0.4 | 0.71 | 0.79 | 0.62 | 0.69 | 0.74 |
| 0.5 | 0.76 | 0.69 | 0.84 | 0.82 | 0.72 |
| 0.6 | 0.71 | 0.51 | 0.92 | 0.87 | 0.64 |
| 0.7 | 0.70 | 0.49 | 0.92 | 0.86 | 0.63 |
| 0.8 | 0.63 | 0.33 | 0.95 | 0.87 | 0.57 |
| 0.9 | 0.55 | 0.15 | 0.97 | 0.86 | 0.52 |

TABLE 8b

Accuracy, Sensitivity, Specificity, PPV and NPV of the three markers NASH function y2 (NASH) according to threshold.

| Threshold | Accuracy | Sensitivity | Specificity | PPV | NPV |
|---|---|---|---|---|---|
| 0.1 | 0.58 | 0.97 | 0.15 | 0.56 | 0.83 |
| 0.2 | 0.64 | 0.97 | 0.26 | 0.60 | 0.90 |
| 0.3 | 0.67 | 0.92 | 0.38 | 0.62 | 0.81 |
| 0.4 | 0.72 | 0.89 | 0.53 | 0.68 | 0.82 |
| 0.5 | 0.76 | 0.82 | 0.71 | 0.76 | 0.77 |
| 0.6 | 0.68 | 0.53 | 0.85 | 0.80 | 0.62 |
| 0.7 | 0.67 | 0.42 | 0.94 | 0.89 | 0.59 |
| 0.8 | 0.64 | 0.37 | 0.94 | 0.88 | 0.57 |
| 0.9 | 0.60 | 0.24 | 1.00 | 1.00 | 0.54 |

TABLE 8c

Accuracy, Sensitivity, Specificity, PPV and NPV of the three markers NASH function y3 (NASH) according to threshold.

| Threshold | Accuracy | Sensitivity | Specificity | PPV | NPV |
|---|---|---|---|---|---|
| 0.1 | 0.53 | 1.00 | 0.05 | 0.52 | 1.00 |
| 0.2 | 0.56 | 0.97 | 0.14 | 0.54 | 0.83 |
| 0.3 | 0.63 | 0.92 | 0.32 | 0.58 | 0.80 |
| 0.4 | 0.72 | 0.82 | 0.62 | 0.69 | 0.77 |

TABLE 8c-continued

Accuracy, Sensitivity, Specificity, PPV and NPV of the three markers NASH function y3 (NASH) according to threshold.

| Threshold | Accuracy | Sensitivity | Specificity | PPV | NPV |
|---|---|---|---|---|---|
| 0.5 | 0.73 | 0.66 | 0.81 | 0.78 | 0.70 |
| 0.6 | 0.72 | 0.53 | 0.92 | 0.87 | 0.65 |
| 0.7 | 0.68 | 0.45 | 0.92 | 0.85 | 0.62 |
| 0.8 | 0.64 | 0.34 | 0.95 | 0.87 | 0.58 |
| 0.9 | 0.55 | 0.13 | 0.97 | 0.83 | 0.52 |

TABLE 8d

Accuracy, Sensitivity, Specificity, PPV and NPV of the three markers NASH function y4 (NASH) according to threshold.

| Threshold | Accuracy | Sensitivity | Specificity | PPV | NPV |
|---|---|---|---|---|---|
| 0.1 | 0.56 | 1.00 | 0.04 | 0.55 | 1.00 |
| 0.2 | 0.64 | 1.00 | 0.21 | 0.60 | 1.00 |
| 0.3 | 0.69 | 0.94 | 0.39 | 0.65 | 0.85 |
| 0.4 | 0.74 | 0.76 | 0.71 | 0.76 | 0.71 |
| 0.5 | 0.79 | 0.73 | 0.86 | 0.86 | 0.73 |
| 0.6 | 0.74 | 0.61 | 0.89 | 0.87 | 0.66 |
| 0.7 | 0.74 | 0.61 | 0.89 | 0.87 | 0.66 |
| 0.8 | 0.67 | 0.45 | 0.93 | 0.88 | 0.59 |
| 0.9 | 0.56 | 0.21 | 0.96 | 0.88 | 0.51 |

TABLE 8e

Accuracy, Sensitivity, Specificity, PPV and NPV of the three markers NASH function y5 (NASH) according to threshold.

| Threshold | Accuracy | Sensitivity | Specificity | PPV | NPV |
|---|---|---|---|---|---|
| 0.1 | 0.58 | 0.97 | 0.15 | 0.56 | 0.83 |
| 0.2 | 0.62 | 0.97 | 0.24 | 0.59 | 0.89 |
| 0.3 | 0.67 | 0.92 | 0.38 | 0.62 | 0.81 |
| 0.4 | 0.72 | 0.89 | 0.53 | 0.68 | 0.82 |
| 0.5 | 0.79 | 0.84 | 0.74 | 0.78 | 0.81 |

TABLE 8e-continued

Accuracy, Sensitivity, Specificity, PPV and NPV of the three
markers NASH function y5 (NASH) according to threshold.

| Threshold | Accuracy | Sensitivity | Specificity | PPV | NPV |
|---|---|---|---|---|---|
| 0.6 | 0.67 | 0.50 | 0.85 | 0.79 | 0.60 |
| 0.7 | 0.67 | 0.42 | 0.94 | 0.89 | 0.59 |
| 0.8 | 0.64 | 0.37 | 0.94 | 0.88 | 0.57 |
| 0.9 | 0.61 | 0.29 | 0.97 | 0.92 | 0.55 |

TABLE 8f

Accuracy, Sensitivity, Specificity, PPV and NPV of the three
markers NASH function y6 (NASH) according to threshold.

| Threshold | Accuracy | Sensitivity | Specificity | PPV | NPV |
|---|---|---|---|---|---|
| 0.1 | 0.65 | 1.00 | 0.20 | 0.62 | 1.00 |
| 0.2 | 0.74 | 1.00 | 0.40 | 0.68 | 1.00 |
| 0.3 | 0.79 | 1.00 | 0.52 | 0.73 | 1.00 |
| 0.4 | 0.82 | 0.97 | 0.64 | 0.78 | 0.94 |
| 0.5 | 0.77 | 0.78 | 0.76 | 0.81 | 0.73 |
| 0.6 | 0.74 | 0.66 | 0.84 | 0.84 | 0.66 |
| 0.7 | 0.74 | 0.59 | 0.92 | 0.90 | 0.64 |
| 0.8 | 0.68 | 0.50 | 0.92 | 0.89 | 0.59 |
| 0.9 | 0.63 | 0.38 | 0.96 | 0.92 | 0.55 |

TABLE 8g

Accuracy, Sensitivity, Specificity, PPV and NPV of the three
markers NASH function y7 (NASH) according to threshold.

| Threshold | Accuracy | Sensitivity | Specificity | PPV | NPV |
|---|---|---|---|---|---|
| 0.1 | 0.55 | 1.00 | 0.04 | 0.54 | 1.00 |
| 0.2 | 0.63 | 1.00 | 0.21 | 0.59 | 1.00 |
| 0.3 | 0.70 | 0.97 | 0.39 | 0.65 | 0.92 |
| 0.4 | 0.75 | 0.78 | 0.71 | 0.76 | 0.74 |
| 0.5 | 0.78 | 0.72 | 0.86 | 0.85 | 0.73 |
| 0.6 | 0.73 | 0.59 | 0.89 | 0.86 | 0.66 |
| 0.7 | 0.73 | 0.59 | 0.89 | 0.86 | 0.66 |
| 0.8 | 0.67 | 0.44 | 0.93 | 0.88 | 0.59 |
| 0.9 | 0.55 | 0.19 | 0.96 | 0.86 | 0.51 |

TABLE 8h

Accuracy, Sensitivity, Specificity, PPV and NPV of the three
markers NASH function y8 (NASH) according to threshold.

| Threshold | Accuracy | Sensitivity | Specificity | PPV | NPV |
|---|---|---|---|---|---|
| 0.1 | 0.65 | 1.00 | 0.20 | 0.62 | 1.00 |
| 0.2 | 0.74 | 1.00 | 0.40 | 0.68 | 1.00 |
| 0.3 | 0.81 | 1.00 | 0.56 | 0.74 | 1.00 |
| 0.4 | 0.81 | 0.97 | 0.60 | 0.76 | 0.94 |
| 0.5 | 0.77 | 0.78 | 0.76 | 0.81 | 0.73 |
| 0.6 | 0.75 | 0.69 | 0.84 | 0.85 | 0.68 |
| 0.7 | 0.74 | 0.59 | 0.92 | 0.90 | 0.64 |
| 0.8 | 0.68 | 0.50 | 0.92 | 0.89 | 0.59 |
| 0.9 | 0.63 | 0.38 | 0.96 | 0.92 | 0.55 |

TABLE 8i

Accuracy, Sensitivity, Specificity, PPV and NPV of the three
markers NASH function y9 (NASH) according to threshold.

| Threshold | Accuracy | Sensitivity | Specificity | PPV | NPV |
|---|---|---|---|---|---|
| 0.1 | 0.66 | 1.00 | 0.24 | 0.62 | 1.00 |
| 0.2 | 0.77 | 1.00 | 0.48 | 0.70 | 1.00 |
| 0.3 | 0.79 | 0.94 | 0.60 | 0.74 | 0.88 |

TABLE 8i-continued

Accuracy, Sensitivity, Specificity, PPV and NPV of the three
markers NASH function y9 (NASH) according to threshold.

| Threshold | Accuracy | Sensitivity | Specificity | PPV | NPV |
|---|---|---|---|---|---|
| 0.4 | 0.80 | 0.90 | 0.68 | 0.78 | 0.85 |
| 0.5 | 0.77 | 0.74 | 0.80 | 0.82 | 0.71 |
| 0.6 | 0.79 | 0.74 | 0.84 | 0.85 | 0.72 |
| 0.7 | 0.75 | 0.65 | 0.88 | 0.87 | 0.67 |
| 0.8 | 0.71 | 0.55 | 0.92 | 0.89 | 0.62 |
| 0.9 | 0.66 | 0.42 | 0.96 | 0.93 | 0.57 |

TABLE 9a

Accuracy, Sensitivity, Specificity, PPV and NPV of the three
markers function y1 (fibrosis) according to threshold.

| Threshold | Accuracy | Sensitivity | Specificity | PPV | NPV |
|---|---|---|---|---|---|
| 0.1 | 0.85 | 1.00 | 0.68 | 0.77 | 1.00 |
| 0.2 | 0.90 | 0.95 | 0.84 | 0.86 | 0.94 |
| 0.3 | 0.87 | 0.90 | 0.84 | 0.86 | 0.89 |
| 0.4 | 0.87 | 0.90 | 0.84 | 0.86 | 0.89 |
| 0.5 | 0.90 | 0.90 | 0.89 | 0.90 | 0.89 |
| 0.6 | 0.85 | 0.80 | 0.89 | 0.89 | 0.81 |
| 0.7 | 0.85 | 0.80 | 0.89 | 0.89 | 0.81 |
| 0.8 | 0.87 | 0.75 | 1.00 | 1.00 | 0.79 |
| 0.9 | 0.85 | 0.70 | 1.00 | 1.00 | 0.76 |

TABLE 9b

Accuracy, Sensitivity, Specificity, PPV and NPV of the three
markers NASH function y2 (fibrosis) according to threshold.

| Threshold | Accuracy | Sensitivity | Specificity | PPV | NPV |
|---|---|---|---|---|---|
| 0.1 | 0.82 | 1.00 | 0.63 | 0.73 | 1.00 |
| 0.2 | 0.89 | 0.95 | 0.84 | 0.86 | 0.94 |
| 0.3 | 0.89 | 0.95 | 0.84 | 0.86 | 0.94 |
| 0.4 | 0.87 | 0.89 | 0.84 | 0.85 | 0.89 |
| 0.5 | 0.87 | 0.89 | 0.84 | 0.85 | 0.89 |
| 0.6 | 0.89 | 0.89 | 0.89 | 0.89 | 0.89 |
| 0.7 | 0.87 | 0.79 | 0.95 | 0.94 | 0.82 |
| 0.8 | 0.84 | 0.68 | 1.00 | 1.00 | 0.76 |
| 0.9 | 0.84 | 0.68 | 1.00 | 1.00 | 0.76 |

TABLE 9c

Accuracy, Sensitivity, Specificity, PPV and NPV of the three
markers NASH function y3 (fibrosis) according to threshold.

| Threshold | Accuracy | Sensitivity | Specificity | PPV | NPV |
|---|---|---|---|---|---|
| 0.1 | 0.87 | 0.95 | 0.79 | 0.82 | 0.94 |
| 0.2 | 0.89 | 0.95 | 0.84 | 0.86 | 0.94 |
| 0.3 | 0.92 | 0.95 | 0.89 | 0.90 | 0.94 |
| 0.4 | 0.95 | 0.95 | 0.95 | 0.95 | 0.95 |
| 0.5 | 0.95 | 0.95 | 0.95 | 0.95 | 0.95 |
| 0.6 | 0.97 | 0.95 | 1.00 | 1.00 | 0.95 |
| 0.7 | 0.97 | 0.95 | 1.00 | 1.00 | 0.95 |
| 0.8 | 0.92 | 0.84 | 1.00 | 1.00 | 0.86 |
| 0.9 | 0.87 | 0.74 | 1.00 | 1.00 | 0.79 |

TABLE 9d

Accuracy, Sensitivity, Specificity, PPV and NPV of the three
markers NASH function y4 (fibrosis) according to threshold.

| Threshold | Accuracy | Sensitivity | Specificity | PPV | NPV |
|---|---|---|---|---|---|
| 0.1 | 0.91 | 1.00 | 0.79 | 0.86 | 1.00 |
| 0.2 | 0.94 | 1.00 | 0.86 | 0.90 | 1.00 |
| 0.3 | 0.94 | 1.00 | 0.86 | 0.90 | 1.00 |
| 0.4 | 0.91 | 0.95 | 0.86 | 0.90 | 0.92 |
| 0.5 | 0.91 | 0.95 | 0.86 | 0.90 | 0.92 |
| 0.6 | 0.91 | 0.89 | 0.93 | 0.94 | 0.87 |
| 0.7 | 0.91 | 0.89 | 0.93 | 0.94 | 0.87 |
| 0.8 | 0.88 | 0.84 | 0.93 | 0.94 | 0.81 |
| 0.9 | 0.82 | 0.74 | 0.93 | 0.93 | 0.72 |

TABLE 9e

Accuracy, Sensitivity, Specificity, PPV and NPV of the three
markers NASH function y5 (fibrosis) according to threshold.

| Threshold | Accuracy | Sensitivity | Specificity | PPV | NPV |
|---|---|---|---|---|---|
| 0.1 | 0.84 | 0.95 | 0.74 | 0.78 | 0.93 |
| 0.2 | 0.89 | 0.95 | 0.84 | 0.86 | 0.94 |
| 0.3 | 0.92 | 0.95 | 0.89 | 0.90 | 0.94 |
| 0.4 | 0.95 | 0.95 | 0.95 | 0.95 | 0.95 |
| 0.5 | 0.95 | 0.95 | 0.95 | 0.95 | 0.95 |
| 0.6 | 0.97 | 0.95 | 1.00 | 1.00 | 0.95 |
| 0.7 | 0.97 | 0.95 | 1.00 | 1.00 | 0.95 |
| 0.8 | 0.95 | 0.89 | 1.00 | 1.00 | 0.90 |
| 0.9 | 0.89 | 0.79 | 1.00 | 1.00 | 0.83 |

TABLE 9f

Accuracy, Sensitivity, Specificity, PPV and NPV of the three
markers NASH function y6 (fibrosis) according to threshold.

| Threshold | Accuracy | Sensitivity | Specificity | PPV | NPV |
|---|---|---|---|---|---|
| 0.1 | 0.94 | 1.00 | 0.86 | 0.90 | 1.00 |
| 0.2 | 0.94 | 1.00 | 0.86 | 0.90 | 1.00 |
| 0.3 | 0.94 | 1.00 | 0.86 | 0.90 | 1.00 |
| 0.4 | 0.94 | 1.00 | 0.86 | 0.90 | 1.00 |
| 0.5 | 0.97 | 1.00 | 0.93 | 0.95 | 1.00 |
| 0.6 | 0.94 | 0.94 | 0.93 | 0.94 | 0.93 |
| 0.7 | 0.91 | 0.89 | 0.93 | 0.94 | 0.87 |
| 0.8 | 0.88 | 0.83 | 0.93 | 0.94 | 0.81 |
| 0.9 | 0.81 | 0.72 | 0.93 | 0.93 | 0.72 |

TABLE 9g

Accuracy, Sensitivity, Specificity, PPV and NPV of the three
markers NASH function y7 (fibrosis) according to threshold.

| Threshold | Accuracy | Sensitivity | Specificity | PPV | NPV |
|---|---|---|---|---|---|
| 0.1 | 1 | 1 | 1 | 1 | 1 |
| 0.2 | 1 | 1 | 1 | 1 | 1 |
| 0.3 | 1 | 1 | 1 | 1 | 1 |
| 0.4 | 1 | 1 | 1 | 1 | 1 |
| 0.5 | 1 | 1 | 1 | 1 | 1 |
| 0.6 | 1 | 1 | 1 | 1 | 1 |
| 0.7 | 1 | 1 | 1 | 1 | 1 |
| 0.8 | 1 | 1 | 1 | 1 | 1 |
| 0.9 | 1 | 1 | 1 | 1 | 1 |

TABLE 9h

Accuracy, Sensitivity, Specificity, PPV and NPV of the three
markers NASH function y8 (fibrosis) according to threshold.

| Threshold | Accuracy | Sensitivity | Specificity | PPV | NPV |
|---|---|---|---|---|---|
| 0.1 | 1 | 1 | 1 | 1 | 1 |
| 0.2 | 1 | 1 | 1 | 1 | 1 |
| 0.3 | 1 | 1 | 1 | 1 | 1 |
| 0.4 | 1 | 1 | 1 | 1 | 1 |
| 0.5 | 1 | 1 | 1 | 1 | 1 |
| 0.6 | 1 | 1 | 1 | 1 | 1 |
| 0.7 | 1 | 1 | 1 | 1 | 1 |
| 0.8 | 1 | 1 | 1 | 1 | 1 |
| 0.9 | 1 | 1 | 1 | 1 | 1 |

TABLE 9i

Accuracy, Sensitivity, Specificity, PPV and NPV of the three
markers NASH function y9 (fibrosis) according to threshold.

| Threshold | Accuracy | Sensitivity | Specificity | PPV | NPV |
|---|---|---|---|---|---|
| 0.1 | 1 | 1 | 1 | 1 | 1 |
| 0.2 | 1 | 1 | 1 | 1 | 1 |
| 0.3 | 1 | 1 | 1 | 1 | 1 |
| 0.4 | 1 | 1 | 1 | 1 | 1 |
| 0.5 | 1 | 1 | 1 | 1 | 1 |
| 0.6 | 1 | 1 | 1 | 1 | 1 |
| 0.7 | 1 | 1 | 1 | 1 | 1 |
| 0.8 | 1 | 1 | 1 | 1 | 1 |
| 0.9 | 1 | 1 | 1 | 1 | 1 |

TABLE 10

Treatments for non-alcoholic steatohepatitis (NASH).

| Reference | Treatment and dosage |
|---|---|
| Pioglitazone and vitamin E | |
| Sanyal et al. "Pioglitazone, vitamin E, or placebo for nonalcoholic steatohepatitis." N Engl J Med. 2010; 362: 1675-1685. | Pioglitazone about 30 mg/d alone or in combination with vitamin E at about 800 IU/d |
| Cusi et al. "Long-term pioglitazone treatment for patients with nonalcoholic steatohepatitis and prediabetes or type 2 diabetes mellitus: a randomized trial." Ann Intern Med. 2016; 165: 305-315. | Pioglitazone at about 45 mg/d |
| FXR agonist- Obeticholic Acid (INT-747) | |
| Mudaliar et al. "Efficacy and safety of the farnesoid X receptor agonist obeticholic acid in patients with type 2 diabetes and nonalcoholic fatty liver disease." Gastroenterology. 2013; 145: 574-582. | Obeticholic Acid at about 25 mg/d |
| Neuschwander et al. "Farnesoid X nuclear receptor ligand obeticholic acid for non-cirrhotic, non-alcoholic steatohepatitis (FLINT): a multicentre, randomised, placebo-controlled trial." Lancet. 2015; 385: 956-965. | Obeticholic Acid at 25 about mg/d |
| PPAR α/δ agonist-elafibranor (GFT-505) | |
| Ratziu et al. "Elafibranor, an Agonist of the Peroxisome Proliterator-Activated Receptor-alpha and -delta, Induces Resolution of Nonalcoholic Steatohepatitis Without Fibrosis Worsening." Gastroenterology. 2016; 150: 1147-1159. | Elafibranor at about 80 mg/d to about 120 mg/d placebo |

TABLE 10-continued

Treatments for non-alcoholic steatohepatitis (NASH).

| Reference | Treatment and dosage |
|---|---|
| SCD1inhibitor-aramchol | |
| Safadi et al. "The fatty acid-bile acid conjugate Aramchol reduces liver fat content in patients with nonalcoholic fatty liver disease." *Clin Gastroenterol Hepatol.* 2014; 12: 2085-2091. | Aramchol at about 100 mg/d to about 300 mg/d |
| GLP-1-liraglutide | |
| Armstrong et al. "Liraglutide safety and efficacy in patients with non-alcoholic steatohepatitis (LEAN): a multicentre, double-blind, randomised, placebo-controlled phase 2 study." *Lancet.* 2016; 387: 679-690. | Liraglutide at about 1.8 mg/d |

TABLE 11

Treatments for non-alcoholic steatohepatitis (NASH).

| Drug | Dosages |
|---|---|
| Elafibranor | About 50 mg/d to about 120 mg/d |
| Saroglitazar | about 4 mg/d to about 20 mg/d |
| Obeticholic Acid | about 10 mg/d to about 25 mg/d |
| LNJ452 (tropifexor) | about 2 mg/d to about 20 mg/d |
| NGM282 (FGF19 analogue) (MRDSSPLVHYGWGDPI; SEQ ID NO: 1) | about 1 mg/d to about 6 mg/d |
| Aramchol | about 400 mg to about 600 mg |
| GS-4997 (selonsertib) | selonsertib at about 6 mg/d to about 40 mg/d alone or in combination with simtuzumab at about 125 mg per week or every two weeks |

TABLE 11-continued

Treatments for non-alcoholic steatohepatitis (NASH).

| Drug | Dosages |
|---|---|
| GS-4997 (selonsertib) | selonsertib at about 6 mg/d to about 40 mg/d alone or in combination with fenofibrate at about 30 mg/d to about 200 mg/d |
| Cenicriviroc | about 75 mg/day to about 150 mg/d |
| Emricasan | about 5 mg/BID to about 50 mg/BID |
| Simtuzumab | about 75 mg to about 700 mg per week (or every two weeks) or about 75 mg to about 200 mg per week (or every two weeks) |
| GR-MD-02 (galactoarabino rhamnogalacturonate) | about 2 mg/d to 10 mg/kg lean body mass every other week |
| BMS 130 045 (BMS 986036; pegylated FGF21 (CAS Registry # 1966977-70-7) | about 5 mg/d to about 50 mg/day, subcutaneously |
| EDP-305 | about 5 mg/s to about 50 mg/d |
| IMM-124E (encapsulated hyperimmune bovine colostrum enriched with anti-LPS antibodies) | about 300 mg to about 1500 mg up to three times daily |
| IVA337 (lanifibranor) | about 200 mg/d to about 1200 mg/d or about 400 mg/d |
| LMB763 | about 5 mg/d to about 750 mg/d |
| LIK066 (licogliflozin) | about 100 mg/d to about 300 mg/d |
| MGL-3196 (CAS Registry # 920509-32-6) | about 60 mg/d to about 100 mg/d |
| MSDC 0602K (CAS Registry # 1133819-87-0) | about 50 mg/d to about 300 mg/d |
| PF-05221304 (CAS Registry # 1301214-47-0) | about 2 mg/d to about 60 mg/d |
| SAR425899 | once daily subcutaneous injection of about 20 microgram to about 300 microgram |
| Selonsertib + GS-0976 + GS-9674 | about 15 mg/d to about 30 mg/d for each active agent |
| Semaglutide | once daily subcutaneous injection of about 0.1 to about 0.5 mg |
| volixibat | about 5 mg/d to about 50 mg/d |

The invention claimed is:

1. A kit for diagnosing NASH and/or the hepatic fibrosis status of a subject comprising:

(i) antibodies for determining, in a blood, plasma, serum, urine or cerebrospinal fluid sample obtained from a subject, levels of at least three biomarkers, said at least three biomarkers being a pro-inflammatory cytokine, a chemokine and a glycosaminoglycan contributing to cell-adhesion and tissue modeling, wherein:

(a) the pro-inflammatory cytokine is IL-8;

(b) the chemokine is CXCL10;

(c) the glycosaminoglycan contributing to cell-adhesion and tissue modeling is hyaluronic acid; and (ii) instructions, said instructions disclosing:

contacting said sample with antibodies that bind to said at least three biomarkers and determining the levels of said IL-8, CXCL10 and HA in said sample;

calculating a value for $f_{1(NASH)}$ and/or $f_{1(fibrosis)}$, wherein $$f_{1(NASH)} = \frac{\exp(y_{1(NASH)})}{1 + \exp(y_{1(NASH)})} \text{ wherein } f_{1(NASH)} : y_{1(NASH)} =$$

$$(-2.3083 + 0.4079 \times IL8 - 0.0129 \times HA + 0.0019 \times CXCL10) \text{ and}$$

-continued $$f_{1(fibrosis)} = \frac{\exp(y_{1(fibrosis)})}{1 + \exp(y_{1(fibrosis)})} \text{ where}$$

$$y_{1(fibrosis)} = (-7.0457 + 1.0511 \times IL8 + 0.067 \times HA + 0.0004 \times CXCL10)$$

and when $f_{1(NASH)} > 0.4997$, the subject is diagnosed with NASH and when $f_{1(NASH)} \leq 0.4997$, the subject is diagnosed with non-alcoholic fatty liver (NAFL) and when $f_{1(fibrosis)} > 0.1953$, the subject is diagnosed with advanced liver fibrosis and when $f_{1(fibrosis)} \leq 0.1953$, the subject is diagnosed with early-moderate liver fibrosis.

2. The kit of claim 1, further comprising antibodies for determining, in a sample obtained from the subject, the levels of one or more of ghrelin, haptoglobin and pre-HP2.

3. The kit of claim 1, wherein:

(i) the kit comprises labeled antibodies that bind the biomarkers and the measuring the levels of biomarkers is done by ELISA, Luminex multiplex technology, microarray or point of care testing; and/or (ii) the sample is a plasma or serum blood.

4. The kit according to claim 3, wherein the antibodies are fluorescently labeled.

5. The kit according to claim 2, wherein the antibodies are fluorescently labeled.

\* \* \* \* \*